(12) United States Patent
Kwong et al.

(10) Patent No.: US 11,549,947 B2
(45) Date of Patent: *Jan. 10, 2023

(54) MULTIPLEXED DETECTION WITH ISOTOPE-CODED REPORTERS

(71) Applicant: Massachusetts Institute of Technology, Cambridge, MA (US)

(72) Inventors: Gabriel A. Kwong, Boston, MA (US); Sangeeta N. Bhatia, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 892 days.

This patent is subject to a terminal disclaimer.

(21) Appl. No.: 15/842,162

(22) Filed: Dec. 14, 2017

(65) Prior Publication Data

US 2018/0196058 A1 Jul. 12, 2018

Related U.S. Application Data

(63) Continuation of application No. 14/005,416, filed as application No. PCT/US2012/029200 on Mar. 15, 2012, now Pat. No. 10,006,916.

(Continued)

(51) Int. Cl.
*G01N 33/58* (2006.01)
*C07K 7/08* (2006.01)
(Continued)

(52) U.S. Cl.
CPC ............... *G01N 33/58* (2013.01); *C07K 7/08* (2013.01); *C07K 14/001* (2013.01);
(Continued)

(58) Field of Classification Search
CPC ........ A61K 38/00; C07K 7/08; C07K 14/001; G01N 33/58; G01N 33/6848; G01N 2458/15
See application file for complete search history.

(56) References Cited

U.S. PATENT DOCUMENTS

5,500,161 A 3/1996 Andrianov et al.
5,811,252 A 9/1998 Verheijen
(Continued)

FOREIGN PATENT DOCUMENTS

CN 102558362 A 7/2012
CN 103012595 A 4/2013
(Continued)

OTHER PUBLICATIONS

Galati et al. (Z. Naturforsch. 58c, 558D561 (2003)) (Year: 2003).*
(Continued)

*Primary Examiner* — Jeremy C Flinders
(74) *Attorney, Agent, or Firm* — Wolf, Greenfield & Sacks, P.C.

(57) ABSTRACT

Some aspects of this invention provide reagents and methods for the sensitive, quantitative and simultaneous detection of target analytes in complex biological samples by liquid chromatography tandem mass spectrometry (LC MS/MS). Some aspects of this invention provide affinity reagents encoded with mass reporters for the sensitive and quantitative translation of an analyte of interest into a mass tag. The reagents and methods provided herein have general utility in analyte detection and encoding, for example, in biomolecular profiling, molecular diagnostics, and biochemical encoding.

15 Claims, 34 Drawing Sheets

Specification includes a Sequence Listing.

Related U.S. Application Data

(60) Provisional application No. 61/452,908, filed on Mar. 15, 2011.

(51) Int. Cl.
   *A61K 38/00*    (2006.01)
   *C07K 14/00*    (2006.01)
   *G01N 33/68*    (2006.01)

(52) U.S. Cl.
   CPC .......... *G01N 33/6848* (2013.01); *A61K 38/00* (2013.01); *G01N 2458/15* (2013.01)

(56) References Cited

U.S. PATENT DOCUMENTS

| | | | |
|---|---|---|---|
| 5,885,775 A | 3/1999 | Haff et al. | |
| 6,335,429 B1 | 1/2002 | Cai et al. | |
| 6,592,847 B1 | 7/2003 | Weissleder et al. | |
| 6,597,996 B1 | 7/2003 | Venkataraman et al. | |
| 6,629,040 B1 | 9/2003 | Goodlett et al. | |
| 6,824,981 B2 | 11/2004 | Chait et al. | |
| 7,041,453 B2 | 5/2006 | Yang | |
| 7,179,655 B2 | 2/2007 | Patricelli | |
| 7,329,506 B2 | 2/2008 | William | |
| 7,412,332 B1 | 8/2008 | Venkataraman et al. | |
| 7,456,269 B2 | 11/2008 | Gurney et al. | |
| 7,468,258 B2 | 12/2008 | Owen | |
| 7,544,518 B2 | 6/2009 | Aebersold et al. | |
| 7,595,155 B2 | 9/2009 | Murakami | |
| 8,673,267 B2 | 3/2014 | Bhatia et al. | |
| 9,006,415 B2 | 4/2015 | Ren et al. | |
| 9,155,471 B2 | 10/2015 | Lee et al. | |
| 9,913,917 B2 | 3/2018 | Groves et al. | |
| 9,970,941 B2 | 5/2018 | Bhatia et al. | |
| 10,006,916 B2 | 6/2018 | Kwong et al. | |
| 10,883,998 B2 | 1/2021 | Bhatia et al. | |
| 11,054,428 B2 | 7/2021 | Bhatia et al. | |
| 2002/0119490 A1 | 8/2002 | Aebersold et al. | |
| 2003/0059952 A1 | 3/2003 | Chait et al. | |
| 2004/0014652 A1 | 1/2004 | Dubois et al. | |
| 2004/0091943 A1 | 5/2004 | Schneider | |
| 2005/0260695 A1 | 11/2005 | Fleming et al. | |
| 2006/0008856 A1 | 1/2006 | Singh et al. | |
| 2006/0292631 A1 | 12/2006 | Broberg et al. | |
| 2007/0010433 A1 | 1/2007 | Albrechtsen et al. | |
| 2007/0048752 A1 | 3/2007 | Yan et al. | |
| 2007/0207555 A1 | 9/2007 | Guerra et al. | |
| 2008/0026480 A1 | 1/2008 | Guerra | |
| 2008/0064607 A1 | 3/2008 | Yang | |
| 2008/0095758 A1 | 4/2008 | Lee et al. | |
| 2008/0113875 A1 | 5/2008 | Chaurand et al. | |
| 2008/0213377 A1 | 9/2008 | Bhatia et al. | |
| 2008/0241955 A1 | 10/2008 | Purkayastha et al. | |
| 2008/0253960 A1 | 10/2008 | Zheng et al. | |
| 2009/0016988 A1 | 1/2009 | Buckley | |
| 2009/0088332 A1 | 4/2009 | Ju et al. | |
| 2009/0156424 A1 | 6/2009 | Thompson | |
| 2009/0246142 A1 | 10/2009 | Bhatia et al. | |
| 2009/0252677 A1 | 10/2009 | Bogyo et al. | |
| 2010/0022408 A1 | 1/2010 | Singh et al. | |
| 2010/0124757 A1 | 5/2010 | Kwon et al. | |
| 2010/0190193 A1 | 7/2010 | Calatzis et al. | |
| 2010/0240050 A1 | 9/2010 | Bhatia et al. | |
| 2010/0317542 A1 | 12/2010 | Lim et al. | |
| 2011/0021908 A1 | 1/2011 | Lee et al. | |
| 2011/0104052 A1 | 5/2011 | Barnett et al. | |
| 2011/0104071 A1 | 5/2011 | Lee et al. | |
| 2012/0039990 A1 | 2/2012 | Reshetnyak et al. | |
| 2012/0150164 A1 | 6/2012 | Lee et al. | |
| 2014/0207129 A1 | 7/2014 | Lee | |
| 2014/0234431 A1 | 8/2014 | Bhatia et al. | |
| 2014/0276102 A1 | 9/2014 | Lee et al. | |
| 2014/0276103 A1 | 9/2014 | Lee et al. | |
| 2014/0301950 A1 | 10/2014 | Lee et al. | |
| 2014/0303014 A1 | 10/2014 | Kwong et al. | |
| 2014/0363833 A1 | 12/2014 | Bhatia et al. | |
| 2015/0051153 A1 | 2/2015 | Reshetnyak et al. | |
| 2015/0080721 A1 | 3/2015 | Novak et al. | |
| 2015/0104381 A1 | 4/2015 | Maina-Nock et al. | |
| 2015/0165062 A1 | 6/2015 | Liao et al. | |
| 2016/0025632 A1 | 1/2016 | Lee et al. | |
| 2016/0096869 A1 | 4/2016 | Hansen et al. | |
| 2016/0184459 A1 | 6/2016 | Ueki et al. | |
| 2016/0317037 A1 | 11/2016 | Lee et al. | |
| 2017/0267727 A1 | 9/2017 | Thevenin et al. | |
| 2018/0021090 A1 | 1/2018 | Lee et al. | |
| 2018/0328941 A1 | 11/2018 | Bhatia et al. | |
| 2018/0335429 A1 | 11/2018 | Bhatia et al. | |
| 2020/0116725 A1 | 4/2020 | Bhatia et al. | |
| 2021/0148926 A1 | 5/2021 | Bhatia et al. | |
| 2021/0262025 A1 | 8/2021 | Bhatia et al. | |

FOREIGN PATENT DOCUMENTS

| | | |
|---|---|---|
| CN | 108484847 A | 9/2018 |
| JP | 2004-506900 | 3/2004 |
| JP | 2004-129651 | 4/2004 |
| JP | 2007-24631 A2 | 2/2007 |
| JP | 2007-206054 A | 8/2007 |
| JP | 2009-108037 | 5/2009 |
| JP | 2009-524688 | 7/2009 |
| JP | 2009-538430 A | 11/2009 |
| JP | 2013-060452 | 4/2013 |
| JP | 2016-520327 | 7/2016 |
| WO | WO 2002/014867 A2 | 2/2002 |
| WO | WO 2006/034370 A2 | 3/2006 |
| WO | WO 2007/060921 A1 | 5/2007 |
| WO | WO 2007/072070 A1 | 6/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |
| WO | WO 2010/101628 A2 | 9/2010 |
| WO | WO 2011/008996 A2 | 1/2011 |
| WO | WO 2012/031250 A2 | 3/2012 |
| WO | WO 2012/085080 A1 | 6/2012 |
| WO | WO 2012/125808 A1 | 9/2012 |
| WO | WO 2014/107599 A2 | 7/2014 |
| WO | WO 2014/120619 A2 | 8/2014 |
| WO | WO 2014/120974 A1 | 8/2014 |
| WO | WO 2014/176284 A1 | 10/2014 |
| WO | WO 2014/197816 A1 | 12/2014 |
| WO | WO 2015/042202 A1 | 3/2015 |
| WO | WO 2017/044894 A2 | 3/2017 |
| WO | WO 2017/120410 A1 | 7/2017 |
| WO | WO 2017/177115 A1 | 10/2017 |
| WO | WO 2017/180789 A2 | 10/2017 |
| WO | WO 2017/181149 A1 | 10/2017 |
| WO | WO 2018/049285 A1 | 3/2018 |
| WO | WO 2018/064383 A1 | 4/2018 |
| WO | WO 2018/187688 A1 | 10/2018 |
| WO | WO 2018/227132 A1 | 12/2018 |
| WO | WO 2019/071051 A1 | 4/2019 |
| WO | WO 2019/075292 A1 | 4/2019 |
| WO | WO 2019/089804 A1 | 5/2019 |
| WO | WO 2019/089820 A1 | 5/2019 |
| WO | WO 2019/126577 A2 | 6/2019 |
| WO | WO 2019/126716 A1 | 6/2019 |
| WO | WO 2019/126762 A2 | 6/2019 |
| WO | WO 2019/148206 A1 | 8/2019 |

OTHER PUBLICATIONS

Abudayyeh, Nanoparticle-Chaperoned Urinary "Synthetic Biomarkers" for Profiling Proteases in Cancer. Thesis. Department of Mechanical Engineering. Jun. 2012.

Kwon et al., Ultrasensitive tumour-penetrating nanosensors of protease activity. Nat Biomed Eng. 2017;1. pii: 0054. doi:10.1038/s41551-017-0054. Epub Apr. 10, 2017.

Lin et al., Drug-induced amplification of nanoparticle targeting to tumors. Nano Today. Oct. 2014;9(5):550-559. doi:10.1016/j.nantod.2014.09.001. Epub Sep. 23, 2014.

(56) References Cited

OTHER PUBLICATIONS

Schuerle et al., Magnetically Actuated Protease Sensors for in Vivo Tumor Profiling. Nano Lett. Oct. 12, 2016;16(10):6303-6310. Epub Sep. 13, 2016.
PCT/US2014/041370, Sep. 26, 2014, International Search Report and Written Opinion.
12757730.2, Dec. 17, 2014, Partial Supplementary European Search Report.
10 74 9044, Jul. 4, 2012, Extended European Search Report.
PCT/US2010/000633, Sep. 15, 2011, International Preliminary Report on Patentability.
PCT/US2010/000633, Jun. 28, 2010, International Search Report and Written Opinion.
PCT/US2012/029200, Jul. 13, 2012, International Search Report and Written Opinion.
PCT/US2014/041370, Dec. 17, 2015, International Preliminary Report on Patentability.
PCT/US2012/029200, Sep. 26, 2013, International Preliminary Report on Patentability.
PCT/US2018/026458, Jun. 26, 2018, International Search Report and Written Opinion.
Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.
Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.
Asai et al., A colorimetric assay for plasma antithrombin III using a new synthetic peptide substrate (PS-915). Clin Chim Acta. Dec. 29, 1984;144(2-3):163-71.
Baruch et al., Enzyme activity—it's all about image. Trends Cell Biol. Jan. 2004;14(1):29-35.
Becker et al., Thrombin: Structure, Biochemistry, Measurement, and Status in Clinical Medicine. J Thromb Thrombolysis. Jul. 1998;5(3):215-229.
Blum et al., Noninvasive optical imaging of cysteine protease activity using fluorescently quenched activity-based probes. Nat Chem Biol. Oct. 2007;3(10):668-77. Epub Sep. 9, 2007.
Bounameaux et al., Plasma measurement of D-dimer as diagnostic aid in suspected venous thromboembolism: an overview. Thromb Haemost. Jan. 1994;71(1):1-6.
Chen et al., A unique substrate recognition profile for matrix metalloproteinase-2. J Biol Chem. Feb. 8, 2002;277(6):4485-91.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.
Fowlkes et al., Proteolysis of insulin-like growth factor binding protein-3 during rat pregnancy: a role for matrix metalloproteinases. Endocrinology. Dec. 1994;135(6):2810-3.

Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Genbank Submission; NIH/NCBI, Accession No. 2WV1.sub.—A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP.sub.—731669; Hoskins et al.; Dec. 18, 2009.
Genbank Submission; NIH/NCBI, Accession No. NP.sub.—938673; Cerdeno-Tarraga et al.; Jun. 3, 2010.
Genbank Submission; NIH/NCBI, Accession No. XP.sub.—001385378; Jeffries et al.; Apr. 11, 2008.
Genbank Submission; NIH/NCBI, Accession No. XP.sub.—002097000; Clark et al.; Aug. 12, 2009.
Genbank Submission; NIH/NCBI, Accession No. XP.sub.—00234527.; Jul. 7, 2006.
Genbank Submission; NIH/NCBI, Accession No. ZP.sub.—03507634; Gonzalez et al.; Dec. 19, 2008.
Genbank Submission; NIH/NCBI, Accession No. ZP.sub.-06431346; Small et al.; Jun. 9, 2010.
Ghadiali, James E. et al., "Enzyme-Responsive Nanoparticle Systems," Advanced Materials, vol. 20(22):4359-4363 (2008).
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.
Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.
Imai et al., Degradation of decorin by matrix metalloproteinases: identification of the cleavage sites, kinetic analyses and transforming growth factor-beta1 release. Biochem J. Mar. 15, 1997;322 (Pt 3):809-14.
Ito et al., Degradation of interleukin 1beta by matrix metalloproteinases. J Biol Chem. Jun. 21, 1996;271(25):14657-60.
Jaffer et al., In vivo imaging of thrombin activity in experimental thrombi with thrombin-sensitive near-infrared molecular probe. Arterioscler Thromb Vasc Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.
Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H—D—Phe—Pip—Arg—pNA (S-2238). Thromb Res. Aug. 1978;13(2):285-8.
Levi et al., Matrix metalloproteinase 2 releases active soluble ectodomain of fibroblast growth factor receptor 1. Proc Natl Acad Sci USA. Jul. 9, 1996;93(14):7069-74.
Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.

(56) References Cited

OTHER PUBLICATIONS

Mallick et al., Computational prediction of proteotypic peptides for quantitative proteomics. Nat Biotechnol. Jan. 2007;25(1):125-31. Epub Dec. 31, 2006.

Mañes et al., The matrix metalloproteinase-9 regulates the insulin-like growth factor-triggered autocrine response in DU-145 carcinoma cells. J Biol Chem. Mar. 12, 1999;274(11):6935-45.

Martinez et al., Diagnostics for the developing world: microfluidic paper-based analytical devices. Anal Chem. Jan. 1, 2010;82(1):3-10. doi: 10.1021/ac9013989.

Mira et al., Insulin-like growth factor I-triggered cell migration and invasion are mediated by matrix metalloproteinase-9. Endocrinology. Apr. 1999;140(4):1657-64.

Mirtti et al., Expression of cystatins, high molecular weight cytokeratin, and proliferation markers in prostatic adenocarcinoma and hyperplasia. Prostate. Mar. 1, 2003;54(4):290-8.

Mitchell et al., Assay for plasma heparin using a synthetic peptide substrate for thrombin: introduction of the fluorophore aminoisophthalic acid, dimethyl ester. Thromb Res. Jul. 1978;13(1):47-52.

Morris et al., Urine and plasma levels of fibrinopeptide B in patients with deep vein thrombosis and pulmonary embolism. Thromb Res. May 1, 2003;110(2-3):159-65.

Nagase et al., Matrix metalloproteinases. J Biol Chem. Jul. 30, 1999;274(31):21491-4.

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA. 109.193086. Epub Jul. 16, 2009.

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.

Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.

Park et al., Magnetic Iron Oxide Nanoworms for Tumor Targeting and Imaging. Adv Mater. May 5, 2008;20(9):1630-1635.

Park et al., Systematic surface engineering of magnetic nanoworms for in vivo tumor targeting. Small. Mar. 2009;5(6):694-700. doi: 10.1002/smll.200801789.

Peer et al., Nanocarriers as an emerging platform for cancer therapy. Nat Nanotechnol. Dec. 2007;2(12):751-60.

Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.

Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.

Powell et al., The metalloproteinase matrilysin proteolytically generates active soluble Fas ligand and potentiates epithelial cell apoptosis. Curr Biol. Dec. 16-30, 1999;9(24):1441-7.

Rajah et al., Elevated levels of the IGF-binding protein protease MMP-1 in asthmatic airway smooth muscle. Am J Respir Cell Mol Biol. Feb. 1999;20(2):199-208.

Rennke, How does glomerular epithelial cell injury contribute to progressive glomerular damage? Kidney Int Suppl. Feb. 1994;45:S58-63.

Rijkers et al., Design and synthesis of thrombin substrates with modified kinetic parameters. Thromb Res. Sep. 15, 1995;79(5-6):491-9.

Roepstorff et al., Proposal for a common nomenclature for sequence ions in mass spectra of peptides. Biomed Mass Spectrom. Nov. 1984;11(11):601.

Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.

Ruoslahti et al., Targeting of drugs and nanoparticles to tumors. J Cell Biol. Mar. 22, 2010;188(6):759-68. doi: 10.1083/jcb. 200910104. Epub Mar. 15, 2010.

Santini et al., A controlled-release microchip. Nature. Jan. 28, 1999;397(6717):335-8.

Schönbeck et al., Generation of biologically active IL-1 beta by matrix metalloproteinases: a novel caspase-1-independent pathway of IL-1 beta processing. J Immunol. Oct. 1, 1998;161(7):3340-6.

Shariat et al., Urine detection of survivin is a sensitive marker for the noninvasive diagnosis of bladder cancer. J Urol. Feb. 2004;171(2 Pt 1):626-30.

Smith et al., Rapid identification of highly active and selective substrates for stromelysin and matrilysin using bacteriophage peptide display libraries. J Biol Chem. Mar. 24, 1995;270(12):6440-9.

Suzuki et al., Matrix metalloproteinase-3 releases active heparin-binding EGF-like growth factor by cleavage at a specific juxtamembrane site. J Biol Chem. Dec. 12, 1997;272(50):31730-7.

Tascilar et al., Role of tumor markers and mutations in cells and pancreatic juice in the diagnosis of pancreatic cancer. Ann Oncol. 1999;10 Suppl 4:107-10.

Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].

Tockman et al., Considerations in bringing a cancer biomarker to clinical application. Cancer Res. May 1, 1992;52(9 Suppl):2711s-2718s.

Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011. 04.115. Epub May 3, 2011.

Tung et al., A novel near-infrared fluorescence sensor for detection of thrombin activation in blood. Chembiochem. Mar. 1, 2002;3(2-3):207-11.

Warren et al., Point-of-care diagnostics for noncommunicable diseases using synthetic urinary biomarkers and paper micro fluidics. Proc Natl Acad Sci U S A. Mar. 11, 2014;111(10):3671-6. doi:10. 1073/pnas.1314651111. Epub Feb. 24, 2014.

Weissleder et al., In vivo imaging of tumors with protease-activated near-infrared fluorescent probes. Nat Biotechnol. Apr. 1999;17(4):375-8.

Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.

Welser et al., Protease sensing with nanoparticle based platforms. Analyst. Jan. 7, 2011;136(1):29-41. doi: 10.1039/c0an00429d. Epub Sep. 28, 2010.

Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.

Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.

Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie. 201205721. Epub Oct. 18, 2012.

Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.

Yager et al., Point-of-care diagnostics for global health. Annu Rev Biomed Eng. 2008; 10:107-44. doi: 10.1146/annurev.bioeng.10. 061807.160524.

Yi et al., Cell surface-localized matrix metalloproteinase-9 proteolytically activates TGF-beta and promotes tumor invasion and angiogenesis. Genes Dev. Jan. 15, 2000;14(2):163-76.

(56) References Cited

OTHER PUBLICATIONS

Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zieske, A perspective on the use of iTRAQ reagent technology for protein complex and profiling studies. J Exp Bot. 2006;57(7):1501-8. Epub Mar. 30, 2006.
U.S. Appl. No. 17/091,075, filed Nov. 6, 2020, Bhatia et al.
U.S. Appl. No. 17/124,999, filed Dec. 17, 2020, Bhatia et al.
EP 12757730.2, Apr. 17, 2015, Extended European Search Report.
Amstad et al., Photo- and thermoresponsive polymersomes for triggered release. Angew Chem Int Ed. 2012;51:1-6.
Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.
Bartlett, Diagnostic tests for agents of community-acquired pneumonia. Clin Infect Dis. May 2011;52 Suppl 4:S296-304. doi: 10.1093/cid/cir045.
Bascom et al., Use of Enzyme Tests in Characterization and Identification of Aerobic and Facultatively Anaerobic Gram-Positive Cocci. Clin Microbiol Rev. Apr. 1998; 11(2): 318-340.
Berger, Helicobacter pylori breath tests. BMJ. 2002;324:1263.
Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.
Buss et al., Protease activity sensors noninvasively classify bacterial infections and antibiotic responses. EBioMedicine. Dec. 2018;38:248-56. doi:10.1016/j.ebiom.2018.11.031.
Caliendo et al., Better Tests, Better Care: Improved Diagnostics for Infectious Diseases. Clin Infect Dis. Dec. 2013;57(3):S139-S170.
Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.
Cheng et al., Multifunctional nanoparticles: Cost versus benefit of adding targeting and imaging capabilities. Sci. Nov. 16, 2012;338(6109):903-10.
Cheng et al., Ultrasensitive scanometric strategy for detection of matrix metalloproteinases using a histidine tagged peptide—Au nanoparticle probe. Chem Commun. 2011;47:2877-9.
Coelho et al., Usefulness of C-reactive protein in monitoring the severe community-acquired pneumonia clinical course. Crit Care. Aug. 2007; 11(4):R92.
Dennis et al., Albumin binding as a general strategy for improving the pharmacokinetics ofproteins. J Biol Chem. Sep. 20, 2002;277(38):35035-43. Epub Jul. 15, 2002.
Deshpande et al., Current trends in the use of liposomes for tumor targeting. Nanomedicine (Lond). Sep. 2013;8(9):1509-28. doi:10.2217/nnm.13.118.
Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 2, 2018.
Dudani et al., Harnessing Protease Activity to Improve Cancer Care. Ann Rev Cancer Biol. Mar. 2018;2:353-376.
Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.
Dudani et al., Sustained-release synthetic substrates for monitoring thrombosis and inflammation using point-of-care compatible readouts. Adv Funct Mater. May 3, 2016;26(17):2919-2928. doi: 10.1002/adfm.201505142. Epub Mar. 22, 2016.
El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.
Elegbede et al., Mechanistic studies of the triggered release of liposomal contents by matrix metalloproteinase-9. J Am Chem Soc. Aug. 13, 2008; 130(32):10633-42. doi: 10.1021/ja801548g. Epub Jul. 22, 2008.
Elston et al., New continuous and specific fluorometric assays for Pseudomonas aeruginosa elastase and LasA protease. Anal Biochem. Sep. 2007;368(1):87-94.
Figueiredo et al., Near infrared thoracoscopy of tumoral protease activity for improved detection of peripheral lung cancer. Int J Cancer. Jun. 2006;118(11):2672-7. doi: 10.1002/ijc.21713.
Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.
Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.
Ghoshal et al., How to Interpret Hydrogen Breath Tests. J Neurogastroenterol Motil. 2011;17:312-7.
Guimaraes et al., Site-specific C-terminal internal loop labeling of proteins using sortase-mediated reactions. Nat Protoc. 2013;8:1787-99.
Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.
Harris et al., Protease-triggered unveiling of bioactive nanoparticles. Small. 2008;4(9):1307-12. doi: 10.1002/smll.200701319. Epub Aug. 8, 2008.
Haskins, The application of stable isotopes in biomedical research. Biomed Mass Spectrom. Jul. 1982;9(7):269-77.
Holliday et al., Rapid Identification of *Staphylococcus aureus* by Using Fluorescent Staphylocoagulase Assays. J Clin Microbiol. Apr. 1999;37(4):1190-2.
Janzen et al., Colorimetric sensor arrays for volatile organic compounds. Anal Chem. Jun. 1, 2006;78(11):3591-600.
Jiang et al., Tumor imaging by means of proteolytic activation of cell-penetrating peptides. Proc. Natl. Acad. Sci. U. S. A. 2004;101:17867-17872.
Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.
Kalinska et al., Substrate specificity of *Staphylococcus aureus* cysteine proteases—Staphopains A, B and C. Biochimie. Feb. 2012;94(2):318-27. doi: 10.1016/j.biochi.2011.07.020. Epub Jul. 23, 2011.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Kirkpatrick et al., Noninvasive lung cancer detection via pulmonary protease profiling. bioRxiv. 36 pages. doi: https://doi.org/10.1101/495259, (Dec. 2018).
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.
Kwak et al., Volatile disease biomarkers in breath: a critique. Curr Pharm Biotechnol; 2011;12:1067-74.
Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.
Liou et al., Nonisotropic Enzyme-Inhibitor Interactions: A Novel Nonoxidative Mechanism for Quantum Proteolysis by Human Neutrophils. Biochem. 1995;34(49):16171-7.

(56) References Cited

OTHER PUBLICATIONS

Liu et al., Structure-based programming of lymph-node targeting in molecular vaccines. Nature. Mar. 27, 2014;507(7493):519-22. doi: 10.1038/nature12978. Epub Feb. 16, 2014.
Matsumoto et al., Role of bacterial proteases in pseudomonal and serratial keratitis. Biol Chem. Jan. 2004;385(11):1007-16.
McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.
McLennan et al., Subcutaneous drug delivery and the role of the lymphatics. Drug Discov Today Technol. 2005 Spring;2(1):89-96. doi:10.1016/j.ddtec.2005.05.006.
Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.
Morihara, Pseudolysin and other pathogen endopeptidases of thermolysin family. Methods in Enzymol. 1995;248:242-53.
Nouh et al., Cathepsin B: a potential prognostic marker for inflammatory breast cancer. J Transl Med. 2011;9(1):8 pages.
Olson et al., In vivo characterization of activatable cell penetrating peptides for targeting protease activity in cancer. Integr Biol (Camb). Jun. 2009; 1(5-6):382-93.
Parks et al., Matrix metalloproteinases as modulators of inflammation and innate immunity. Nat Rev Immunol. Aug. 2004;4(8):617-29.
Patton et al., Inhaling medicines: delivering drugs to the body through the lungs. Nat Rev Drug Discov. Jan. 2007;6(1):67-74.
Patton et al., The lungs as a portal of entry for systemic drug delivery. Proc Am Thorac Soc. 2004;1(4):338-44.
Phillips et al., Variation in volatile organic compounds in the breath of normal humans. J Chromatogr B. 1999;729:75-88.
Potempa et al., Corruption of innate immunity by bacterial proteases. J Innate Immun. 2009;1(2):70-87.
Prensner et al., Beyond PSA: the next generation of prostate cancer biomarkers. Sci Transl Med. Mar. 28, 2012;4(127):127rv3. doi:10.1126/scitranslmed.3003180.
Rousalova et al., Granzyme B-induced apoptosis in cancer cells and its regulation (review). Int J Oncol. Dec. 2010;37(6):1361-78. doi: 10.3892/ijo_00000788. PMID: 21042704.
Roy et al., Matrix metalloproteinases as novel biomarkers and potential therapeutic targets in human cancer. J Clin Oncol. 2009;27:5287-97.
Sawyers, The cancer biomarker problem. Nature. Apr. 3, 2008;452(7187):548-52. doi: 10.1038/nature06913.
Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.
Shaw et al., The role and regulation of the extracellular proteases of *Staphylococcus aureus*. Microbiol. Jan. 2004;150:217-28. doi: 10.1099/mic.0.26634-0.
Shibuya et al., Pseudomonas aeruginosa alkaline proteinase might share a biological function with plasmin. Biochim Biophys Acta. Apr. 29, 1991; 1077(3):316-24.
Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.
Sugahara et al., Coadministration of a tumor-penetrating peptide enhances the efficacy of cancer drugs. Science. May 21, 2010;328(5981):1031-5. doi:10.1126/science.H83057. Epub Apr. 8, 2010.
Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.
Taylor et al., Integrative genomic profiling of human prostate cancer. Cancer Cell. Jul. 13, 2010;18(1):11-22. doi:10.1016/j.ccr.2010.05.026. Epub Jun. 24, 2010.

Thorek et al., Internalization of secreted antigen-targeted antibodies by the neonatal Fc receptor for precision imaging of the androgen receptor axis. Sci Transl Med. Nov. 30, 2016;8(367):367ra167.
Trapani et al., Killing by cytotoxic T cells and natural killer cells: multiple granule serine proteases as initiators of DNA fragmentation. Immunol Cell Biol. 1993;71(3):201-8.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.
Vessillier et al., Hydrolysis of glycine-containing elastin pentapeptides by LasA, a metalloelastase from Pseudomonas aeruginosa. Eur J Biochem. Feb. 2001;268(4):1049-57.
Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.
Wilson et al., Applications and Advances in Electronic-Nose Technologies. Sensors (Basel). 2009;9(7):5099-148. doi: 10.3390/s90705099. Epub Jun. 29, 2009.
Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.
Wu et al., Expression and clinical significance of matrix metalloproteinase-9 in lymphatic invasiveness and metastasis of breast cancer. Plos One. 2014;9(5):e97804.
Xia et al., Multiplex detection of protease activity with quantum dot nanosenors prepared by Intein-Mediated specific bioconjugation. Analytical Chemistry. Nov. 15, 2008; 22(80) 8649-8655.
Zhu et al., Detecting bacterial lung infections: in vivo evaluation of in vitro volatile fingerprints. J Breath Res. Jan. 10, 2013;7(1):016003, 7 pages.
Chen et al., CRISPR-Cas12a target binding unleashes indiscriminate single-stranded DNase activity. Sciences. Apr. 27, 2018;360(6387):436-439. doi: 10.1126/science.aar6245. Epub Feb. 15, 2018. Erratum in: Science. Feb. 19, 2021;371(6531): doi:10-1126/science.abh0317.
Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.
Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.
Gatter et al., Transferrin receptors in human tissues: their distibution and possible clinical relevance. J Clin Pathol. May 1983;36(5):539-45. doi: 10.1136/jcp.36.5.539. PMID: 6302135; PMCID: PMC498283.
Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.
Hao et al., CRISPR-Cas-amplified urine biomarkers for multiplexed and portable cancer diagnostics. bioRxiv Jun. 17, 2020.
Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.
Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.
Parker et al., Folate receptor expression in carcinomas and normal tissues determined by a quantitative radioligand binding assay. Anal Biochem. Mar. 15, 2005;338(2):284-93. doi: 10.1016/j.ab.2004.12.026. PMID: 15745749.
Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.
Rashidian et al., Predicting the response to CTLA-4 blockade by longitudinal noninvasive monitoring of CD8 T cells. J Exp Med.

(56) References Cited

OTHER PUBLICATIONS

Aug. 7, 2017;214(8):2243-2255. doi: 10.1084/jem.20161950. Epub Jun. 30, 2017. PMID: 28666979; PMCID: PMC5551571.

Soleimany et al., Activity-Based Diagnostics: An Emerging Paradigm for Disease Detection and Monitoring. Trends Mol Med. May 2020;26(5):450-468. doi: 10.1016/j.molmed.2020.01.013. Epub Apr. 5, 2020. PMID: 32359477; PMCID: PMC8290463.

Sun et al., A PET imaging approach for determining EGFR mutation status for improved lung cancer patient management. Sci Transl Med. Mar. 7, 2018;10(431):eaan8840. doi: 10.1126/scitranslmed.aan8840. PMID: 29515002.

Weerakkody et al., Family of pH (low) insertion peptides for tumor targeting. Proc Natl Acad Sci U S A. Apr. 9, 2013;110(15):5834-9. doi: 10.1073/pnas.103708110. Epub Mar. 25, 2013. PMID: 23530249; PMCID: PMC3625278.

Yoo et al., 2'-0-methyl-modified phosphorothioate antisense oligonucleotides have reduced non-specific effects in vitro. Nucleic Acids Res. Apr. 2, 2004;32(6):2008-16. doi: 10.1093/nar/gkh516. PMID: 15064360; PMCID: PMC390367.

Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.

Extended European Search Report for Application No. EP 21172148.5 dated Jan. 10, 2022.

[No. Author Listed], Amidase Protein Classification Interpro. 2021. 2 pages.

[No. Author Listed], Emboss Needle Sequence Alignment. 2021. 2 pages.

Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.

Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012. PMID: 23256727; PMCID: PMC3557858.

\* cited by examiner

FIG. 6
I. Photo-caged reporter-substrate tandem peptides
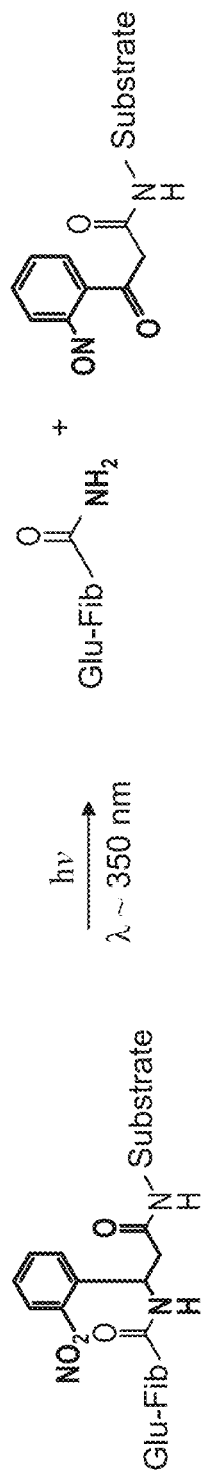
II. Photochemical cleavage monitored by LC MS
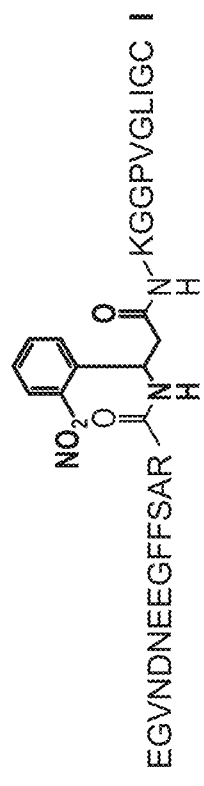
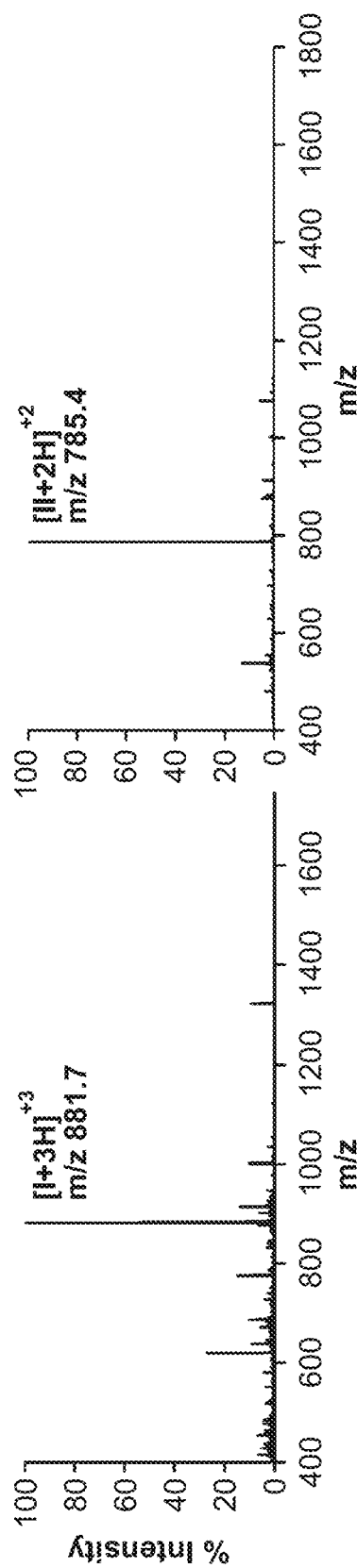

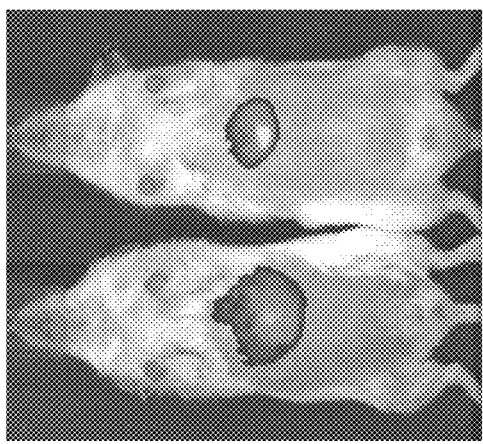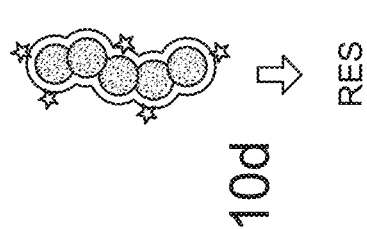
FIG. 10d
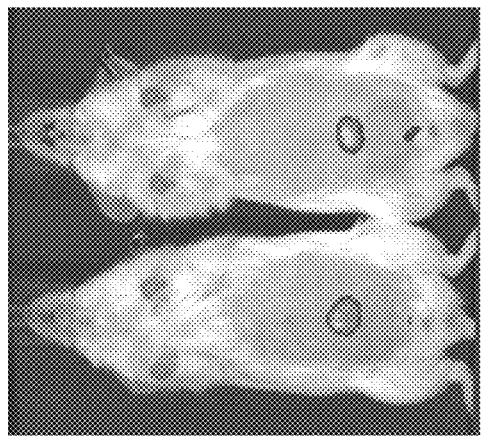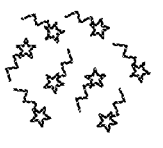
FIG. 10c
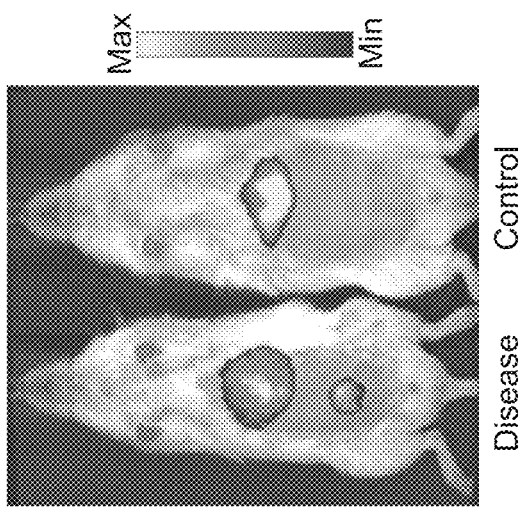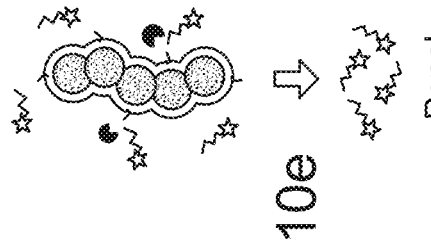
FIG. 10e

DAPI MMP9

DAPI DQ-Gelatin

FIG. 13b
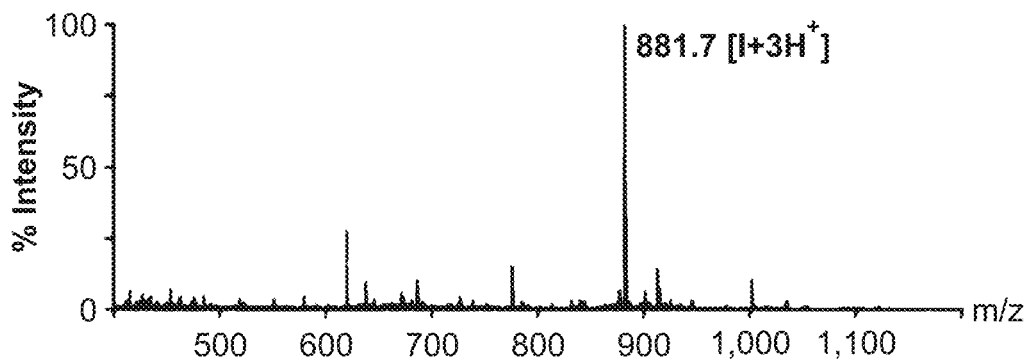
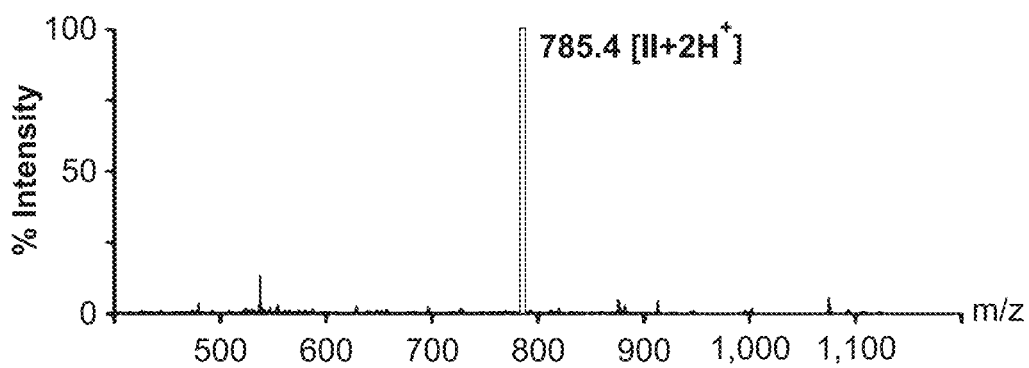
FIG. 13c
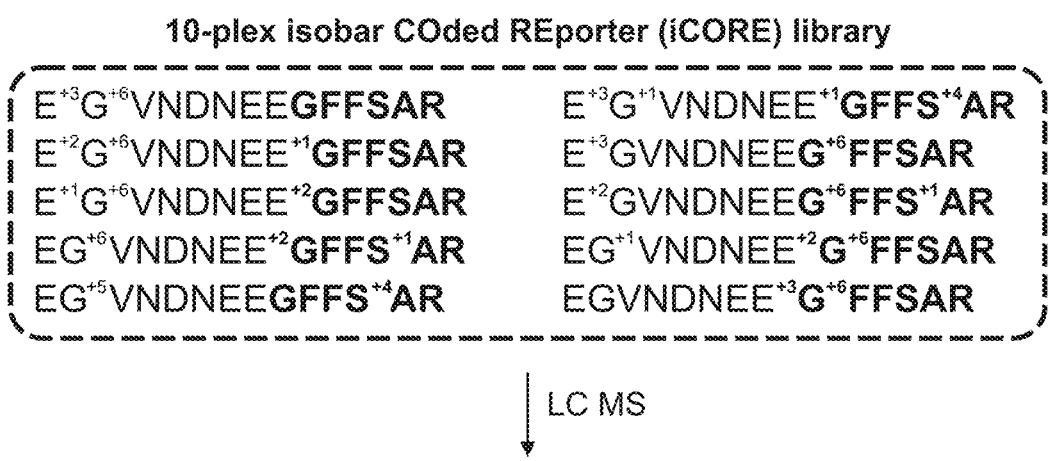

LC MS/MS

FIG. 13f
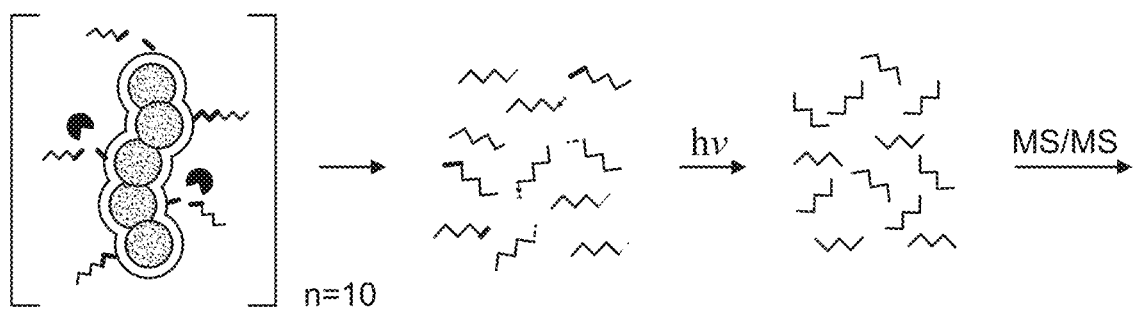
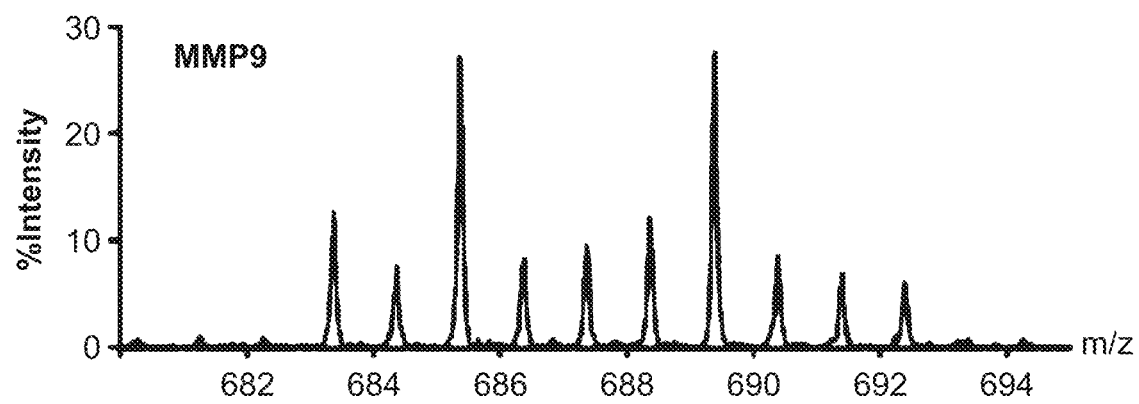

FIG. 14b

| Balance Reporter (y₆ ion) | [X+H⁺] mass (Da) | | |
|---|---|---|---|
| | Balance | Reporter | Total |
| E⁺³G⁺⁶VNDNEE-GFFSAR | 895.3 | 683.3 | 1578.7 |
| E⁺²G⁺⁶VNDNEE-⁺¹GFFSAR | 894.3 | 684.3 | 1578.7 |
| E⁺¹G⁺⁶VNDNEE-⁺²GFFSAR | 893.3 | 685.3 | 1578.7 |
| EG⁺⁶VNDNEE-⁺²GFFS⁺¹AR | 892.3 | 686.3 | 1578.7 |
| EG⁺⁵VNDNEE-GFFS⁺⁴AR | 891.3 | 687.3 | 1578.7 |
| E⁺³G⁺¹VNDNEE-⁺¹GFFS⁺⁴AR | 890.3 | 688.3 | 1578.7 |
| E⁺³GVNDNEE-G⁺⁶FFSAR | 889.3 | 689.3 | 1578.7 |
| E⁺²GVNDNEE-G⁺⁶FFS⁺¹AR | 888.3 | 690.3 | 1578.7 |
| EG⁺¹VNDNEE-⁺²G⁺⁶FFSAR | 887.3 | 691.3 | 1578.7 |
| EGVNDNEE-⁺³G⁺⁶FFSAR | 886.3 | 692.3 | 1578.7 |

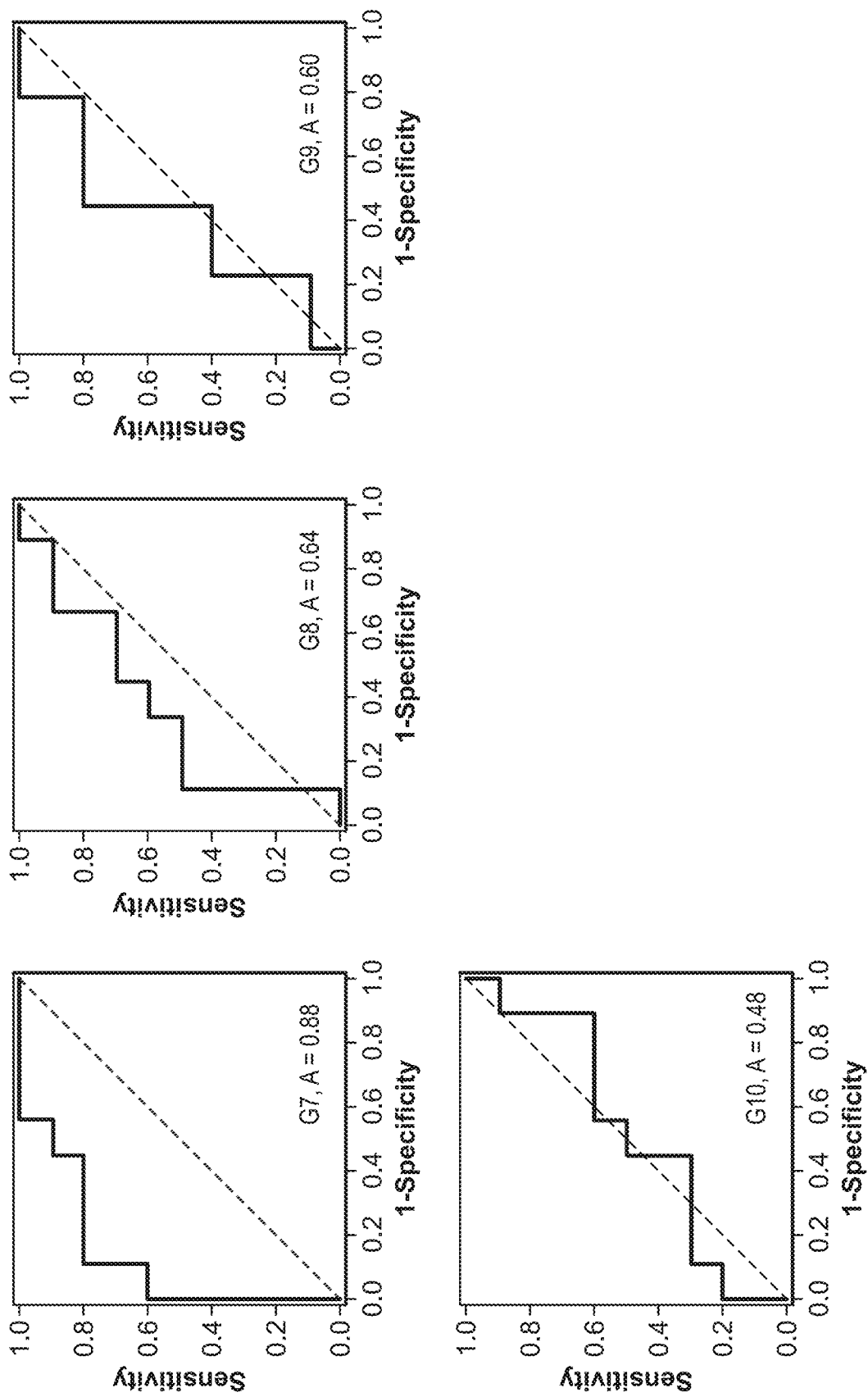

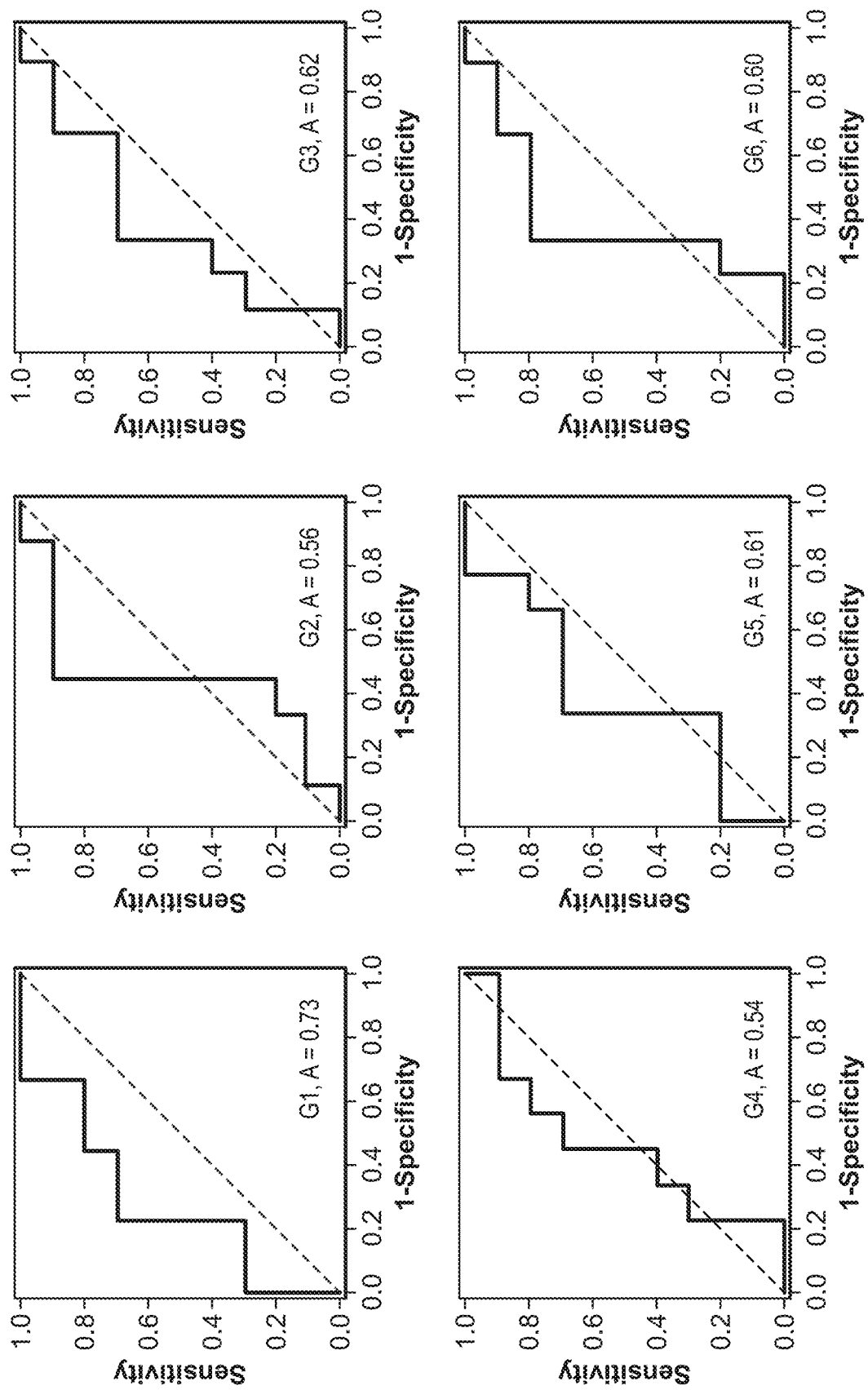

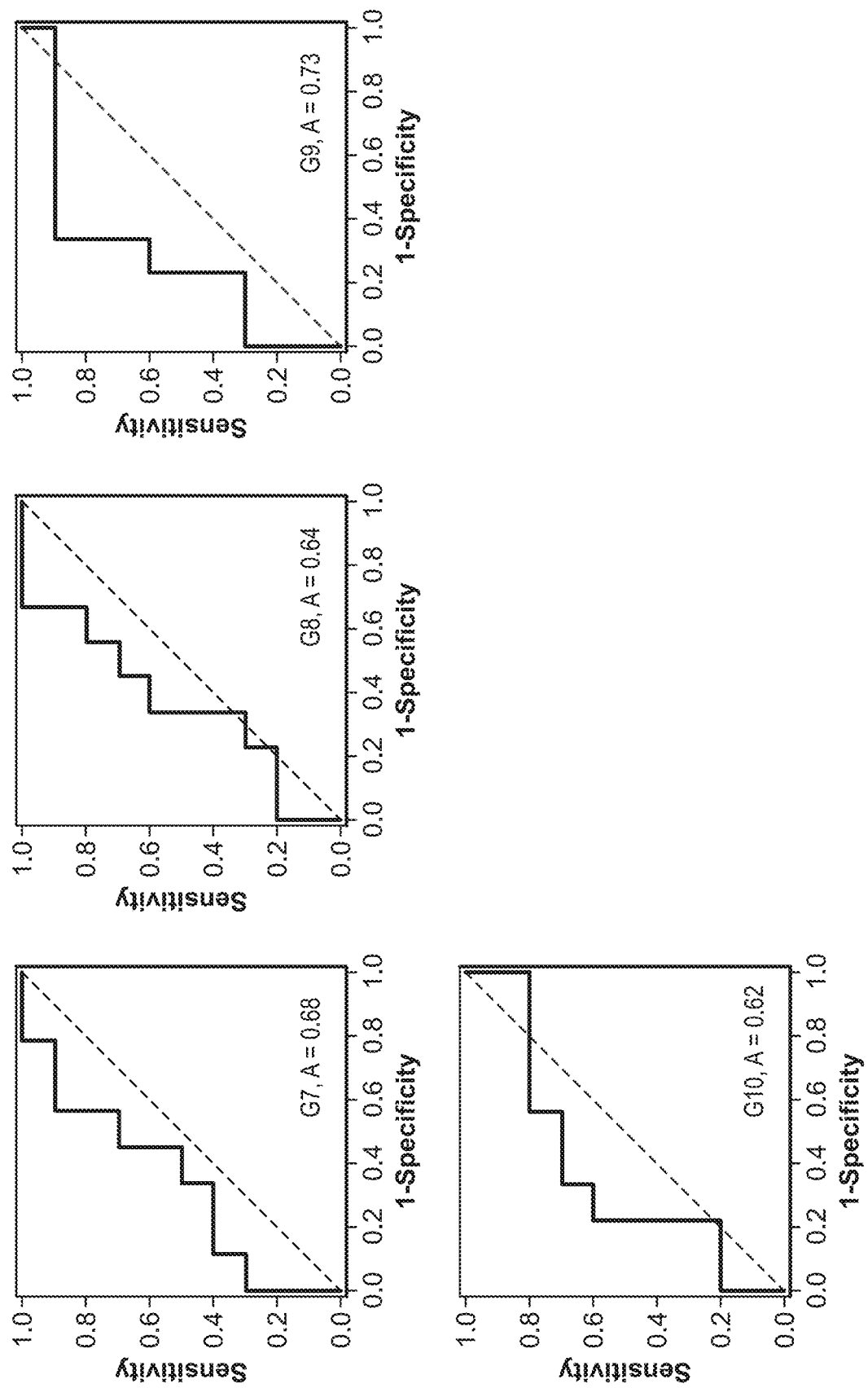

SEQUENCE LISTING

```
<160> NUMBER OF SEQ ID NOS: 37

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: May be isotope E+3, E+2 or E+1
<220> FEATURE:
<221> NAME/KEY: MISC_FEATURE
<222> LOCATION: (2)..(2)
<223> OTHER INFORMATION: May be isotope G+6
<220> FEATURE:
<221> NAME/KEY: MISC_FEATURE
<222> LOCATION: (8)..(8)
<223> OTHER INFORMATION: May be isotope E+1 or E+2

<400> SEQUENCE: 1

Glu Gly Val Asn Asp Asn Glu Glu Gly Phe Phe Ser Ala Arg
```

```
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Lys Gly Gly Pro Val Gly Leu Ile Gly Cys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Lys Gly Gly Pro Trp Gly Ile Trp Gly Gln Gly Gly Cys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Gly Phe Phe Ser Ala Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 5

Glu Gly Val Asn Asp Asn Glu Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Glu Gly Phe Phe Ser Ala Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Glu Gly Val Asn Asp Asn Glu
1               5
```

```
<210> SEQ ID NO 8
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+3
<220> FEATURE:
<221> NAME/KEY: MISC_FEATURE
<222> LOCATION: (2)..(2)
<223> OTHER INFORMATION: Isotope G+6
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 8

Glu Gly Val Asn Asp Asn Glu Glu Gly Phe Phe Ser Ala Arg Lys Gly
1               5                   10                  15

Gly Pro Gln Gly Ile Trp Gly Gln
            20

<210> SEQ ID NO 9
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+2
<220> FEATURE:
<221> NAME/KEY: MISC_FEATURE
<222> LOCATION: (2)..(2)
<223> OTHER INFORMATION: Isotope G+6
<220> FEATURE:
<221> NAME/KEY: MISC_FEATURE
<222> LOCATION: (4)..(8)
<223> OTHER INFORMATION: D-amino acid
<220> FEATURE:
<221> NAME/KEY: MISC_FEATURE
<222> LOCATION: (8)..(8)
<223> OTHER INFORMATION: Isotope E+1
<220> FEATURE:
<221> NAME/KEY: MISC_FEATURE
```

```
<222> LOCATION: (11)..(12)
<223> OTHER INFORMATION: D-amino acid
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 9

Glu Gly Val Asn Asp Asn Glu Glu Gly Phe Phe Ser Ala Arg Lys Gly
1               5                   10                  15

Gly Leu Val Pro Arg Gly Ser Gly
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+1
<220> FEATURE:
<221> NAME/KEY: MISC_FEATURE
<222> LOCATION: (2)..(2)
<223> OTHER INFORMATION: Isotope G+6
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (8)..(8)
<223> OTHER INFORMATION: Isotope E+2
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 10

Glu Gly Val Asn Asp Asn Glu Glu Gly Phe Phe Ser Ala Arg Lys Gly
1               5                   10                  15

Gly Pro Val Gly Leu Ile Gly
            20

<210> SEQ ID NO 11
```

<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: Isotope G+6
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (8)..(8)
<223> OTHER INFORMATION: Isotope E+2
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (12)..(12)
<223> OTHER INFORMATION: Isotope S+1
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 11

Glu Gly Val Asn Asp Asn Glu Glu Gly Phe Phe Ser Ala Arg Lys Gly
1               5                   10                  15

Gly Pro Trp Gly Ile Trp Gly Gln Gly
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: Isotope G+5
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (12)..(12)
<223> OTHER INFORMATION: Isotope S+4
<220> FEATURE:

```
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 12

Glu Gly Val Asn Asp Asn Glu Glu Gly Phe Phe Ser Ala Arg Lys Gly
1               5                   10                  15

Gly Pro Val Pro Leu Ser Leu Val Met
            20                  25

<210> SEQ ID NO 13
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+3
<220> FEATURE:
<221> NAME/KEY: MISC_FEATURE
<222> LOCATION: (2)..(2)
<223> OTHER INFORMATION: Isotope G+1
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (8)..(8)
<223> OTHER INFORMATION: Isotope E+1
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (12)..(12)
<223> OTHER INFORMATION: Isotope S+4
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 13

Glu Gly Val Asn Asp Asn Glu Glu Gly Phe Phe Ser Ala Arg Lys Gly
1               5                   10                  15

Gly Pro Leu Gly Leu Arg Ser Trp
            20
```

-continued

```
<210> SEQ ID NO 14
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+3
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (9)..(9)
<223> OTHER INFORMATION: Isotope G+6
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 14

Glu Gly Val Asn Asp Asn Glu Glu Gly Phe Phe Ser Ala Arg Lys Gly
1               5                   10                  15

Gly Pro Leu Gly Val Arg Gly Lys
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+2
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (9)..(9)
<223> OTHER INFORMATION: Isotope G+6
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (12)..(12)
<223> OTHER INFORMATION: Isotope S+1
```

```
-continued

<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modifed by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modifed by carboxyfluorescein
<220> FEATURE:
<221> NAME/KEY: MISC_FEATURE
<222> LOCATION: (18)..(18)
<223> OTHER INFORMATION: D-amino acid
<220> FEATURE:
<221> NAME/KEY: MISC_FEATURE
<222> LOCATION: (18)..(18)
<223> OTHER INFORMATION: Modifed by pipecolic acid

<400> SEQUENCE: 15

Glu Gly Val Asn Asp Asn Glu Glu Gly Phe Phe Ser Ala Arg Lys Gly
1               5                   10                  15

Gly Phe Arg Ser Gly Gly Gly
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Isotope E+1
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (8)..(8)
<223> OTHER INFORMATION: Isotope E+2
<220> FEATURE:
<221> NAME/KEY: MISC_FEATURE
<222> LOCATION: (9)..(9)
<223> OTHER INFORMATION: Isotope G+6
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein
<220> FEATURE:
<221> NAME/KEY: MISC_FEATURE
<222> LOCATION: (18)..(18)
<223> OTHER INFORMATION: D-amino acid
```

<400> SEQUENCE: 16

Glu Gly Val Asn Asp Asn Glu Glu Gly Phe Phe Ser Ala Arg Lys Gly
1               5                   10                  15

Gly Phe Pro Arg Ser Gly Gly Gly
            20

<210> SEQ ID NO 17
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(8)
<223> OTHER INFORMATION: D-amino acids
<220> FEATURE:
<221> NAME/KEY: MISC_FEATURE
<222> LOCATION: (8)..(8)
<223> OTHER INFORMATION: Isotope E+3
<220> FEATURE:
<221> NAME/KEY: MISC_FEATURE
<222> LOCATION: (9)..(9)
<223> OTHER INFORMATION: Isotope G+6
<220> FEATURE:
<221> NAME/KEY: MISC_FEATURE
<222> LOCATION: (11)..(12)
<223> OTHER INFORMATION: D-amino acids
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein
<220> FEATURE:
<221> NAME/KEY: MISC_FEATURE
<222> LOCATION: (18)..(18)
<223> OTHER INFORMATION: D-amino acid
<220> FEATURE:
<221> NAME/KEY: MISC_FEATURE
<222> LOCATION: (18)..(18)
<223> OTHER INFORMATION: Modified by pipecolic acid

<400> SEQUENCE: 17

Glu Gly Val Asn Asp Asn Glu Glu Gly Phe Phe Ser Ala Arg Lys Gly
1               5                   10                  15

Gly Phe Lys Ser Gly Gly Gly
            20

<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 18

Pro Gln Gly Ile Trp Gly Gln
1               5

```
<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Leu Val Pro Arg Gly Ser Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 20

Pro Val Gly Leu Ile Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 21

Pro Trp Gly Ile Trp Gly Gln Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 22

Pro Val Pro Leu Ser Leu Val Met
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Pro Leu Gly Leu Arg Ser Trp
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Pro Leu Gly Val Arg Gly Lys
1               5

<210> SEQ ID NO 25
```

```
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: May be D-amino acid
<220> FEATURE:
<221> NAME/KEY: MISC_FEATURE
<222> LOCATION: (1)..(1)
<223> OTHER INFORMATION: Modified by pipecolic acid

<400> SEQUENCE: 25

Phe Arg Ser Gly Gly Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: May be D-amino acid

<400> SEQUENCE: 26

Phe Pro Arg Ser Gly Gly Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: May be D-amino acid
<220> FEATURE:
<221> NAME/KEY: MISC_FEATURE
<222> LOCATION: (1)..(1)
<223> OTHER INFORMATION: Modified by pipecolic acid

<400> SEQUENCE: 27

Phe Lys Ser Gly Gly Gly
1               5

<210> SEQ ID NO 28
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 28

Glu Gly Val Asn Asp Asn Glu Glu Gly Phe Ser Ala Arg
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 29
```

```
Gly Phe Ser Ala Arg
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 30

Pro Pro Gly Phe Ser Pro Phe Arg
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

Asp Arg Val Tyr Ile His Pro Phe His Leu
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 32

Ser Tyr Ser Met Glu His Phe Arg Trp Gly Lys Pro Val Gly Lys Lys
1               5                   10                  15

Arg

<210> SEQ ID NO 33
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 33

Arg Pro Val Lys Val Tyr Pro Asn Gly Ala Glu Asp Glu Ser Ala Glu
1               5                   10                  15

Ala Phe Pro Leu Glu Phe
            20

<210> SEQ ID NO 34
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 34

Phe Arg Trp Gly Lys Pro Val Gly Lys Lys Arg Arg Pro Val Lys Val
1               5                   10                  15

Tyr Pro Asn Gly Ala Glu Asp Glu Ser Ala Glu Ala Phe Pro Leu Glu
            20                  25                  30

<210> SEQ ID NO 35
```

```
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: X is Norvaline (Nva)
<220> FEATURE:
<221> NAME/KEY: MISC_FEATURE
<222> LOCATION: (7)..(7)
<223> OTHER INFORMATION: Xaa is N - beta - (2,4 - dinitrophenyl) - L
      -alpha,beta-diaminopropionic acid (Dap)

<400> SEQUENCE: 35

Gly Gly Pro Leu Ala Xaa Xaa Ala Arg Gly Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: May be isotope G+1, G+2 or G+3
<220> FEATURE:
<221> NAME/KEY: MISC_FEATURE
<222> LOCATION: (3)..(3)
<223> OTHER INFORMATION: May be isotope V+1, V+5 or V+6
<220> FEATURE:
<221> NAME/KEY: MISC_FEATURE
<222> LOCATION: (4)..(4)
<223> OTHER INFORMATION: May be isotope N+6
<220> FEATURE:
<221> NAME/KEY: MISC_FEATURE
<222> LOCATION: (6)..(6)
<223> OTHER INFORMATION: May be isotope N+2 or N+6
<220> FEATURE:
<221> NAME/KEY: MISC_FEATURE
<222> LOCATION: (10)..(11)
<223> OTHER INFORMATION: May be isotope F+6 or F+10
<220> FEATURE:
<221> NAME/KEY: MISC_FEATURE
<222> LOCATION: (13)..(13)
<223> OTHER INFORMATION: May be isotope A+1 or A+4

<400> SEQUENCE: 36

Glu Gly Val Asn Asp Asn Glu Glu Gly Phe Phe Ser Ala Arg
1               5                   10

<210> SEQ ID NO 37
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: Isotope G+2 or G+3
<220> FEATURE:
<221> NAME/KEY: MISC_FEATURE
<222> LOCATION: (3)..(3)
<223> OTHER INFORMATION: Isotope V+6
<220> FEATURE:
<221> NAME/KEY: MISC_FEATURE
<222> LOCATION: (4)..(8)
```

```
<223> OTHER INFORMATION: D-amino acids
<220> FEATURE:
<221> NAME/KEY: MISC_FEATURE
<222> LOCATION: (12)..(12)
<223> OTHER INFORMATION: D-amino acid
<220> FEATURE:
<221> NAME/KEY: MISC_FEATURE
<222> LOCATION: (13)..(13)
<223> OTHER INFORMATION: May be isotope A+1
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MISC_FEATURE
<222> LOCATION: (14)..(15)
<223> OTHER INFORMATION: Modified by 3-amino-3-(2-nitrophenyl)propionic
      acid
<220> FEATURE:
<221> NAME/KEY: MISC_FEATURE
<222> LOCATION: (15)..(15)
<223> OTHER INFORMATION: Modified by carboxyfluorescein

<400> SEQUENCE: 37

Glu Gly Val Asn Asp Asn Glu Glu Gly Phe Phe Ser Ala Arg Lys Gly
1               5                   10                  15

Gly Cys
```

MULTIPLEXED DETECTION WITH ISOTOPE-CODED REPORTERS

RELATED APPLICATION

This Application claims the benefit under 35 U.S.C. § 120 of U.S. application Ser. No. 14/005,416, entitled "MULTIPLEXED DETECTION WITH ISOTOPE-CODED REPORTERS" filed on Jun. 12, 2014, which is a National Phase application under 35 U.S.C. § 371 of International Application No. PCT/US2012/029200, filed Mar. 15, 2012, which claims priority under 35 U.S.C. § 119(e) to U.S. Provisional Application Ser. No. 61/452,908, entitled "MULTIPLEXED DETECTION OF ANALYTES WITH ISOTOPE-CODED REPORTERS" filed on Mar. 15, 2011, which are herein incorporated by reference in their entirety.

GOVERNMENT SUPPORT

This invention was made with government support under Grant R01-CA124427 awarded by the National Institutes of Health. The U.S. government has certain rights in this invention.

REFERENCE TO A SEQUENCE LISTING SUBMITTED AS A TEXT FILE VIA EFS-WEB

This Application contains a Sequence Listing which has been submitted in ASCII format via EFS-Web and is hereby incorporated by reference in its entirety. Said ASCII copy, created on Feb. 14, 2022, is named M065670233US02-SUBSEQ-FL.txt and is 18,268 bytes in size.

BACKGROUND OF THE INVENTION

Mass spectrometry (MS) is an analytical technique that is useful for detecting analytes in both a quantitative and a qualitative way. During the MS process, detectable molecules, called mass tags, are ionized to generate charged molecules or molecule fragments and subsequently the mass-to-charge ratio of these molecules is measured.

MS is a highly versatile technology that can be used in various scenarios of analyte detection, for example, in biomedical diagnostics, and environmental analysis. For example, MS can be used to determine the presence or absence of an analyte, for example, a protein, nucleic acid, biomolecules, or small molecule compound, in a sample (for example, a biological sample), and/or to quantify an analyte in a sample.

While conventional MS assays are capable of detecting multiple analytes, e.g., peptides, simultaneously, quantitative analysis of multiple samples, e.g. from different individuals or time points, is currently limited to 4-plex, 6-plex, and 8-plex formats. Further, different analytes often have widely varying physiochemical properties, and, thus, MS properties, which results in similarly wide variability in sensitivity, specificity, and accuracy of MS based detection of different analytes. This variability in physiochemical properties of different analytes limits accurate simultaneous quantification of such different analytes in multiplex MS assays. The detection of multiple naturally-occurring or endogenous analytes, the chemical structures, of which often widely vary, also often necessitate monitoring a wide mass window in a single MS assay, which can be very time-intensive. Further, the detection of target analytes in complex samples, such as biological samples (e.g., blood, serum, or tissue biopsies), is often difficult and challenging without extensive prior front-end processing prior to MS assays.

SUMMARY OF THE INVENTION

Some aspects of this invention address the shortcomings of conventional MS technology by providing novel reagents and methods for the simultaneous detection of a virtually unlimited number of analytes in a sample, for example, a complex biological sample (e.g., a blood or tissue sample obtained from a subject) using MS methodology.

In some embodiments, this invention provides isotope coded reporter molecules, referred to herein as iCOREs, which are useful as mass tags in multiplexed MS based analyte detection. In some embodiments, sets, or libraries of iCOREs are provided that are useful in multiplexed detection of a virtually unlimited number of analytes in a sample. In some embodiments, the iCOREs in such a set or library are isobaric and different iCOREs within such a set or library are distinguished by their unique fragmentation ion signature. In some embodiments, different fragmentation signatures are conferred to different iCOREs by differential isotope labeling. For example, in some embodiments, this invention provides a set or library of iCOREs, e.g., a set of isobaric, isotope-labeled, peptide mass tags, that are useful in the multiplexed MS based analyte detection methods provided herein. Methods for the use of iCOREs and sets or libraries of iCOREs are also provided herein.

Some aspects of this invention provide reagents and methods that are useful for the translation of a parameter, for example, the presence of a target analyte in a sample, the presence of a target activity in a sample, or the identity of a sample, cell, or tissue, into an iCORE for MS detection, allowing for biochemical encoding of the parameter. For example, in some embodiments, this invention provides reagents and methods for the simultaneous translation, or biochemical encoding, of a plurality of analytes, for example, analytes of varying a chemical structure, in a complex sample (e.g., a blood or tissue sample obtained from a subject) into a plurality of iCOREs, for example, a plurality of isobaric, isotope-labeled, peptide mass tags, so that each analyte is represented by a different iCORE having a characteristic fragmentation signature. Accordingly, each analyte can be identified by detecting the fragmentation signature associated with the specific iCORE encoding the analyte, for example, in an MS/MS assay. To give another example, in some embodiments, this invention provides reagents and methods for the simultaneous translation, or biochemical encoding, of a plurality of biological activities, for example, enzymatic activities (e.g., protease, kinase, or phosphatase activities), in a complex sample (e.g., a blood or tissue sample obtained from a subject) into a plurality of iCOREs, for example, a plurality of isobaric, isotope-labeled, peptide mass tags, so that each activity is represented by a different iCORE having a characteristic fragmentation signature. Accordingly, each activity can be identified by detecting the fragmentation signature associated with the specific iCORE encoding the activity, for example, in an MS/MS assay.

Each of the embodiments of the invention can encompass various recitations made herein. It is, therefore, anticipated that each of the recitations of the invention involving any one element or combinations of elements can, optionally, be included in each aspect of the invention. Similarly, each aspect or embodiment of the invention can be excluded from any other aspect or embodiment, or any combination of aspects or embodiments of the invention.

BRIEF DESCRIPTION OF THE DRAWINGS

FIG. 6. Photocleavage and photocleavage efficiency. EGVNDNEEGFFSAR corresponds to SEQ ID NO: 1. KGGPVGLIGC corresponds to SEQ ID NO: 2.

FIGS. 10A-10E. Selecting protease-sensitive substrates for NW-chaperoned urinary trafficking.

FIGS. 13A-13F. Photo-caged iCORE libraries for multiplexed profiling of protease activities by LC MS/MS. EGVNDNEEGFFSAR corresponds to SEQ ID NO: 1. KGGPWGIWGQGGC corresponds to SEQ ID NO: 3.

FIGS. 14A-14B. Isobaric COded REporter (iCORE) mass encoding. EGVNDNEEGFFSAR corresponds to SEQ ID NO: 1.

FIGS. 20A-20B. ROC curves of fibrosing biomarkers.

FIGS. 21A-21B. ROC curves of resolving biomarkers.

DEFINITIONS

Figure 1A:
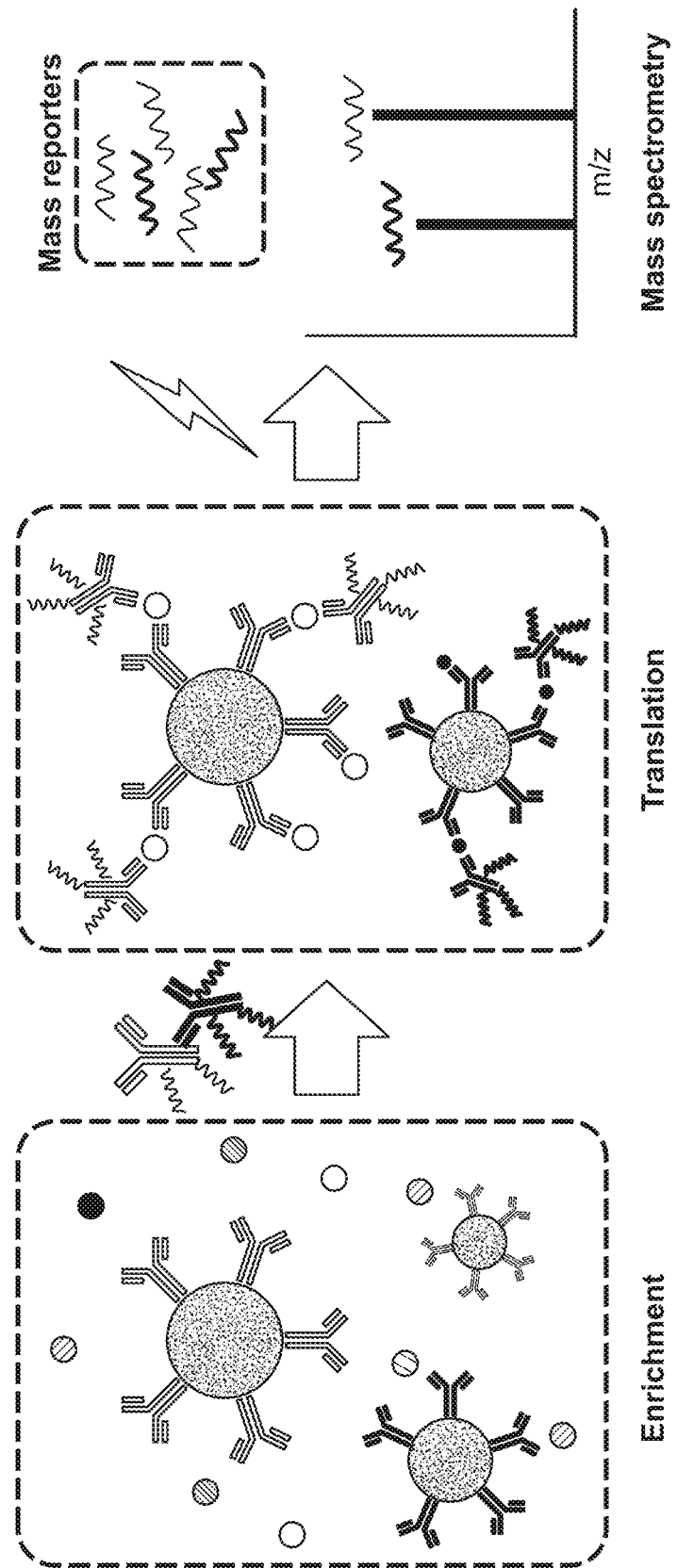
FIGS. 1A-1B. Schematic of an exemplary method for multiplexed translational analyte detection. The displayed method includes an optional enrichment step.

The term activity, as used herein, refers to a biological activity. The term includes, in some embodiments, enzyme activity, for example, hydrolase, transferase, lyase, isomerase, ligase, or oxidoreductase activity. In some embodiments, the activity is a protease activity. In some embodiments, the activity is a phosphatase activity. In some embodiments, the activity is a kinase activity. Enzymatic activity can be encoded in iCOREs, for example, by providing a substrate of the target enzyme comprised in an iCORE, exposing the iCORE to a sample comprising the enzyme, and detecting the enzyme-modified substrate, for example, by methods described herein. Typically, an iCORE for encoding an enzyme activity comprises a target substrate of that enzyme (e.g., a protease recognition site, or a phosphorylation site, etc.), and the modification of the target site by the enzyme (e.g., cleavage, phosphorylation or de-phosphorylation) can be detected, for example, by methods described herein.

The term analyte, as used herein, refers to a molecule the presence or absence or the quantity of which is subject to analysis. Typically, an analyte is a molecule of interest, for example, a protein or peptide, a nucleic acid molecule, a carbohydrate, a lipid, a metabolite, a small organic molecule, a drug, or a drug derivative (e.g. a drug metabolite), a cell surface marker, or a secreted molecule, the detection or quantification of which is of interest to a researcher or clinician, for example, for research or diagnostic purposes. A target analyte is an analyte the presence, absence, or the quantity of which in a sample, for example, in a biological, experimental, or environmental sample is subject to analysis. An analyte may be a biomarker, for example, a biomarker the presence, absence, or quantity of which in a sample indicates a particular condition of the sample or the subject, experiment, or environment the sample was obtained from. In some embodiments, an analyte is a biomedical biomarker, for example, a protein, peptide, polysaccharide, small molecule, or metabolite in a sample obtained from a subject diagnosed with or suspected to have a disease or condition, wherein the presence, absence, or quantity of the biomarker in the sample is indicative of the presence, absence, or state of the disease or condition in the subject. For example, in some embodiments, a diagnostic assay provided herein comprises the detection of a panel of protein and metabolite biomarkers the presence, absence, or quantity of which in a blood or serum sample obtained from a subject is indicative of the presence, absence, or state of a cancer, or a plurality of cancers in the subject. The protein and metabolite biomarkers investigated in such an assay would be the target analytes of that assay.

The term antibody, as used herein, refers to an immunoglobulin, whether natural or wholly or partially synthetically produced. Antibody derivatives which maintain specific binding ability, for example, antigen-binding antibody fragments, such as Fab, Fab', or F(ab')2 fragments, or engineered antibodies, such as scFvs, are also included referred to by the term antibody. The term also refers to any protein having a binding domain which is homologous or largely homologous to an immunoglobulin binding domain. These proteins may be derived from natural sources, or partly or wholly synthetically produced. An antibody may be monoclonal or polyclonal. An antibody may be a member of any immunoglobulin class, including, but not limited to, any of the human classes: IgG, IgM, IgA, IgD, and IgE.

The term antibody fragment, as used herein, refers to any derivative of an antibody which is less than full-length. Preferably, the antibody fragment retains at least a significant portion of the full-length antibody's specific binding ability. Examples of antibody fragments include, but are not limited to, Fab, Fab', F(ab')2, scFv, Fv, dsFv, diabody, single variable domain, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids. Single-chain Fvs (scFvs) are recombinant antibody fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. Diabodies are dimeric scFvs. The components of diabodies typically have shorter peptide linkers than most scFvs, and they show a preference for associating as dimers. An Fv fragment is an antibody fragment which consists of one VH and one VL domain held together by non-covalent interactions. The term dsFv is used herein to refer to an Fv with an engineered intermolecular disulfide bond to stabilize the VH-VL pair. An F(ab')2 fragment is an antibody fragment essentially equivalent to that obtained from immunoglobulins (typically IgG) by digestion with an enzyme pepsin at pH 4.0-4.5. The fragment may be recombinantly produced. A Fab' fragment is an antibody fragment essentially equivalent to that obtained by reduction of the disulfide bridge or bridges joining the two heavy chain pieces in the F(ab')2 fragment. The Fab' fragment may be recombinantly produced. A Fab fragment is an antibody fragment essentially equivalent to that obtained by digestion of immunoglobulins (typically IgG) with the enzyme papain. The heavy chain segment of the Fab fragment is the Fd piece.

The term binding agent, as used herein, refers to a molecule that binds to another molecule with high affinity. In some embodiments, the binding is through non-covalent interaction. In some embodiments, the binding is specific, meaning that the binding agent binds only one particular type of molecule, or a narrow class of highly similar molecules with high affinity. Non-limiting examples of binding agents are antibodies, antibody fragments, aptamers, and adnectins.

The term body fluid, as used herein, refers to any body fluid including, without limitation, serum, plasma, lymph fluid, synovial fluid, follicular fluid, seminal fluid, amniotic fluid, mild, whole blood, sweat, urine, cerebrospinal fluid, saliva, semen, sputum, tears, perspiration, mucus, tissue culture medium, tissue extracts, and cellular extracts. It may also apply to fractions and dilutions of body fluids. The source of a body fluid can be a human body, an animal body, an experimental animal, a plant, or other organism.

The term conjugated, as used herein, refers to a state of relatively stable association between two entities, for example, between an iCORE and a binding agent. In some embodiments, conjugated entities are linked by a direct or indirect covalent or non-covalent interaction. Preferably, the association is via covalent bond. In some embodiments, two peptides are conjugated via protein fusion, e.g., a peptide iCORE as provided herein, may be conjugated to a peptidic binding agent, e.g., an antibody or antibody fragment, by fusing the iCORE to the binding agent, e.g., by expression of a recombinant iCORE-binding agent fusion protein. Non-covalent interactions that result in conjugation include, but are not limited to hydrogen bonding, van der Waals interactions, hydrophobic interactions, magnetic interactions, and electrostatic interactions. Typically, two conjugated entities are associated with each other in a manner stable enough to withstand the conditions typically encountered during an iCORE experiment, for example, an iCORE conjugated to a binding agent is associated with the binding agent in a manner sufficient for the bond between the two to endure the binding and washing steps typically comprised in the methods they are used in, for example, before the two entities are intentionally separated (e.g., by cleaving a linker connecting the iCORE to the binding agent).

The term enriched, as used herein, refers to a sample or composition in which the proportion of a material of interest in a mixture of materials comprising both the material of interest and at least one additional material is increased as compared to the original proportions in the sample. Such an increase can be achieved by methods of physical separation, chemical interaction or reaction, and other methods well known to those of skill in the art, or provided herein. For example, an original sample comprising a population of different iCOREs conjugated to different binding agents may be enriched to include predominantly those iCOREs conjugated to binding agents that bind to their specific target analytes by immobilizing the analyte-bound iCOREs on a solid support and washing away all or most of the unbound iCOREs. Isolation or purification are within the scope of the term, but such steps are not required in order to enrich a compound, e.g., a desired iCORE.

The term fragmentation signature, or fragmentation ion signature, as used herein, refers to the pattern of ions that an iCORE can fragment into, for example, during an MS assay, e.g., an MS/MS assay. In some embodiments, differential isotope labeling of iCOREs of the same base sequence, e.g., of the same amino acid sequence in the case of peptide iCOREs, is used to produce a set of different isobaric iCOREs, each of which produces at least one ion, for example, a $y_7$ ion, that can be distinguished from other ions of the same type, e.g., $y_7$ ions, produced by the other iCOREs of the set, e.g., in an MS assay, e.g. an MS/MS assay. For example, the ten exemplary iCOREs G1-G10 described in FIG. 3 each exhibit a unique fragmentation signature, each producing a different mass peak representing the $y_7$ fragment of the iCOREs in an MS/MS assay. A unique fragmentation signature is a signature of a given polymeric molecule that results in a unique fragmentation ion, for example, a unique $y_7$ fragmentation ion, which can be unambiguously identified, or which can be distinguished from any other fragmentation ion, e.g., any other $y_7$ ion produced by a library of iCOREs. In some embodiments, different fragmentation signatures are conferred to different iCOREs by differential isotope labeling. For example, in some embodiments, an isobaric iCORE library is produced by distributing heavy isotopes across the iCORE molecule, e.g., across the amino acid residues of a peptide iCORE, in a way that each different iCORE produces a reporter fragmentation ion (e.g., a $y_7$ ion) of a different mass, while the whole sequence, (e.g., the peptide sequence comprising the reporter and the balance) of all iCOREs is of the same mass.

The term iCORE, as used herein, refers to an isotope-coded reporter molecule that can be used as a mass tag in an MS assay, for example, an MS/MS assay. Typically, an iCORE is an isotope-labeled polymer, for example, a polypeptide, polynucleotide, or polysaccharide that comprises at least 5 monomeric residues, e.g. amino acid, nucleotide, or monosaccharide residues. In some embodiments, an iCORE comprises more than 5 monomeric residues. In some preferred embodiments, the structure of an iCORE allows for the generation of different fragmentation signatures, for example, by differential isotope labeling of a monomeric residue, or a combination of monomeric residues. In some embodiments, the polymer structure, e.g., the amino acid, nucleotide, or monosaccharide sequence of an iCORE allows for the generation of at least about 10 iCORE molecules, for example, isobaric iCORE molecules, having different fragmentation signatures that can be distinguished in an MS assay, e.g., an MS/MS assay. In some embodiments, the polymer structure allows for the generation of more than 10 different iCOREs having different fragmentation signatures.

The term isobaric, as used herein, refers to a group of molecules having the same molecular weight. For example, in some embodiments, a set of isobaric peptide iCOREs may be a set of peptides that all have the same weight, but different fragmentation signatures.

The term parameter, as used herein in the context of iCORE encoding, refers to a characteristic, feature, or measurable factor in a sample, for example, in a biological sample. In some embodiments, the term includes the presence, absence, or quantity of an analyte. In some embodiments, the term includes the presence, absence or quantity of a biological activity, for example, an enzymatic activity or a binding activity.

The term plurality, as used herein, refers to two or more of the elements so qualified.

The term polynucleotide, which is used herein interchangeably with the terms oligonucleotide and nucleic acid molecule herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term polypeptide is used herein interchangeably with the terms peptide, oligopeptide, and protein, and refers to a polymer of amino acid residues linked together by peptide bonds. The term, as used herein, refers to proteins, polypeptides, and peptides of any size, structure, or function. Typically, a polypeptide is at least three amino acids long. In some embodiments, polypeptides, for example, peptide iCOREs, comprise naturally-occurring amino acids, although non-naturally-occurring amino acids (e.g., compounds that do not occur in nature but that can be incorporated into a polypeptide chain and/or amino acid analogs as are known in the art may alternatively be employed. Also, one or more of the amino acids in an inventive polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide may be isotope-labeled. A peptide may comprise D-amino acids, L-amino acids, or a mixture of D-amino acids and L-amino acids. In some embodiments, a D-amino acid or a plurality of D-amino acids in a polypeptide confers increased protease resistance to the respective polypeptide as compared to a polypeptide of the same sequence but consisting of L-amino acids. A polypeptide may also be a single molecule or may be a multi-molecular complex. A polypeptide may be a fragment of a naturally occurring protein or peptide. A polypeptide may be naturally occurring, recombinant, or synthetic, or any combination of these.

The term polysaccharide, as used herein, refers to a polymer of sugars. Typically, a polysaccharide comprises at least two sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

The term sample, as used herein, refers to a composition of matter representative of a biological, clinical, or experimental environment. For example, a biological sample may be a sample obtained from a subject, such as a body fluid sample, or a cell or tissue sample, or to a sample obtained from an experimental environment, such as a composition comprising a small molecule compound, a cell culture supernatant, a composition comprising an engineered organ, and so forth. A complex sample is a sample comprising a plurality of different analytes and/or of non-analyte molecules in addition to an analyte. Non-limiting examples of complex samples are a serum sample, a blood sample, a urine sample, and a tissue sample. In some embodiments, a complex sample is a sample comprising such a large number of molecules (e.g. analytes or non-analyte molecules) that the detection of a single target analyte, for example, a peptide or metabolite, cannot readily be achieved by an MS/MS assay, for example, because of interference of other molecules with similar MS signatures. In some embodiments, a complex sample may require extensive front-end processing, for example, target analyte enrichment, to allow detection of a target analyte in a conventional MS assay.

The term small molecule, which is used herein interchangeably with the terms small molecule compound, and drug, refers to a compound either synthesized in the laboratory or found in nature, which is typically characterized in that it contains several carbon-carbon bonds, and has a molecular weight of less than 1500, although this characterization is not intended to be limiting for the purposes of the present invention. Examples of small molecules that occur in nature include, but are not limited to, taxol, dynemicin, and rapamycin. Examples of small molecules that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 1998, 120, 8565) and U.S. Pat. No. 7,109,377, entitled "Synthesis of Combinatorial Libraries of Compounds Reminiscent of Natural Products", the entire contents of which are incorporated herein by reference. In certain other preferred embodiments, natural-product-like small molecules are utilized.

The term subject, as used herein, refers to a human, a non-human primate, a non-human mammal (e.g., a cow, a horse, a pig, a sheep, a goat, a dog, a cat, or a rodent), a vertebrate, an arthropod, a chordate, an annelid, a mollusk, a nematode, an echinoderm. In some embodiments, a subject is a laboratory animal, e.g., a mouse, rat, cat, dog, pig, cow, hamster, gerbil, frog, fish, worm (e.g., *C. elegans*), or fly (e.g., fruit fly, *D. melanogaster*). In some embodiments, a subject is a microorganism, for example, a yeast, bacteria, or fungus. In some embodiments, for example, in some embodiments involving a clinical application of an aspect of this invention, the subject is diagnosed with or suspected to have a disease or condition.

DETAILED DESCRIPTION OF THE INVENTION

Some aspects of this invention provide methods and reagents for encoding a plurality of biological parameters, for example, the presence or absence of an analyte, or of an enzymatic activity in a sample, into mass-encoded reporters, termed iCOREs. This allows for, e.g., the multiplexed detection of analytes or enzymatic activities in complex biological samples. The exogenous reporters can be analyzed in a single assay, e.g., an MS/MS assay, thus avoiding the need for multiple assays of different types, as often required when assessing different analytes or enzymatic activities in biological samples using endogenous reporters.

The dependence on endogenous reporters to indicate disease in biological samples is a major limitation to diagnostic approaches. Herein, the development of iCOREs, exogenous mass-encoded reporters, as 'synthetic biomarkers' of disease is described. In some embodiments, iCOREs described herein are used for in vivo diagnostics. In some embodiments, iCOREs are designed to perform three functions in vivo (upon administration to a subject): target sites of disease, sample dysregulated protease activities, and emit mass-encoded reporters into host urine for multiplexed detection by mass spectrometry. To demonstrate exemplary applications of this technology, it was applied to a xenobiotic model of liver fibrosis as a noninvasive alternative to biopsy-based monitoring, and sensitive and specific synthetic biomarkers were identified that report on both actively fibrosing and resolving stages of liver disease. Different iCORE panels were also identified that markedly lowered the threshold for early cancer detection when compared with blood biomarkers in a mouse model of colorectal cancer. The ability to rapidly design, screen and identify iCOREs as synthetic biomarkers for precise, multiplexed monitoring of disease apart from endogenous biomarkers is broadly amenable to distinct pathophysiological processes, with additional applications in systems biology, drug development and point-of-care diagnostics.

Biomarker discovery is motivated by the desire to identify reliable indicators of disease for risk assessment, early detection, predicting patient responses to therapies, and surveillance of recurrent disease.[1,2] To date, a broad range of distinct biological species such as metabolites,[3] peptides,[4] proteins,[2,5] cell-free nucleic acids,[6] exosomes,[7] and circulating tumor cells,[8] have been developed into biomarkers with varying degrees of performance. However, the reliance on native components to indicate disease is limited by fundamental technical and biological challenges because biomarkers are frequently found in low levels in circulation,[8,9] are difficult to resolve in complex biological fluids,[10] and can be rapidly degraded both in vivo and ex vivo.[4,11]

An alternative to endogenous biomarkers is the systemic administration of exogenous reporter agents to interrogate biological states as described herein. These approaches offer the potential to tailor agents to exploit host physiology or interface with disease-specific molecular processes as alternative indicators of disease. Examples include the polysaccharide inulin to assess glomerulus filtration rates, FDG-PET to unveil regions of increased glucose metabolism, and a suite of molecular and activity-based probes for imaging biological activities in vivo.[12-14] Because these agents can be designed and tested in vitro and in preclinical models, they can be iteratively optimized and can be administered at concentrations significantly above biological background. The limitations with these approaches include the inability to monitor large family of probes simultaneously due to limited multiplexing capabilities and substantial infrastructure for in vivo analysis requiring patients to be on-site (e.g. PET, MRI) precluding remote data or sample collection.

Some aspects of this disclosure provide a framework for engineering nanoscale, isobaric mass-encoded reporter agents that passively accumulate in diseased tissues from host circulation via organ- or disease-specific vascular fenestrations (e.g. liver sinusoid endothelium or angiogenic tumor vessels respectively).[15,16] In an exemplary embodiment, iCOREs are provided that are designed to interrogate protease activity in tumor microenvironments. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease. Because dysregulated protease activities are implicated in a wide range of human diseases including cancer, fibrosis, atherosclerosis, inflammation, Alzheimer's and many others,[17] highly multiplexed monitoring of aberrant protease activities has the potential to distinguish diverse disease states through combinatorial analysis. While the methods and reagents provided herein are widely applicable to a wide variety of diseases, described herein is the exemplary application of this technology to address two unmet clinical challenges: the need for a noninvasive alternative to biopsy-based monitoring for liver fibrosis,[18] and the inability of current clinically-utilized blood biomarkers to reliably detect early stage cancers.[19]

Other exemplary parameters that can be encoded and measured with iCORE technology are analytes. Current tools for analyte detection include gel electrophoresis, western blot, ELISA, PCR, immunofluorescence, microarray, and MS-based platforms like MALDI and Liquid Chromatography-MS technologies, such as LC MS/MS. LC MS is an analytical chemistry technique that combines the physical separation capabilities of liquid chromatography (e.g., High Performance LC, HPLC) with the mass analysis capabilities of mass spectrometry. LC-MS has very high sensitivity and selectivity and is, thus broadly applicable to a variety of analytes, for example, to the specific detection and/or identification of analytes in the presence of other chemicals (e.g., in a complex biological, experimental, or environmental). MS/MS (or tandem MS) involves two or more steps of MS, with some form of fragmentation occurring in between the stages. MS/MS is a technique commonly used to identify sequence information, for example, sequence information of individual peptides. Modern mass spectrometers, in-line with extensive chromatographic fractionation, can detect and assess hundreds of analytes from a single sample. MS, however, is not without limitations. Current challenges associated with mass spectrometric analysis can be simplified into two major contributing factors.

First, many samples, for example, many biological samples (e.g., blood, serum, tissue (e.g., tumor) biopsy, cell lysate, urine, cerebral spinal fluid), experimental samples (e.g., samples of interest in combinatorial drug screens), and environmental samples (e.g., soil or water samples) containing or suspected to contain an analyte of interest are highly complex, comprising different types of analytes, e.g., biomolecules (e.g., proteins, nucleic acids, lipids, carbohydrates, metabolites), small molecules, drugs and drug metabolites, inorganic and organic matter, cells, or cell debris, which are present in concentrations spanning many orders of magnitude (e.g. pg/ml to mg/ml in blood). The task of finding and detecting target analytes within this such complex samples is difficult because of high background signal and more importantly, the suppression of target analyte ionization, an integral process for mass spectrometric analysis, by bystander molecules (e.g. lipids).

Second, many analytes themselves are difficult to detect reliably and robustly via MS base methods, or, for some analytes, any conventional method for that matter, because of their suboptimal physiochemical properties (e.g. mass, charge, hydrophilicity). Variability in physiochemical properties amongst analytes leads to poor experimental repeatability and high variance between assays. This is particularly relevant for protein quantification. Often, protein-comprising samples are digested with a protease, e.g., trypsin, prior to MS analysis, and typically, the majority of peptides produced from trypsin digests do not contain sequences that are optimal for MS analysis. Such peptides are not detected or only poorly detected in a typical MS experiment, resulting in gross under-sampling and decreased overall sensitivity of current MS assays.

To address these challenges, technologies and methodologies have focused on affinity enrichment of the target analyte prior to MS to increase signal intensity, selective depletion of high abundance biomolecules to reduce background, and targeted chemistries to isolate sub-proteomes (see, e.g., Anderson, N. L., Anderson, N. G., Haines, L. R., Hardie, D. B., Olafson, R. W., Pearson, T. W., 2004. *Mass spectrometric quantitation of peptides and proteins using Stable Isotope Standards and Capture by Anti-Peptide Antibodies* (SISCAPA). J. Proteome Res. 3, 235.; Whiteaker, J. R., Zhao, L., Zhang, H. Y., Feng, L. C., Piening, B. D., Anderson, L., Paulovich, A. G., 2007b. *Antibody-based enrichment of peptides on magnetic beads for mass-spectrometry-based quantification of serum biomarkers*. Anal. Biochem. 362, 44; Kuhn, E., Addona, T., Keshishian, H., Burgess, M., Mani, D. R., Lee, R. T., Sabatine, M. S., Gerszten, R. E., Carr, S. A., 2009. *Developing multiplexed assays for Troponin I and Interleukin-33 in plasma by peptide immunoaffinity enrichment and targeted mass spectrometry*. Clin. Chem. 55, 1108; Wollscheid B, Bausch-Fluck D, Henderson C, O'Brien R, Bibel M, Schiess R, Aebersold R, Watts J D., *Mass-spectrometric identification and relative quantification of N-linked cell surface glycoproteins*. Nat Biotechnol. 2009 April; 27(4):378-86.; Hui Zhang, Xiao-jun Li, Daniel B Martin, Ruedi Aebersold, *Identification and quantification of N-linked glycoproteins using hydrazide chemistry, stable isotope labeling and mass spectrometry*. Nature Biotechnology 21, 660-666 (2003); the entire contents of all of which are incorporated herein by reference). Some efforts have also been directed at developing computational algorithms to predict high-responding peptides from a given protein, and to reduce the resources required to develop robust proteomic assays (see, e.g., Mallick, P., Schirle, M., Chen, S. S., Flory, M. R., Lee, H., Martin, D., Ranish, J., Raught, B., Schmitt, R., Werner, T., Kuster, B., Aebersold, R., *Computational prediction of proteotypic peptides for quantitative proteomics*. Nat. Biotechnol. 25: 125-131, 2007; Fusaro, V. A., Mani, D. R., Mesirov, J. P., Carr, S. A., Prediction of high-responding peptides for targeted protein assays by mass spectrometry. Nat. Biotechnol. 27: 190-198, 2009).

In general, conventional approaches to address the shortcomings of current MS technology focus on developing novel chemistries and technologies to improve quantitative mass analysis, accepting the underlying condition that certain biological compounds are more difficult to ionize and detect by virtue of their chemical structure.

Some aspects of this invention, in contrast, provide molecules, compositions, and methods for the translation of target analytes into biochemical moieties with high ionization efficiency and, thus, optimized for MS-based detection and quantification. In some embodiments, this translation of analyte identity and quantity into biochemical structures optimized for MS allows for the simultaneous assessment of multiple analytes, for example, analytes of different physiochemical properties, and, thus, of different detectability in MS based assays. In some embodiments, multiple analytes of different physiochemical properties are translated into a set of isobaric mass reporters, for example, isobaric peptide mass tags that are optimized for MS based detection, for example, in MS/MS assays. In some embodiments, the translation allows for the qualitative and/or quantitative analysis of a plurality of target analytes by LC MS/MS. In some embodiments, biochemical encoding of analytes of different physiochemical properties into isobaric mass tags as provided herein allows to focus the MS analysis on the specific mass window of the isobaric mass tags, which increases sensitivity and accuracy of the analysis and/or reduces the time required to monitor the relevant mass window. In some embodiments, the translation comprises a step of enriching target analytes, for example, target analytes in a complex biological sample.

Some aspects of this invention provide isotope-encoded reporters (iCOREs), which can be used as mass tags. In some embodiments, iCOREs are provided that are attached to binding agents, e.g., antibodies or antibody fragments, for example, via photo-labile linkers. In some embodiments, iCOREs are used for the qualitative or quantitative detection of a target analyte by an MS assay, for example, by LC MS/MS. In some embodiments, iCOREs are used for the qualitative or quantitative detection of an activity, for example, of a target enzyme activity (e.g., a protease, kinase, or phosphatase activity) by an MS assay, for example, by LC MS/MS.

In some embodiments, complex samples, for example, biological or clinical samples, containing target analytes are first selectively enriched by capture antibodies coated onto magnetic microspheres (see, e.g., FIG. 1). The immobilized analytes are then contacted with iCORE-labeled binding agents. Following binding and removal of unbound binding reagents, individual iCOREs are cleaved from the binding agents through UV irradiation and the pool of these "rescued" iCOREs is analyzed by an MS assay, for example, by LC MS/MS. In some embodiments, the presence and/or abundance of individual iCOREs, as determined by the presence and/or the signal strength obtained from each iCORE, is used to determine the presence or absence and/or the abundance (e.g., the concentration) of a target analyte or activity.

In some embodiments, one or more iCOREs are administered to a subject. For example, in some embodiments, iCOREs may be formulated, administered to a subject, and collected according to the methods described herein, or those described in PCT Application PCT/US2010/000633, filed on Mar. 2, 2010, and entitled Methods And Products For In Vivo Enzyme Profiling, the entire contents of which are incorporated herein by reference. For example, iCOREs designed to interrogate analytes or enzyme activity in a subject suspected of having a disease may be administered to the subject, and analyte- or enzyme-modified iCOREs may be collected at a time sufficient for the iCOREs to be exposed to the analyte or enzyme activity in the subject. In some embodiments, a sample (e.g., a urine, blood, serum, or plasma sample) is collected from the subject and "rescued" iCOREs are detected within the urine sample, e.g., as described herein or in PCT Application PCT/US2010/000633. In some embodiments, the presence and/or abundance of individual iCOREs, as determined by the presence and/or the signal strength obtained from each iCORE, is used to determine the presence or absence and/or the abundance (e.g., the concentration) of a target analyte or activity.

Figure 2:
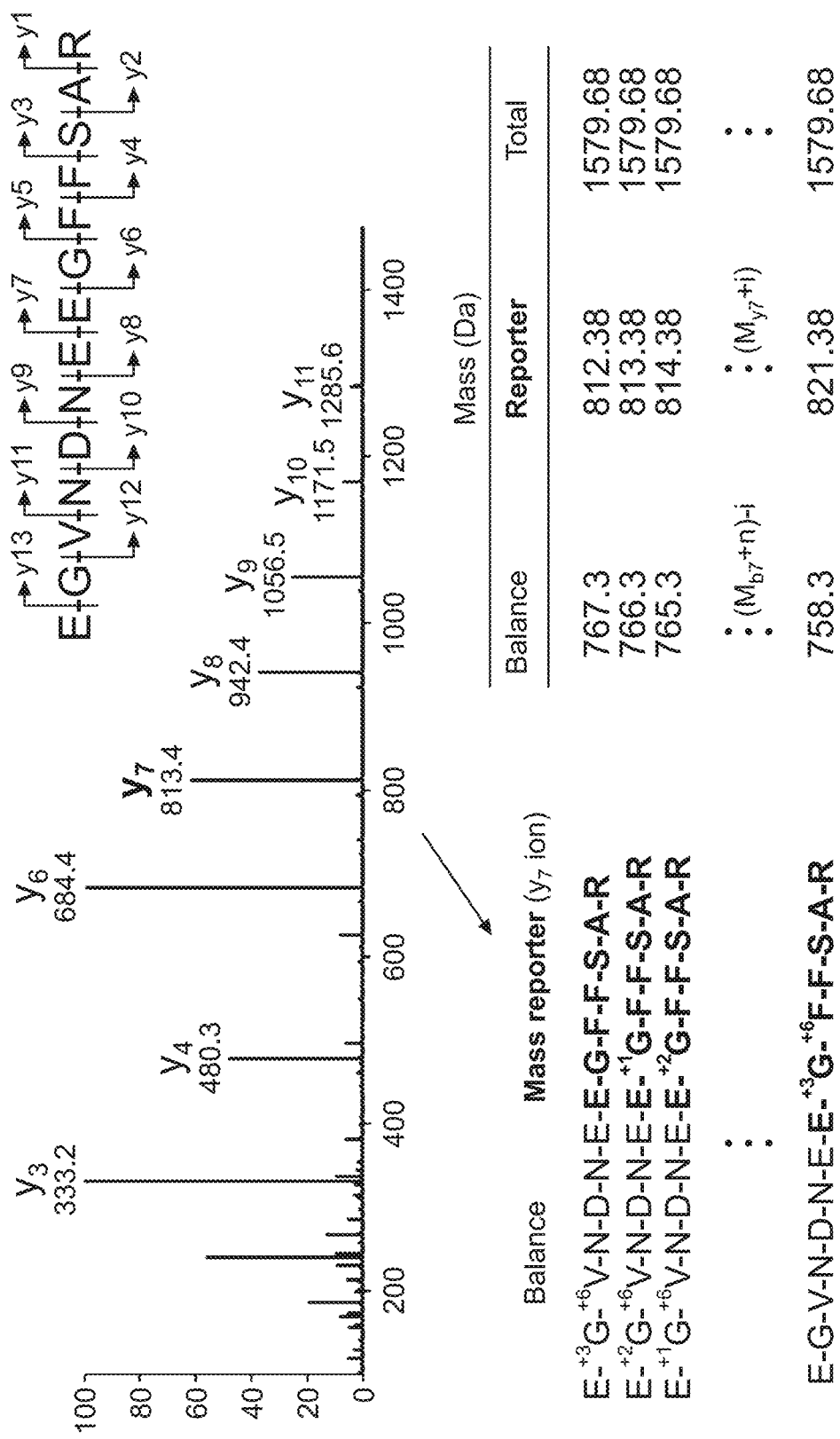
FIG. 2. Utilization of a canonical peak from glu-fib MS/MS spectra as reporter. The fragmentation spectrum of glu-fib and an exemplary encoding strategy is shown. EGVNDNEEGFFSAR corresponds to SEQ ID NO: 1.

Some aspects of this invention also provide a method for producing sets, or libraries, of mass codes from a single peptide-based reporter to enable multiplexed experiments in which multiple analytes are simultaneously detected and/or quantified in a single sample. In some embodiments, an iCORE with favorable MS properties is selected. Some non-limiting examples of suitable iCOREs are described herein and additional iCOREs useful according to some aspects of this invention will be apparent to those of skill in the art based on this disclosure. For example, in some embodiments, a glu-fib peptide (EGVNDNEEGFFSAR, SEQ ID NO: 1) is used as the parent iCORE. Starting from this parent sequence, a set of isotopic analogs (e.g., glu-fib iCOREs with unique fragmentation signature) are designed, thus creating an iCORE library comprising a number of iCOREs of identical mass (isobaric iCOREs), but with distinct fragmentation reporter ions, e.g., y-ions of different masses. Such isobaric iCOREs are indistinguishable during MS analysis, but following peptide fragmentation, e.g., by collision induced disassociation (CID), infrared multiphoton dissociation (IRMPD), or any other suitable fragmentation method known to those of skill in the art), each member of the set, can be distinguished by its unique fragmentation reporter ion in a tandem MS (MS/MS) assay (FIG. 2). The generation of unique, distinguishable fragmentation signatures is accomplished, in some embodiments, by the strategic substitution of stable-isotope enriched amino acids in the parent peptide sequence. In some embodiments, a set of binding agents is conjugated to a set of iCOREs having a set of unique, distinguishable fragmentation signatures, for example, a set of iCOREs differentially labeled with isotopes that give rise to fragmentation ions that can be identified by MS/MS, so that each unique isotope-labeling pattern, and associated fragmentation ion signature, is associated only with binding agents specifically binding one analyte. In such embodiments, the cognate specificity of each binding agent is encoded by the isotope-labeling pattern, and the associated fragmentation signature of the associated iCORE. In some embodiments, such a set of binding agent-conjugated iCOREs is used for the multiplexed detection and/or quantification of analytes or activities in a sample, for example, a biological or clinical sample, or in vivo, according to methods provided herein.

There are several advantages associated with the reagents and methods provided herein as compared to conventional MS-based analyte detection methodology. For example, in some embodiments, target analytes are enriched by binding agents, e.g., by capture antibodies specifically binding an analyte of interest, immobilized on a solid substrate, e.g., a magnetic bead or microsphere, or a membrane or resin. In some embodiments, this enrichment allows for more sensitive and/or specific analyte detection, and/or reduces background signal, particularly in complex samples, such as samples of body fluids (e.g. blood or serum), tissues, or cells.

Further, in some embodiments, target analytes are translated into surrogate isotope-coded reporters (iCOREs) that are pre-designed for facile detection and/or quantification by MS/MS. In some embodiments, this translation, or biochemical encoding, of analytes, e.g., analytes which are challenging to detect by MS assays, into MS tags that are facile to detect, allows for the circumvention of challenges of detecting endogenous chemical structures or peptides directly. This is of particular advantage in the context of multiplexed assays, in which a plurality of analytes of different structure are assayed. Direct detection of different structures in one multiplex MS assay typically requires the screening of a large mass window and while some analytes can readily be detected via MS, many analytes are hard or impossible to detect without extensive pre-processing, or cannot be identified unambiguously when analyzing complex samples.

In some embodiments, a single analyte molecule is translated into a plurality of iCORE molecules, resulting in a higher sensitivity of analyte detection, for example, by a signal amplification of about 3-20 fold. For example, in some embodiments, a binding agent that specifically binds a single molecule or two molecules of a target analyte, e.g., an antibody or fragment thereof, is conjugated to a plurality of iCORE molecules, for example, to about 3, about 5, about 10, or about 20 iCORE molecules, providing an about 3, about 5, about 10, or about 20 fold amplification of the number of molecules available for MS as compared to direct MS detection of the target analyte, respectively. It will be appreciated by those of skill in the art that higher amplification rates can be achieved by attaching more iCORE molecules to a binding agent molecule. Methods and reagents for the attachment of iCOREs to binding agents are provided herein and additional methods will be apparent to those of skill in the art.

The use of photo-labile linkers during the translation process, for example, in embodiments where iCOREs bound to binding agents, e.g. antibodies or antibody fragments, are employed, enables ultra-violet light-triggered release of iCOREs from the binding agents. The high efficiency of this photochemical process is in marked contrast with the derivation of peptides from proteins by enzymatic digestion (necessary for multiplexed protein detection in conventional LC MS/MS assays) which is limited by the biophysical properties of the enzyme employed (e.g. KD, kcat, substrate specificity) and the requirement for optimal sample conditions for enzymatic activity (e.g. pH, salt concentration). Both of these constraints lead to increased sample processing requirements and/or decreased detection efficiency.

Further, the use of pre-determined mass tags, e.g., isobaric iCOREs, with known masses greatly simplifies the collection and analysis of data since it is unnecessary to query a large mass window (e.g. 50-2000 m/z) for analytes of diverse molecular weight. Rather, with isobaric codes, narrow mass windows can be centered on the parent mass (e.g. ±0.5 m/z) to efficiently collect signal. In some embodiments, this targeted approach, combined with analyte signal amplification during translation, increases detection sensitivity by ~30-300 fold. Moreover, in some embodiments, the simplification of data collection and the resulting decrease in spectrometer operating time reduces overall costs by ~10 fold.

Further, the method of generating isobaric iCORE mass tag libraries, for example, isobaric iCORE peptide libraries, is an improvement over current technologies because of the large degree of encoding that can be achieved, which translates into multiplexing capabilities far beyond the current limitations. The current state-of-the-art in isobaric MS multiplexing is iTRAQ mass tag technology (Ross P L, Huang Y N, Marchese J N, Williamson B, Parker K, Hattan S, Khainovski N, Pillai S, Dey S, Daniels S, Purkayastha S, Juhasz P, Martin S, Bartlet-Jones M, He F, Jacobson A, Pappin D J., *Multiplexed protein quantitation in Saccharomyces cerevisiae using amine-reactive isobaric tagging reagents*, Mol Cell Proteomics. 2004 December; 3(12): 1154-69). ITRAQ labeling reagents are amine-reactive small molecules providing for 4 or maximally 8 unique mass codes. A larger library is precluded by the number of atoms available in small molecules for isotopic substitution. With iCOREs, e.g., peptide iCOREs, as provided by some aspects of this invention, however, the number of atoms available for isotopic substitution is increased by the number of monomers, e.g., amino acids, that can be labeled with heavy isotopes. Accordingly, it is feasible to construct, for example, at least ~30-40 unique codes from an average peptide length of ~15 amino acids. The library size, and, thus, the number of unique encoding tags can be increased further by using longer peptides and/or by combining distinct sets of isobaric iCORE peptides, providing for ~100-1000, or more, elements.

Some aspects of this invention provide isotope-coded reporter molecules (iCORE) and methods of their use. In some embodiments, iCOREs are useful as mass tags in MS assays, for example, in multiplex LC MS/MS assays, as described in more detail elsewhere herein. In some embodiments, iCOREs are useful in the simultaneous qualitative and/or quantitative detection of tens, hundreds, or thousands of analytes in a sample, for example, a complex biological sample, or in the simultaneous tracking of tens, hundreds, or thousands of cells, tissues, or samples using an MS readout.

In some embodiments, a set, plurality, or library of different iCOREs is provided that is useful in multiplex MS assays, for example, in multiplex LC MS/MS assays. In some embodiments, the iCOREs of a set, plurality, or library of iCOREs are isobaric. For example, in some embodiments, a set, plurality, or library of isobaric iCOREs is provided in which all iCOREs are polymers, e.g., peptides of the same amino acid sequence (e.g., glu-fib peptides (EGVNDNEEGFFSAR, SEQ ID NO: 1)), and have, accordingly, the same physicochemical properties as relevant for MS analysis. Accordingly, all iCOREs of such a set, plurality, or library are detected with substantially the same specificity, sensitivity, and accuracy in an LC MS/MS assay. In some embodiments, different iCOREs in such a set, plurality, or library of isobaric iCOREs have different fragmentation signatures, which can readily be distinguished in an MS/MS assay as described in more detail elsewhere herein. Because even short polymers, e.g., short polypeptides, allow for the generation of a large number of unique fragmentation signatures in a set, plurality or library of isobaric iCOREs that can be distinguished via MS/MS assays, for example, by differential isotope-labeling of the iCOREs, this technology can be used for multiplex qualitative or quantitative MS analysis far beyond the limitations of current multiplex MS technologies, such as iTRAQ (4- or 8-plex max.) or tandem mass tag (TMT, 6-plex max.) technologies.

Figure 3:
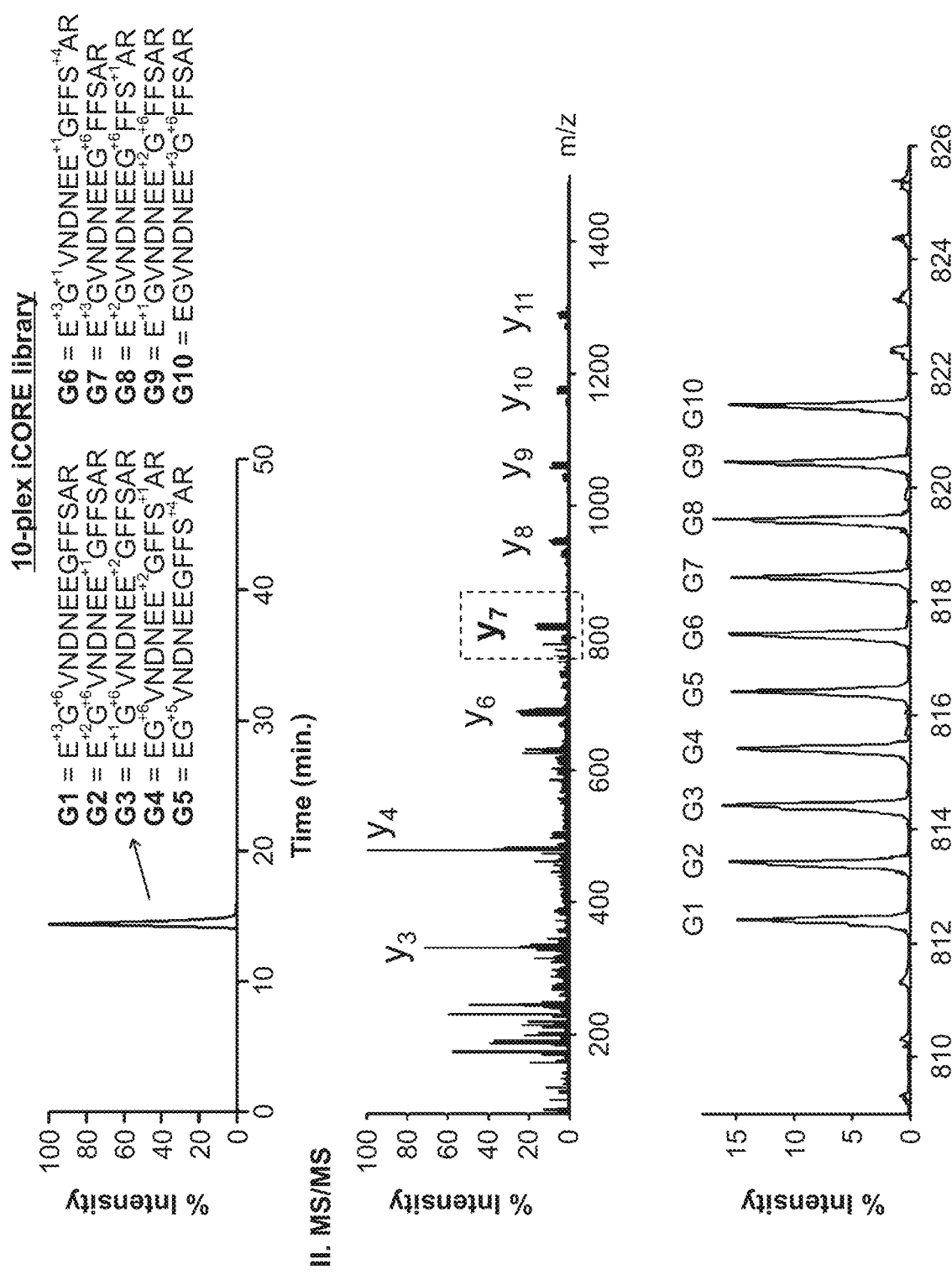
FIG. 3. MS and MS/MS data obtained from a 10-plex iCORE library experiment. EGVNDNEEGFFSAR corresponds to SEQ ID NO: 1.

A non-limiting, exemplary set of 10 isobaric peptide iCOREs of the amino acid sequence EGVNDNEEGFFSAR (SEQ ID NO: 1) is described in FIG. 3. The different iCOREs G1-G10 have different isotope patterns, and, thus, different fragmentation signatures, e.g., G1 has the isotope pattern $E^{+3}G^{+6}$VNDNEEGFFSAR (SEQ ID NO: 1), G2 has the isotope pattern $E^{+2}G^{+6}$VNDNEE$^{+1}$GFFSAR (SEQ ID NO: 1), G3 has the isotope pattern $E^{+1}G^{+6}$VNDNEE$^{+2}$GFFSAR (SEQ ID NO: 1), and so forth. In the first round of MS, only a single peak is observed, reflecting the isobaric nature of iCOREs G1-10 (FIG. 3 I.). After fragmentation, however, the unique fragmentation signatures of G1-10 result in resolution of the fragments as 10 distinct peaks (FIG. 3 II.). The lower panel of the figure shows a close-up of the peaks obtained from the y7 ion (EGFFSAR, SEQ ID NO: 6, see FIG. 2 for y ion nomenclature), allowing qualitative (present/absent) as well as quantitative analysis of each unique iCORE in the set. Those of skill in the art will appreciate that the glu-fib peptide sequence allows for the generation of more than 10 unique fragmentation signatures via differential isotope labeling, for example, by further encoding the remaining amino acids within the sequence, and that the exemplary set of ten iCOREs is not limiting in this respect. The multiplexing capabilities of iCORE technology are limited only by the number of unique fragmentation patterns that can be created in iCOREs. Even a small peptide sequence, such as the glu-fib peptide sequence exemplified in FIG. 3 allows for the generation of at least 30-40 unique isotope signatures, if commercially available isotope-labeled amino acids are used, and more if such amino acids are custom-synthesized.

Three non-limiting, exemplary differential isotope-labeling strategies for generating multiplex glu-fib based iCORE libraries are provided below. In these examples, iCOREs are isotope-labeled by substitution of one or more atoms in the indicated amino acids with one or more heavy isotopes, resulting in a change in mass of the labeled amino acid. The resulting iCOREs in each library are isobaric, with different iCOREs having a different fragmentation signature, e.g., with respect to the $y_7$ ion. The examples are intended for illustration only and do not limit this aspect of the invention. Additional useful differential isotope-labeling strategies and schemes will be apparent to those of skill in the art.

```
10-plex glu-fib iCORE library (G10):
                                    (SEQ ID NO: 36)
G101 = E-+3G-+6V-N-D-N-E-E-G-F-F-S-A-R

G102 = E-+2G-+6V-N-D-N-E-E-+1G-F-F-S-A-R

G103 = E-+1G-+6V-N-D-N-E-E-+2G-F-F-S-A-R

G104 = E-G-+6V-N-D-N-E-E-+2G-F-F-S-+1A-R
```

-continued $G_{10}5$ = E-G-$^{+5}$V-N-D-N-E-E-G-F-F-S-$^{+4}$A-R $G_{10}6$ = E-$^{+3}$G-$^{+1}$V-N-D-N-E-E-$^{+1}$G-F-F-S-$^{+4}$A-R $G_{10}7$ = E-$^{+3}$G-V-N-D-N-E-E-G-$^{+6}$F-F-S-A-R $G_{10}8$ = E-$^{+2}$G-V-N-D-N-E-E-G-$^{+6}$F-F-S-$^{+1}$A-R $G_{10}9$ = E-$^{+1}$G-V-N-D-N-E-E-$^{+2}$G-$^{+6}$F-F-S-A-R $G_{10}10$ = E-G-V-N-D-N-E-E-$^{+3}$G-$^{+6}$F-F-S-A-R 18-plex glu-fib iCORE library (G18)

(SEQ ID NO: 36)

$G_{18}1$ = E-$^{+3}$G-$^{+6}$V-$^{+6}$N-D-$^{+2}$N-E-E-G-F-F-S-A-R $G_{18}2$ = E-$^{+2}$G-$^{+6}$V-$^{+6}$N-D-$^{+2}$N-E-E-G-F-F-S-$^{+1}$A-R $G_{18}3$ = E-$^{+1}$G-$^{+6}$V-$^{+6}$N-D-$^{+2}$N-E-E-$^{+1}$G-F-F-S-$^{+1}$A-R $G_{18}4$ = E-G-$^{+6}$V-$^{+6}$N-D-$^{+2}$N-E-E-$^{+2}$G-F-F-S-$^{+1}$A-R $G_{18}5$ = E-G-$^{+5}$V-$^{+6}$N-D-$^{+2}$N-E-E-G-F-F-S-$^{+4}$A-R $G_{18}6$ = E-$^{+1}$G-$^{+5}$V-$^{+6}$N-D-$^{+2}$N-E-E-$^{+1}$G-F-F-S-$^{+4}$A-R $G_{18}7$ = E-$^{+3}$G-V-$^{+6}$N-D-$^{+2}$N-E-E-G-$^{+6}$F-F-S-A-R $G_{18}8$ = E-$^{+2}$G-V-$^{+6}$N-D-$^{+2}$N-E-E-G-$^{+6}$F-F-S-$^{+1}$A-R $G_{18}9$ = E-$^{+1}$G-V-$^{+6}$N-D-$^{+2}$N-E-E-$^{+1}$G-$^{+6}$F-F-S-$^{+1}$A-R $G_{18}10$ = E-$^{+1}$G-$^{+5}$V-N-D-$^{+2}$N-E-E-$^{+2}$G-$^{+6}$F-F-S-$^{+1}$A-R $G_{18}11$ = E-G-$^{+5}$V-N-D-$^{+2}$N-E-E-G-$^{+10}$F-F-S-A-R $G_{18}12$ = E-$^{+3}$G-$^{+1}$V-N-D-$^{+2}$N-E-E-G-$^{+10}$F-F-S-$^{+1}$A-R $G_{18}13$ = E-$^{+2}$G-$^{+1}$V-N-D-$^{+2}$N-E-E-$^{+1}$G-$^{+10}$E-F-S-$^{+1}$A-R $G_{18}14$ = E-$^{+2}$G-V-N-D-$^{+2}$N-E-E-$^{+2}$G-$^{+10}$F-F-S-$^{+1}$A-R $G_{18}15$ = E-$^{+1}$G-V-N-D-$^{+2}$N-E-E-G-$^{+10}$F-F-S-$^{+4}$A-R $G_{18}16$ = E-$^{+2}$G-V-N-D-N-E-E-$^{+1}$G-$^{+10}$F-F-S-$^{+4}$A-R $G_{18}17$ = E-$^{+1}$G-V-N-D-N-E-E-G-$^{+10}$F-$^{+6}$F-S-A-R $G_{18}18$ = E-G-V-N-D-N-E-E-G-$^{+10}$F-$^{+6}$F-S-$^{+1}$A-R 22-plex glu-fib iCORE library (G22)

(SEQ ID NO: 36)

$G_{22}1$ = E-$^{+3}$G-$^{+6}$V-$^{+6}$N-D-$^{+6}$N-E-E-G-F-F-S-A-R $G_{22}2$ = E-$^{+2}$G-$^{+6}$V-$^{+6}$N-D-$^{+6}$N-E-E-G-F-F-S-$^{+1}$A-R $G_{22}3$ = E-$^{+1}$G-$^{+6}$V-$^{+6}$N-D-$^{+6}$N-E-E-$^{+1}$G-F-F-S-$^{+1}$A-R $G_{22}4$ = E-G-$^{+6}$V-$^{+6}$N-D-$^{+6}$N-E-E-$^{+2}$G-F-F-S-$^{+1}$A-R $G_{22}5$ = E-G-$^{+5}$V-$^{+6}$N-D-$^{+6}$N-E-E-G-F-F-S-$^{+4}$A-R $G_{22}6$ = E-G-$^{+5}$V-$^{+6}$N-D-$^{+6}$N-E-E-$^{+1}$G-F-F-S-$^{+4}$A-R $G_{22}7$ = E-$^{+3}$G-V-$^{+6}$N-D-$^{+6}$N-E-E-G-$^{+6}$F-F-S-A-R $G_{22}8$ = E-$^{+2}$G-V-$^{+6}$N-D-$^{+6}$N-E-E-G-$^{+6}$F-F-S-$^{+1}$A-R $G_{22}9$ = E-$^{+1}$G-V-$^{+6}$N-D-$^{+6}$N-E-E-$^{+1}$G-$^{+6}$F-F-S-$^{+1}$A-R $G_{22}10$ = E-$^{+1}$G-$^{+5}$V-N-D-$^{+6}$N-E-E-$^{+2}$G-$^{+6}$F-F-S-$^{+1}$A-R $G_{22}11$ = E-G-$^{+5}$V-N-D-$^{+6}$N-E-E-G-$^{+10}$F-F-S-A-R $G_{22}12$ = E-$^{+3}$G-$^{+1}$V-N-D-$^{+6}$N-E-E-G-$^{+10}$F-F-S-$^{+1}$A-R $G_{22}13$ = E-$^{+2}$G-$^{+1}$V-N-D-$^{+6}$N-E-E-$^{+1}$G-$^{+10}$F-F-S-$^{+1}$A-R $G_{22}14$ = E-$^{+2}$G-V-N-D-$^{+6}$N-E-E-$^{+2}$G-$^{+10}$F-F-S-$^{+1}$A-R $G_{22}15$ = E-$^{+1}$G-V-N-D-$^{+6}$N-E-E-G-$^{+10}$F-F-S-$^{+4}$A-R $G_{22}16$ = E-$^{+1}$G-$^{+5}$V-N-D-N-E-E-$^{+1}$G-$^{+10}$F-F-S-$^{+4}$A-R $G_{22}17$ = E-G-$^{+5}$V-N-D-N-E-E-G-$^{+10}$F-$^{+6}$F-S-A-R $G_{22}18$ = E-$^{+3}$G-$^{+1}$V-N-D-N-E-E-G-$^{+10}$F-$^{+6}$F-S-$^{+1}$A-R $G_{22}19$ = E-$^{+2}$G-$^{+1}$V-N-D-N-E-E-$^{+1}$G-$^{+10}$F-$^{+6}$F-S-$^{+1}$A-R $G_{22}20$ = E-$^{+2}$G-V-N-D-N-E-E-$^{+2}$G-$^{+10}$F-$^{+6}$F-S-$^{+1}$A-R $G_{22}21$ = E-$^{+1}$G-V-N-D-N-E-E-G-$^{+10}$F-$^{+10}$F-S-A-R $G_{22}22$ = E-G-V-N-D-N-E-E-G-$^{+10}$F-$^{+10}$F-S-$^{+1}$A-R

In some embodiments, the isotope-labeled amino acids are D-amino acids. In some embodiments, the isotope-labeled amino acids are L-amino acids. In some embodiments, the isotope-labeled amino acids are a mix of D- and L-amino acids.

Those of skill in the art will appreciate that longer polymers, for example, longer polypeptides, polysaccharides, or polynucleotides, allow for even more unique fragmentation signatures to be generated by differential isotope labeling, thus further expanding the multiplexing capabilities of iCORE technology.

In some embodiments, a set, plurality, or library of iCOREs (e.g. polypeptide, polynucleotide, or polysaccharide iCOREs) is provided that comprises at least 2, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, at least 100, at least 125, at least 150, at least 200, at least 250, at least 500, at least 1000, or more than 1000 different iCOREs, e.g. iCOREs that have a unique fragmentation signature that is distinguishable by an MS assay, e.g. an MS/MS assay. In some embodiments, the iCOREs in the set, plurality, or library are isobaric iCOREs, for example, isobaric polypeptide, polynucleotide, or polysaccharide iCOREs. In some embodiments, each unique fragmentation signature in a set of iCOREs, for example, a set of isobaric iCOREs, is associated with, or represents, a specific analyte, or parameter. Methods for the use of iCOREs, for example, in analyte detection, as well as cell, tissue, sample, and liquid tracking, are also provided.

The term iCORE refers to isotope-coded reporter molecules. In some embodiments, an iCORE is a molecule that is readily detectable by MS technology. In some embodiments, an iCORE is a peptide, for example, a peptide known to be readily detectable by MS technology. In other embodiments, an iCORE is a polynucleotide or a polysaccharide. Typically, an iCORE is a molecule that allows for differential isotope-labeling, e.g., for the generation of unique fragmentation signatures that are distinguishable in a detection assay, such as MS/MS. This allows for the generation of libraries of isobaric iCOREs which share the same physiochemical properties for the purpose of MS detection, for example, peptide iCOREs having the same amino acid sequence, and are readily distinguishable by their unique fragmentation signature, for example, in LC MS/MS assays. Typically, an iCORE is a polymer comprised of monomers that exhibit different MS signatures and, thus, comprises a sequence of monomers. Such polymers are well known to those of skill in the art and include, but are not limited to polymers of amino acids, nucleotides, and monosaccharides, for example, polypeptides, polynucleotides, and polysaccharides, respectively.

The length of iCOREs is typically chosen to produce a mass signature that is useful in MS assays, for example, a mass signature that can readily be detected in an MS/MS assay. For example, in some embodiments, an iCORE is a polymeric molecule (e.g., a polypeptide, polynucleotide, or polysaccharide) that comprises at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 70, at least 80, at least 90, or at least 100 monomer residues, for example, amino acid, nucleotide, or monosaccharide residues. In some embodiments, an iCORE is a polymeric molecule, for example, a polypeptide, polynucleotide, or polysaccharide, that comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 51-60, 61-70, 71-80, 81-90, or 91-100 monomers, e.g., amino acid or nucleotide residues. In some embodiments, an iCORE is a polymer comprising more than 100 monomers, for example, more than 100 amino acid, nucleotide, or monosaccharide residues.

Non-limiting examples of polymeric molecules that are useful for the generation of iCOREs are the polypeptides glu-fib (EGVNDNEEGFFSAR (SEQ ID NO: 1)), bradykinin (PPGFSPFR (SEQ ID NO: 30)), angiotensin I (DRVYIHPFHL (SEQ ID NO: 31)), ACTH1-17 (SYSMEHFRWGKPVGKKR (SEQ ID NO: 32)), ACTH18-39 (RPVKVYPNGAEDESAEAFPLEF (SEQ ID NO: 33)), and ACTH7-38 (FRWGKPVGKKRRPVKVYPNGAEDESAEAFPLE (SEQ ID NO: 34)). Additional polymeric molecules and sequences that can be used for the generation of iCOREs will be readily evident to those of skill in the art and the invention is not limited in this respect.

In order to generate an iCORE from a non-labeled polymeric molecule, for example, a polypeptide, polynucleotide, or polysaccharide, the polymeric molecule is isotope-labeled. Methods and reagents for isotope-labeling of polymeric molecules are well known to those of skill in the art. In some embodiments, such methods include the generation of a polymeric molecule, for example, a peptide, from monomers, for example, amino acids, at least some of which are isotope-labeled to obtain an isotope-labeled polymeric molecule. In some embodiments, isotope-labeling is effected by the introduction of heavy isotopes. Isotope-labeling with radioactive isotopes or with stable isotopes is possible. In some embodiments, labeling with stable isotopes is preferred.

For example, while non-labeled monomers, e.g., non-labeled amino acids, nucleotides, or monosaccharides, predominantly comprise $C^{12}$, $O^{16}$, $N^{14}$, and $S^{32}$ atoms, isotope-labeled monomers, e.g., isotope-labeled amino acids, may comprise one or more heavy isotope(s), for example, a $C^{13}$, $N^{15}$, $O^{17}$, $O^{18}$, $H^2$, $S^{33}$, $S^{34}$, or $S^{36}$ isotope. A monomer comprising a heavy isotope has a different mass than a non-labeled amino acid, and even a single isotope comprised in a monomer can readily be measured by MS assays. This difference in mass is conferred to any polymer comprising such an isotope-labeled monomer. For example, the difference in mass resulting from the substitution of a $C^{12}$ atom of an amino acid with a $C^{13}$ isotope can be measured in a peptide comprising such an isotope-labeled amino acid.

To give a non-limiting example of monomer isotope labeling, the phenyl ring of non-labeled phenylalanine (F) typically comprises six $C^{12}$ atoms. In some embodiments, an isotope-labeled phenylalanine residue comprises a phenyl ring comprising five $C^{12}$ atoms and one $C^{13}$ isotope, increasing the mass of the labeled amino acid by the mass of one neutron ($^{+1}F$). In some embodiments, an isotope-labeled phenylalanine residue comprises a phenyl ring comprising four $C^{12}$ atoms and two $C^{13}$ isotopes, increasing the mass of the labeled amino acid by the mass of two neutrons ($^{+2}F$). In some embodiments, an isotope-labeled phenylalanine residue comprises a phenyl ring comprising three $C^{12}$ atoms and three $C^{13}$ isotopes ($^{+3}F$), two $C^{12}$ atoms and four $C^{13}$ isotopes ($^{+4}F$), one $C^{12}$ atoms and five $C^{13}$ isotopes ($^{+5}F$), or six $C^{13}$ isotopes ($^{+6}F$). The remaining three C12 atoms of non-labeled phenylalanine and as well as the N14 atom of the amino group can also be isotope-substituted, yielding $^{+7}F$, $^{+8}F$, $^{+9}F$, and $^{+10}F$. It will be appreciated by those of skill in the art that any combination of isotope substitutions are possible, for example, substitution of the $N^{14}$ of the amino group, of the $C^{12}$ of the carboxy group and of two $C^{12}$ of the phenyl ring would produce $^{+4}F$, as would a substitution of three phenyl ring $C^{12}$ with $C^{13}$ and of the $N^{14}$ with $N^{15}$, or substitution of four $C^{12}$ of the phenyl ring with 4 $C^{13}$. In some embodiments, the isotope-labeled phenylalanine is used to generate an isotope-labeled peptide. In some embodiments, this involves peptide synthesis in vivo, for example, by cells that are incubated in the presence of isotope-labeled phenylalanine and incorporate the labeled amino acid into any peptide they synthesize. In some embodiments, isotope-labeled peptides are synthesized in vitro, for example, via fmoc synthesis using isotope-labeled amino acids as building blocks.

It will be appreciated by those of skill in the art that amino acids other than phenylalanine can be isotope-labeled according using similar strategies and methods and reagents known to those of skill in the art and the invention is not limited in this respect. It will further be appreciated that monomers other than amino acids can be isotope-labeled, for example, nucleotides and monosaccharides. Further, other methods for the generation of isotope-labeled polymers that are useful as iCOREs, for example, methods in which a polymer is directly labeled, are also known to those of skill in the art, and the invention is not limited in this respect.

Different fragmentation signatures can be created by differential isotope labeling of polymeric molecules, for example, by adding different amounts of heavy isotopes to the same monomeric residue, or by generating different combinations of labeled monomeric residues within the polymeric molecule. For an example of different iCORE fragmentation signatures created by differential isotope labeling, see iCOREs G1-G10 described in FIG. 3. Isotope-labeling of a polypeptide, polynucleotide, or polysaccharide at a specific residue, for example, a specific amino acid, nucleotide, or monosaccharide residue, produces a specific isotope labeling signature that can readily be identified, and distinguished from other polypeptides, polynucleotides, or polysaccharides of the same monomeric sequence that are labeled at a different residue, via MS assays, for example, via MS/MS assays. This allows for the generation of multiple iCOREs comprising the same monomeric sequence, for example, multiple polynucleotide iCOREs comprising the same amino acid sequence, but isotope-labeled at different residues. Such differentially labeled, isobaric iCOREs exhibit identical physiochemical properties for the purpose of MS assays, and are, thus, detectable at an equal level of sensitivity, specificity, and accuracy in MS assays, while still being distinguishable by their unique fragmentation signature, for example, in LC MS/MS assays as described herein.

In some embodiments, iCOREs are polypeptides. Typically, polypeptide iCOREs comprise a sequence that is optimized for facile detection in MS assays, as exemplified by the iCORE sequences provided herein. In some embodiments, a library of isobaric iCOREs is provided, in which all iCOREs comprise the same amino acid sequence, but different iCOREs comprise different isotope-labeling signatures. Even short polypeptides, e.g. of about 5-20 amino acids in length, allow for the generation of tens or hundreds of unique isotope-labeling signatures, which translates into the possibility to detect and analyze tens or hundreds of analytes in a multiplexed MS assay using isobaric iCOREs of such lengths. In some embodiments, a library of peptide iCOREs is provided that comprises iCOREs of different amino acid sequences, further increasing the number of unique isotope-labeling signatures and, thus, the number of analytes that can be assayed in a single multiplexed MS experiment. Such heterogeneous iCORE libraries can be generated, for example, by combining a first iCORE library comprising isobaric, differentially labeled iCOREs with an additional library comprising isobaric, differentially labeled iCOREs. For example, such a library could be generated by combining a library of glu-fib based iCOREs with a library of bradykinin based iCOREs and a library of angiotensin I-based iCOREs, thus creating a larger, combinatorial library of iCOREs.

Some aspects of this invention relate to the recognition that even a relatively small number of relatively short polypeptide tags that are useful in MS assays provide virtually unlimited multiplexing capabilities, since polypeptides are comprised of amino acid residues, and there are 20 naturally occurring and a large number of artificial amino acids that are useful as building blocks for iCOREs. For example, an iCORE library based on isobaric, differentially labeled glu-fib (EGVNDNEEGFFSAR (SEQ ID NO: 1)) iCOREs allows for the detection of about 10-100 analytes in a multiplexed MS assay, while an iCORE library based on isobaric, differentially labeled ACTH7-38 (FRWGKPVGKKRRPVKVYPNGAEDESAEAFPLE (SEQ ID NO: 34)) iCOREs allows for the detection of about 10-400 analytes in a multiplex MS assay. Combinatorial iCORE libraries, accordingly, allow for the assessment of thousands of analytes simultaneously.

Figure 7:
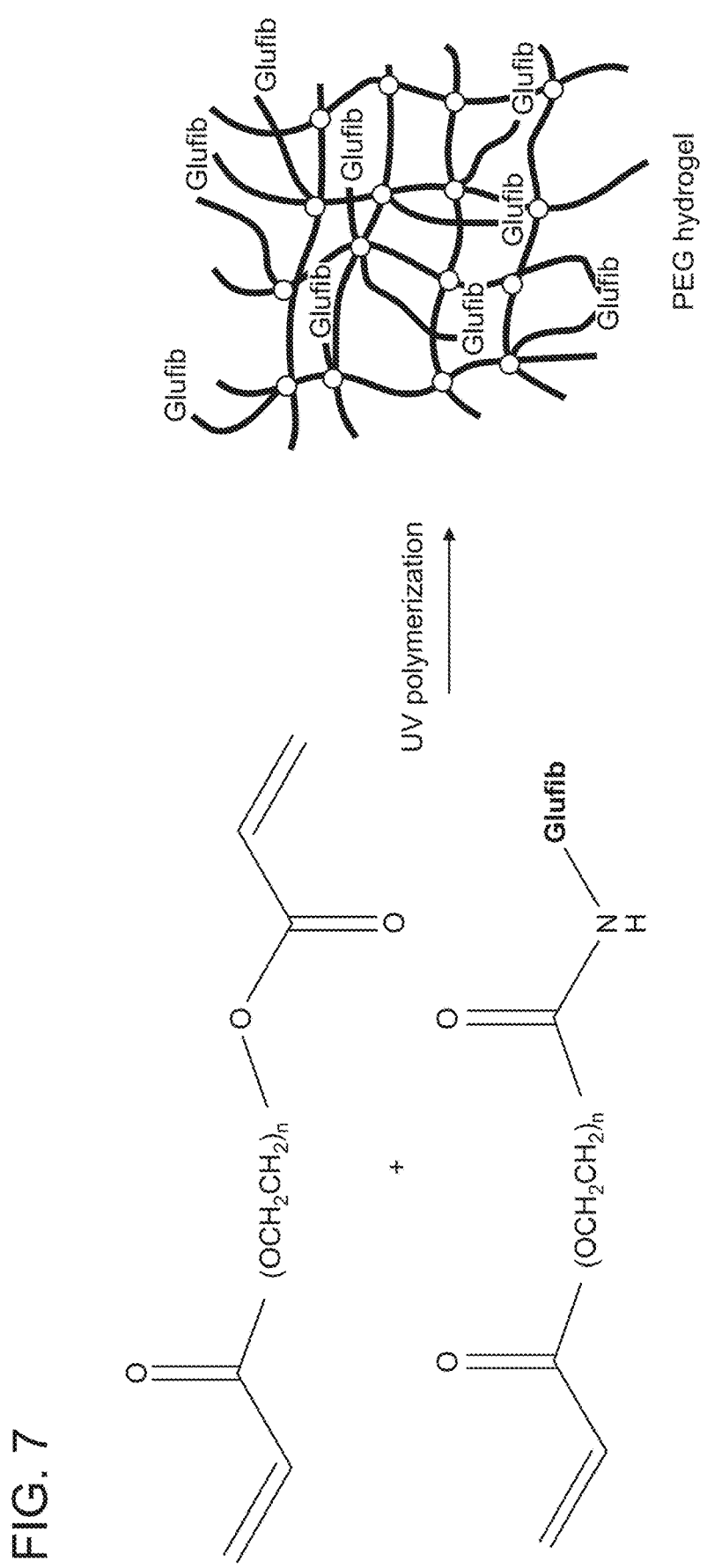
FIG. 7. Exemplary chemistry for the generation of PEG hydrogel-embedded iCORE tags.

Some aspects of this invention provide sets or libraries of iCOREs. In some embodiments, the iCOREs comprise or are conjugated to a reactive moiety that reacts with another molecule. For example, in some embodiments, the iCOREs comprise a reactive moiety that forms a covalent bond to a molecule of interest, for example, to an analyte, or a set of analytes. In some embodiments, the molecule of interest is a peptide or protein, a carbohydrate, a nucleic acid, or a lipid. In some embodiments, the molecule of interest to which the iCORE is aimed to be conjugated is a binding agent, for example, an antibody, antibody fragment, aptamer, ligand, receptor, or adnectin. For example, in some embodiments, a set of iCOREs is provided that is conjugated to a reactive chemical moiety that forms a covalent bond to a protein if contacted with a protein. Reactive chemical moieties are well known to those of skill in the art. One exemplary embodiment is depicted in FIG. 7 to illustrate this point. Here, the iCORE is a glu-fib peptide, covalently bound to a chemical moiety that polymerizes under UV light with PEG monomers to form a PEG hydrogel. Polyethylene glycol (PEG), also known as poly(oxyethylene) glycol, is a condensation polymer of ethylene oxide and water having the general chemical formula $HO(CH_2CH_2O)[n]H$. Such hydrogels are useful, for example, in the generation of engineered tissues and the conjugation of an iCORE to such a hydrogel allows for tracking a tissue grown on such a tagged hydrogel in in vitro or in vivo experiments as described in more detail elsewhere herein. Other reactive chemical moieties and methods for conjugation of such moieties to iCOREs provided herein are well known to those of skill in the art and the invention is not limited in this respect. It will be apparent to those of skill in the art that the type of reactive chemical moiety can be selected to be reactive with a moiety comprised in the molecule of interest to which the iCORE is aimed to be conjugated. In some embodiments, iCOREs are provided that are conjugated to a reactive chemical moiety via a covalent bond. In some embodiments, iCOREs are provided that are conjugated to a reactive chemical moiety via a cleavable linker, for example, a photocleavable linker.

Providing iCOREs conjugated to reactive chemical moieties allows for the customized labeling of molecules of interest by the end-user, for example, by a scientist, thus extending the versatility of iCORE technology to custom-made experimental designs. For example, in some embodiments, iCOREs conjugated with a reactive moiety that forms a covalent bond with peptides may be used to label proteins or peptides obtained from a biological sample for comparison with proteins or peptides obtained from a different sample, much in the same way as ITRAQ tags are commonly used. In contrast to ITRAQ technology, the virtually unlimited number of different fragmentation signatures available for a given iCORE set, for example, a set of isobaric peptide iCOREs as described herein, allows for the simultaneous assessment of a virtually unlimited number of analytes, for example, for the simultaneous assessment and comparison of a virtually unlimited number of protein or peptide samples.

Scalability of iCORE technology depends on the specific binding agents used (for embodiments, in which iCOREs conjugated to specific binding agents are used or provided) and the specific, distinguishable mass reporters, e.g., iCOREs, having a unique, distinguishable fragmentation signature. Regarding specific binding agents, iCOREs can be conjugated to virtually all commercially available binding agents, including, but not limited to, antibodies, antibody fragments, aptamers, ligand-binding proteins or proteins domains, and adnectins by methods well known to those of skill in the art. The number of iCOREs with unique fragmentation signatures scales with the peptide space, which scales as $20^n$, where n=length of peptide, for peptide iCOREs comprising only naturally occurring amino acids. Accordingly, even very short peptide iCOREs provide a large number of possible unique fragmentation signatures, while longer peptides provide virtually limitless unique signatures. In some embodiments, peptide iCOREs that are readily detected by MS are preferable, but even the exemplary, readily detectable peptide iCOREs described herein alone allow for hundreds or thousands of unique fragmentation signatures. Some peptide sequences suitable for the generation of iCOREs are provided herein and additional suitable peptide sequences will be apparent to those of skill in the art based on this disclosure.

In some embodiments, iCOREs are provided that are conjugated to a binding agent. A binding agent is an agent that specifically binds a molecule, for example, an analyte. In some embodiments, the binding agent is an antibody or antibody fragment. In some embodiments, the binding agent is a peptide or protein. In some embodiments, the binding agent is an aptamer or adnectin. In some embodiments, the binding agent is a ligand or a receptor, or comprises a ligand binding domain.

Accordingly, in some embodiments, iCORE-binding agent conjugates are provided that specifically bind to an analyte. In some embodiments, the conjugation of iCORE and binding agent is via a covalent bond, for example, a covalent peptide bond in an iCORE-binding agent fusion protein. In some embodiments, the conjugation of iCORE and binding agent is via a cleavable linker, for example, a protease cleavable linker or a photocleavable linker. In some embodiments, the linker is a peptide linker comprising a protease cleavage site. Some exemplary photocleavable linkers and protease cleavage sites are described herein, and additional linkers and cleavage sites will be apparent to those of skill in the art, and the invention is not limited in this respect. For example, in some embodiments, an iCORE is provided that is conjugated to a binding agent, for example, an antibody, via a photocleavable linker, as described herein. In some embodiments, a set of iCOREs is provided that is conjugated to a set of binding agents, for example, a set of antibodies, or antibody fragments, or ligand binding peptides and proteins, or aptamers or adnectins, or any combination of such agents. Typically, the iCOREs in such a set are conjugated to the binding agents in a manner that allows for the identification of a particular binding agent, and, thus, the analyte bound by a binding agent, by determining the identity of the iCORE.

For example, in a set of 10 different iCOREs (e.g., iCORE G1-G10 in FIG. 2) that are conjugated to a set of 10 different binding agents (B1-B10), which, in turn, specifically bind a set of analytes (A1-A10), the iCOREs are conjugated to the binding agents so that each iCORE of a unique fragmentation signature is conjugated to particular binding agent, e.g. G1 to B1, G2 to B2, G3 to B3, and so forth. The unique fragmentation signature of each iCORE can be identified and distinguished from the fragmentation signatures of the other iCOREs in the library in an MS assay, e.g. the MS/MS assay depicted in FIG. 3. Accordingly, the presence or absence of a specific binding agent in a sample can be inferred from the presence or absence of the unique fragmentation signature of the iCORE associated with that particular binding agent. In some embodiments, a sample is assayed for the presence or absence of a set of analytes by contacting the sample with the set of iCOREs conjugated to the binding agents under conditions suitable for the binding agents to bind to their respective analytes. Subsequently, those iCORE-conjugated binding agents that are specifically bound to their respective analytes are enriched or isolated. In some embodiments, the iCOREs are then released, for example, by cleaving the linker connecting the iCORE to the binding agent. In some embodiments, the iCOREs are then subjected to MS analysis, for example, in an MS/MS assay, and the presence or absence, and/or the quantity of each iCORE is determined. In some embodiments, the presence or absence, and/or the quantity of each analyte is determined from the result of the MS assay. For example, in some embodiments, if an iCORE MS assay results in the detection of iCOREs G1, G3, G5-7 and G10, the presence of analytes A1, A3, A5-7, and A10, and/or the absence of analytes A2, A4-6, and A8-9 can be determined. In some embodiments, a comparison of the signal obtained for a given iCORE in the MS assay can be used to determine the quantity of the respective analyte in the sample, and/or to compare the level of the respective analytes in the sample to the level of a different analyte in the sample via MS signal comparison. For example, if the MS result obtained from a sample contacted with 10 iCOREs conjugated to 10 binding agents specifically binding to 10 analytes would represent the MS result as shown in FIG. 3, the presence of all unique fragmentation signatures of iCOREs G1-10 would indicate that all analytes A1-10 are present in the sample. In some embodiments, the similar signal level of all unique fragmentation signatures of iCOREs G1-10 may further indicate that all analytes A1-10 are present at similar levels in the sample, if the binding agent-analyte interactions are substantially similar across the analytes.

In some embodiments, a library of isobaric iCOREs is provided in which the iCOREs comprise the same sequence, for example, a set of peptide or nucleic acid iCOREs that comprise the same amino acid or nucleotide sequence, respectively, but in which the different iCOREs are isotope-labeled at different positions, for example, at different amino acid or nucleotide residues within the amino acid or nucleotide sequence.

Some aspects of iCORE technology rely on or use proven, existing technologies, for example, bead-based immuno-enrichment, photo-labile bioconjugation chemistry, direct labeling of analytes, for example, of proteins by reactive chemical moiety conjugation, and qualitative and/or quantitative mass spectrometry, for example, LC MS/MS assays. These technologies are well known to those of skill in the art and many variations and equivalents of the exemplary embodiments described herein will be apparent to the skilled artisan based on this disclosure. It will be appreciated that iCORE technology can be applied to many different analyte detection scenarios, e.g. diagnostic scenarios, as well as many different tracking scenarios. The invention is not limited in this respect.

For example, some embodiments of iCORE technology as described herein provide molecular diagnostic assays (e.g. biomarker detection, monitoring of vaccines, and HLA screening) as well as qualitative and quantitative assays for basic science research (e.g. protein expression profiling, cell profiling, tissue profiling, and metabolic profiling). For example, certain embodiments provide a library of iCORE-labeled binding agents (e.g. antibodies or antibody fragments) targeted against a panel of serum biomarkers (e.g. organ- and/or disease-specific markers) that can be used for monitoring biological processes by analyzing body fluid or tissue samples obtained from a subject (e.g. tumor evolution, host responses after drug administration, or drug metabolism). Some embodiments of iCORE technology are particularly suited for such multi-parameter studies, particularly in the diagnosis of diseases or conditions, because iCORE technology allows for increases in detection sensitivity and resolution through multiplexing, which, in turn, allows for the efficient detection of multi-parameter diagnostic signatures.

Some embodiments provide a library of chemically-active iCOREs, for example, isobaric peptide iCOREs conjugated to a reactive chemical moiety that can be utilized by an end user to encode user-defined experiments. For example, in case-and-control comparative proteomics studies, proteins from each unique condition, experiment, or subject, can be encoded (e.g., labeled) with a particular iCORE fragmentation signature. All samples can then be combined and simultaneously analyzed by LC MS/MS to determine the relative effects of the experimental conditions. The use of iCORE technology enables comparative studies at a scale precluded by current technologies and methods.

It will be appreciated by the skilled artisan that the use of iCORE technology, as described herein, is not limited to analyte detection, encoding and translation. Because iCOREs are versatile, novel MS tags that have multiple advantages over previously known MS tags, iCORE technology is amenable to adaptation to various MS tag detection technologies and diagnostic strategies. For example, iCORE technology can be used in the context of multiplexed enzyme (e.g., protease) activity profiling using MS/MS strategies, as described in PCT application PCT/US2010/000633, published as WO/2010/101628 on Oct. 9, 2010, the entire contents of which are incorporated herein by reference.

For example, iCOREs can be conjugated to a carrier, for example, a nanoparticle (e.g., a nanoworm (NW)), via a linker comprising an amino acid sequence that is cleaved by an enzyme of interest, e.g., by a protease associated with a disease. Such iCORE NWs, also sometimes referred to as pro-diagnostic reagents, can then be administered to a subject to interrogate the activity of the enzyme in the subject. In some embodiments, a set of iCOREs is provided that is linked to a carrier via different linkers targeted by different enzymes (e.g., different proteases) in a way that the activity of each protease releases one specific iCORE tag. Used in this manner, iCORE technology can be employed to interrogate the activities of a plurality of disease-associated enzymes (e.g., disease-associated proteases) in parallel in one multiplexed MS assay. In some embodiments, a set of pro-diagnostic iCORE reagents is administered to a subject suspected to exhibit an aberrant (e.g., pathogenic) level of activity of one or more enzymes (e.g., one or more proteases) to probe the activity levels of numerous proteases in one multiplexed assay. While the carrier of the prodiagnostic reagent is typically not secreted into the urine of the subject, when exposed to protease activity, the respective iCORE is cleaved from the NW and released into the urine of the subject. Urine samples are collected after a sufficient time after administration of the pro-diagnostic reagent to the subject has passed for the reagent to be exposed to enzyme activity in the subject. Urine samples are then subjected to MS/MS assays as described in more detail elsewhere herein, or in PCT/US2010/000633, published as WO/2010/101628, to detect the cleaved iCOREs and determine whether or not the subject exhibits an aberrant protease activity signature.

Protease activities that are associated with disease are well known to those of skill in the art (see, e.g., Table 1 of PCT/US2010/000633, published as WO/2010/101628, for some non-limiting examples of disease-associated enzyme activities, incorporated herein in its entirety by reference). Protease target sequences that are useful as linker sequences for iCOREs to carriers are also well known to those of skill in the art. Some exemplary iCOREs, protease-cleavable linkers, and methods for the diagnosis of diseases in a subject are described in detail herein. Additional iCOREs, linkers, and methods will be apparent to those of skill in the art based on this disclosure, and the disclosure is not limited in these aspects. As will be apparent to the skilled artisan, the use of iCORE technology in the context of multiplex protease activity assays allows for an improvement of multiplexing capabilities and increased ease of detection as compared to previously described methods.

Some embodiments provide kits of reagents described herein. For example, some embodiments provide a kit comprising a set of iCOREs, for example, isobaric peptide iCOREs, that comprises iCOREs having different fragmentation signatures. In some embodiments, the iCOREs are conjugated to a reactive chemical moiety, for example, a peptide-reactive moiety that forms a covalent bond to a peptide when contacted with such a peptide. In some embodiments, the different iCOREs in a set of iCOREs so provided are separated, thus allowing the end-user to label a particular sample, for example, a protein sample, with a specific iCORE and a different sample with a different iCORE, thus allowing subsequent mixing and simultaneous analysis if the samples in an MS assay, e.g. in an LC MS/MS assay.

In some embodiments, a kit is provided that comprises a set or library of binding agents that are conjugated to iCOREs, as described herein. In some embodiments, each binding agent binding a particular analyte is conjugated to an iCORE of a particular fragmentation signature, so that the analyte bound by the binding agent can be identified by the fragmentation signature of the iCORE.

Some aspects of this invention relate to biochemical encoding of parameters, for example, of analytes, into mass tags, for example, iCOREs. In some embodiments, the biochemical encoding of an analyte parameter, e.g., the presence of an analyte in a sample or the amount of an analyte in a sample, involves contacting the sample with a binding agent (e.g., an antibody or antibody fragment) specifically binding the analyte and bound to an iCORE the fragmentation signature is assigned to the specific analyte bound by the binding agent, isolating or enriching for those binding agent molecules that have bound the analyte, optionally, releasing the iCORE from the isolated or enriched binding agent molecules and subjecting the iCORE (released or not) to an MS assay. In other embodiments, the biochemical encoding is achieved by translating a parameter, for example, the presence of an analyte in a sample, or the identity of a cell or tissue, into an iCORE signature by tagging the sample, cell, or tissue with a unique iCORE, for example, by spiking an iCORE into the sample, or by attaching (e.g., covalently via a cleavable linker) an iCORE to a cell or tissue. In some embodiments, the biochemical encoding is carried out for multiple parameters in parallel, for example, by contacting a complex sample (e.g. a blood or tissue sample) containing or suspected to contain a plurality of analytes with a plurality of iCOREs bound to a plurality of binding agents, wherein each binding agent specifically binds a particular target analyte and is conjugated to a specific iCORE with a unique fragmentation signature. After isolation or enrichment of analyte-bound binding agents and rescue of the conjugated iCOREs from the isolated or enriched binding agents, the presence or absence as well as the relative or absolute amount of the target analytes can be determined by an MS assay, e.g., an LC MS/MS assay as described in more detail elsewhere herein.

A schematic of an exemplary biochemical encoding strategy in which the presence of a plurality of analytes in a sample is translated into iCOREs is described in FIG. 1. In some embodiments, the translation of a parameter into an iCORE comprises a step of deconvolution, for example, a step of analyte enrichment from a complex biological sample. Deconvolution can increase assay sensitivity, specificity, and/or accuracy. In some embodiments, a sample to be assessed is enriched for an analyte by contacting with an affinity agent that binds the analyte, specifically or non-specifically, and allows for enrichment of the analyte, for example, by physical separation of the bound analyte from unbound material. An affinity agent may be an agent that non-specifically binds the analyte based on a non-specific interaction, for example, a non-specific interaction based on the surface charge of the analyte. Such non-specific binding will typically result in a lower level of deconvolution of the sample than the use of an affinity agent that specifically binds the analyte, since non-specific binding is generally not restricted to the specific analyte, but also extends to other molecules of similar physiochemical properties. Alternatively, an affinity agent may also be an agent that specifically binds the analyte. For example, an affinity agent may be a binding agent, for example, an antibody or antibody fragment, that is immobilized on a solid support, such as a bead or membrane surface. Solid supports useful for the separation of materials bound to their surface from biological samples are well known to those of skill in the art, and include, but are not limited to, membranes, resins, beads, and the surface of plates, dishes and tubes.

In some embodiments, a complex sample is contacted for deconvolution with an affinity agent under conditions suitable for the affinity agents to bind the analyte(s). Typically, the sample comprises a liquid phase that is contacted with the affinity agent. In some embodiments, the affinity agent, and any analyte(s) bounds to it are subsequently removed from the sample, for example, by physical separation, or aspiration of liquid supernatant. In some embodiments, the affinity agent is washed after separation to remove remaining residue of the biological sample on the affinity agent for further deconvolution.

In some embodiments of biochemical encoding of analytes, a sample is contacted with an affinity agent or a set of affinity agents that bind(s) a set of analytes of interest, under conditions suitable for the affinity agents to bind the respective analytes, and for the analytes to become immobilized on the affinity agent. In some embodiments, the sample is then deconvoluted, for example, by washing away any unbound material. In some embodiments, the sample, deconvoluted or not, is then contacted with a set of iCOREs conjugated to binding agents that specifically bind a set of analytes under conditions suitable for the binding agents to bind their respective analytes. In some embodiments, those iCOREs conjugated to binding agents that have actually bound to an analyte are subsequently isolated or enriched, for example, by removing any unbound iCOREs and binding agents from the sample. This "rescued" set of iCOREs represents a biochemical encoding of the analytes present in the sample. In some embodiments, the iCOREs are conjugated to the binding agents via a cleavable linker, and the process of biochemical encoding of the analytes in the sample comprises a step of cleaving the linker and releasing the iCOREs from the binding agents. In some embodiments, the rescued iCOREs are subjected to an MS assay, for example, an MS/MS assay as described herein, to determine their identity and/or quantity, and thus the identity and/or quantity of the respective analytes in the sample.

It will be appreciated, that translation for biochemical encoding is not restricted to analytes, but can be applied to other parameters as well. For example, iCORE technology provides a possibility to track samples, cells, tissues, reagents, or molecules. As one example of biochemical encoding for tracking purposes, iCORE technology can be used to encode small molecule compound identities, e.g., in the context of small molecule screens. Biochemical encoding of small molecule compound identities is particularly useful in the context of large combinatorial small molecule screens, where thousands, tens of thousands, or hundreds of thousands of small molecule combinations can be tracked without the logistic problems commonly imposed by such screens. In some embodiments, each small molecule in such a screen is associated with an iCORE having a unique fragmentation signature, for example, by simply adding the iCORE to the small molecule, thus generating a composition comprising the iCORE and the small molecule. In some embodiments, the composition comprises the iCORE in the small molecule at a specific, known ratio. In some embodiments, the composition is then used in a combinatorial chemical screening assay, for example, in an assay in which multiple combinations of multiple small molecule compounds in multiple dilution ratios are tested for a desired effect. The desired effect may be any effect for which small molecule libraries are currently being screened, including, but not limited to, a biological effect, such as the induction of cell death in a cancer cell line, the inhibition of aberrant cell proliferation, the induction or repression of the expression of a specific gene, or the induction of epigenetic reprogramming. Many other desired effects for which small molecule compound libraries can be screened will be apparent to those skilled in the art, and the invention is not limited in this respect.

Biochemical encoding of each small molecule with a unique iCORE allows for the identification and/or the quantification of each small molecule compound in a mixture or dilution series of small molecule compounds by subjecting the mixture or dilution to an MS assay. Any specific iCORE detected in the MS assay can then be traced back to the particular small molecule compound it encodes. If the concentration of the small molecule compound was also encoded, for example, by generating the original iCORE/small molecule compound mixture used in the screen to comprise a particular ratio of the two components, the intensity of signal detected for the specific iCORE can be used to determine the concentration of the small molecule compound in the mixture or dilution of interest.

For example, a simple combinatorial small molecule screening assay may comprise a combinatorial dilution series screen of 10 small molecule compounds (SMC 1-10) at 10 different dilutions (D 1-10), in which all possible mixtures of any or all of the ten compounds at any possible dilution ratios of the compounds are to be tested. For example, ten potentially synergistic cancer drug candidates might be tested this way for their efficiency to kill cancer cells, e.g., to investigate which combination of these candidates at which ratio effects the greatest synergy or the greatest biological effect. Even such a simple screen poses a significant logistic challenge in view of the necessity to map the contents and drug concentrations of multiple thousands of samples. Biochemical encoding of the drug candidates with only 10 iCOREs (e.g., iCORE G1-10, assigned to CD1-10, respectively) circumvents the problems associated with this logistical undertaking. For example, each drug candidate could be spiked with one of the iCOREs at a specific, known ratio of drug candidates and iCORE at the beginning of the experiment. The generation of dilution series and drug candidate mixtures can then be carried out as usual, but without the necessity to keep track of all pipetting steps and the resulting sample contents. After screen readout, for example after the detection of a sample showing the desired biological effect, the supernatant of the sample can be obtained, and subjected to an MS assay. The MS assay will not only identify the presence or absence of each of the drug candidates, but can also be used to determine the ratios of the drug candidates identifies to be present in the sample based on the known iCORE/drug candidate ratios in the original spiked mixture at the beginning of the experiment.

For example, if in the hypothetical screen described above, the MS assay would detect the presence of iCOREs 1, 4, and 7 at a ratio of 1:10:2 in a sample of interest, the presence of drug candidates 1, 4, and 7 can be inferred. It can further be inferred that drug candidate 1 was present at the lowest concentration (e.g., D10), drug candidate 4 at the highest concentration (e.g., D1), and drug candidate 7 at the second lowest concentration (e.g., D9) of the dilution series. If molar ratios of iCORE and drug candidate were known in the original spiked sample at the beginning of the experiment, a determination of the concentration of each drug candidate may be possible directly from the MS data, without the need to track dilutions.

Aside from circumventing the necessity to track thousands of pipetting steps, drug candidate tracking with iCORE biochemical encoding during combinatorial screening allows for an assessment of the actual conditions in the sample of interest, which, for example, avoids erroneous results caused by pipetting errors. The particular iCOREs used for biochemical encoding and drug screening should be chosen to not interfere with the process being probed. Peptide iCOREs are suitable for a variety of biochemical encoding applications during drug screening, since the peptides are inert to most biochemical processes. It will be apparent to those of skill in the art, that, depending on the length and the conditions encountered by the iCOREs during the drug screening process, useful iCOREs will have to exhibit sufficient stability to withstand the conditions encountered. In some embodiments, peptide iCOREs with improved stability are generated by using non-naturally occurring amino acid residues and/or peptides comprising non-hydrolyzable bonds. Peptides exhibiting increased stability, for example, peptides comprising non-hydrolyzable bonds, are well known to those of skill in the art, and the skilled artisan will be able to readily ascertain methods and reagents for the generation.

In some embodiments, a method for tracking a cell, cell population, tissue, or compound by biochemical encoding via iCOREs is provided. In some such embodiments, the method comprises conjugating a unique iCORE to a cell, cell population, or tissue, for example, by contacting the cell, population of cells, or tissue with an iCORE under conditions suitable for the iCORE to bind to the cell, population of cells, or tissue. In some embodiments, an iCORE covalently bound to a binding agent is used to achieve this conjugation. For example, in some embodiments, the iCORE is bound to a binding agent, for example, an antibody or antibody fragment, that specifically binds a surface marker, for example, a surface protein or polysaccharide marker of the cell, population of cells, or tissue. In other embodiments, a cell, cell population, tissue, or compound is contacted with an iCORE comprising or conjugated to a reactive chemical moiety under conditions suitable for the reactive chemical moiety to form a covalent bond with a surface marker of the cell, cell population, tissue, or with the compound. In some embodiments, the compound is a compound that is used in the generation of or can be embedded into a hydrogel, for example, a PEG hydrogel as described in FIG. 7. In some embodiments, the hydrogel is used in the generation of beads or in the production of a scaffold for tissue engineering, e.g., as a substrate for growing artificial, engineered tissues, for example, engineered organs, such as micro-livers. The result of this approach is the production of iCORE-tagged beads or scaffolds and, if such scaffolds are used for the generation of engineered organs, iCORE-tagged organs. In some embodiments, a plurality of different iCORE-tagged beads or engineered organs is subjected to different experimental conditions, e.g., the exposure to different growth factors and/or small molecule compounds, or growth factor and/or small molecule compound combinations at different dilutions, and those beads or engineered organs exhibiting a desired phenotype or parameter at the end of the experiment is identified by rescuing the iCORE tag from the desired bead or organ and subjecting it to an MS assay, e.g., an LC MS/MS assay.

In some embodiments, a set or library of iCOREs is provided that comprise or is conjugated to a reactive chemical group that can form a covalent bond to a peptide. Such reactive chemical groups are known to those of skill in the art and include, but are not limited to those reactive chemical groups conjugated or comprised in mass tags used in iTRAQ assays. In some embodiments, methods for the use of such peptide-binding iCOREs are provided, for example for the simultaneous analysis of proteins in samples of different origin, for example, blood or tissue samples from different subjects. In some embodiments, protein samples obtained from different subjects, for example, from different experimental mice, or from different tumor biopsies, are conjugated to a unique iCORE each. In some embodiments, a plurality of such iCORE-labeled samples is then pooled and simultaneously analyzed in an MS assay, for example, an LC MS/MS assay. In some embodiments, the data obtained from such simultaneous proteomics experiments is used to compare protein expression levels across a large number of samples, for example, across at least 10, at least 15, at least, 20, at least 25, at least 30, at least 40, at least 50, at least 60, at least 70, at least 80, at least 90, at least 100, at least 150, at least 200, at least 250, at least 500, at least 750, at least 1000, or more than 1000 samples. The large number of possible unique fragmentation signatures that can be obtained from a single iCORE base sequence, for example, from a glu-fib amino acid sequence, allows for the unique labeling and subsequent simultaneous analysis of such sample numbers, which is far beyond the multiplexing capabilities of the currently available technologies, e.g., iTRAQ.

Some aspects of this invention provide multiplexed diagnostic assays using iCORE technology. Currently, many molecular biomarkers are known that are correlated with, and, thus, indicative of a disease or condition in a subject. For example, a plethora of molecular biomarkers have been reported for diseases such as cancer, infectious disease, cardiovascular disease, renal disease, autoimmune disease, toxic states, and for the detection of certain side effects of drugs. Current diagnostic assays typically focus on one or only a few biomarkers to detect a specific disease or condition. For example, some cancers, such as prostate and ovarian cancer are monitored by use of single biomarkers in the blood of subjects diagnosed or suspected to have such a cancer. Such diagnostic techniques are achieved, for instance using fluorescence detection of molecular markers which are activated in a particular disease state. Other diagnostic techniques to monitor molecules include the use of gene arrays for stratifying breast cancer patients via unique signatures (Sotiriou C., Piccart, M. J., Taking gene-expression profiling to the clinic: when will molecular signatures become relevant to patient care?, Nat. Rev. Cancer, 7, 534-553, 2007) and sequencing target gene mutations to uncover the molecular lesions that predict glioblastoma response to EGFR kinase inhibitors (Mellinghoff, I. et al., Molecular Determinants of the response of glioblastomas to EGFR Kinase Inhibitors, NEJM, 353, 16, 2005). Both of the foregoing references are incorporated herein in their entirety by reference for their disclosure of diagnostic biomarkers.

Some of the reagents and methods for multiplex analyte detection and quantification in complex samples, for example, in a body fluid or tissue sample obtained from a subject, allow for the sensitive and accurate assessment of multiple biomarkers simultaneously, thus providing an avenue for the generation of clinically relevant multi-parameter biomarker profiles of a single disease or condition or of a plurality of diseases or conditions from such a sample.

In some embodiments, iCORE technology as described herein is used to assess a plurality of biomarkers, e.g., the presence or absence or the quantity of an analyte in a biological sample obtained from a subject, such as a body fluid (e.g. blood, serum, urine, cerebrospinal fluid, or lymph) or tissue (e.g., tumor, malignant, neoplastic, hyperplastic, liver, kidney, lung, muscle, lymph node, or brain tissue). In some embodiments, the plurality of biomarkers comprises a panel of biomarkers known to be associated with a particular disease or condition.

In some embodiments, a diagnostic iCORE method is provided. In some embodiments, the method comprises obtaining a sample from a subject. In some embodiments, the subject is a human subject. In some embodiments, the subject is a non-human mammal. In some embodiments, the method comprises a deconvolution step in which target analytes are isolated or enriched, for example, by a deconvolution method as described elsewhere herein. In some embodiments, the method comprises contacting the sample, whether deconvoluted or not, with a set or library of iCOREs conjugated to a set of binding agents specifically binding to the target analytes, as described herein, under conditions suitable for the iCORE-conjugated binding agents to bind their respective target ligands. In some embodiments, the method comprises a step of isolating or enriching the bound iCORE-conjugated binding agents, for example, by washing off unbound binding agents. In some embodiments, the method comprises rescuing the iCOREs conjugated to the analyte-binding binding agents, for example, by cleavage of a linker connecting the iCOREs to the binding agents, as described elsewhere herein. In some embodiments, the method comprises subjecting the rescued iCOREs to an MS/MS assay, for example, an MS/MS assay as described herein. In some embodiments, the method further comprises determining the signal obtained from each specific iCORE in the sample based on the results of the MS/MS assay. In some embodiments, the method comprises determining the presence or absence of the analyte represented or identified by the specific iCORE based on whether or not a signal was obtained in the MS/MS assay that identified the specific iCORE. In some embodiments, the method comprises quantifying the amount or concentration of the analyte in the sample, or relative to the amount or concentration of other analytes in the sample, or relative to the amount or concentration of the same analyte in a different sample, for example, a reference or control sample, by quantifying the signal obtained from the specific iCORE in the MS/MS assay.

In some embodiments, the assessment of multiple biomarkers in a single diagnostic assay increases the specificity, sensitivity, and/or accuracy of the assessment of the biomarkers and/or the diagnosis inferred from the assay. In some embodiments, the iCORE MS/MS assay also comprises the assessment of a control marker, for example, of an analyte or a set of analytes that are known to be virtually constant across healthy and diseased states or across individuals. There are many protein biomarkers present in blood that are useful for assessment by iCORE MS/MS analyses. For example, in certain embodiments for ovarian cancer, 5-20 protein or peptide biomarkers may be monitored (see, e.g., Petricoin, E., et. Al., Use of proteomic patterns in serum to identify ovarian cancer, Lancet, 359, 572, 2002, incorporated in its entirety by reference for disclosure of ovarian cancer biomarkers). Serum cytokines, of which IFN-gamma and TNF-alpha are normally classified, including, but not limited to, IL-1, 11-2, 11-4, 11-5, 11-6, 11-10, 11-12, 11-13, 11-17, 11-21, 11-23, MCP-1, TGF-beta, TNF-beta, TWEAK, GM-CSF, and Granzyme B, are useful for monitoring inflammatory processes involved in cancer, as well as host responses to vaccines, and infectious diseases. It will be apparent to those of skill in the art that the biomarkers described herein are for illustration only and not meant to limit the invention in this respect. Any biomarker, and particularly, any peptide or protein biomarker can be assessed by iCORE MS/MS assays provided herein, and the invention is not limited in this respect.

In some embodiments, iCORE technology is used in the context of personalized medicine. For example, in some embodiments, a clinical intervention, e.g., a drug, a treatment schedule, or a surgical intervention, is chosen from a group of such interventions, based on the results of an iCORE assay performed on a sample obtained from the subject, for example, a blood or tissue sample assessed for a set of biomarkers, or based on analyte or enzymatic activity signatures produced from an in vivo iCORE assay, by methods described herein.

In some embodiments, iCORE technology is used to monitor a subject's response to a treatment. For example, in some embodiments, iCORE assays are performed repeatedly during the treatment of a diseased subject, for example, in order to determine whether the assessed biomarkers are approaching desired values, for example, values typically associated with a state of health. In some embodiments, a treatment regimen may be adjusted based on the results of an iCORE assay performed during the course of the treatment, for example, in order to increase the efficacy of the treatment or to decrease the dosage of a drug used to the minimal effective dose in order to avoid undesired side effects.

In some embodiments, iCORE technology is used in clinical trials of novel drugs and drug candidates. Multiplex iCORE technology allows for the assessment of a variety of disease-associated biomarkers, and, in some embodiments, also for the monitoring of a plurality of base parameters, e.g. blood cholesterol, blood triacylglycerides, ketone bodies, and so forth, in a subject during a clinical trial. This allows for the comprehensive monitoring of multiple metabolic pathways during a clinical trial and the detection of side effects that may be non-symptomatic during the trail.

Mass spectrometry (MS) assays are well known to those of skill in the art. Of particular use in the context of some embodiments of iCORE technology and biochemical encoding described herein are tandem mass spectrometry (MS/MS) assays.

Tandem mass spectrometry (MS/MS) is used to produce structural information about a compound by fragmenting specific sample ions inside the mass spectrometer and identifying the resulting fragment ions. Tandem mass spectrometry allows for specific iCOREs to be detected in complex mixtures of iCOREs, for example, in complex sets or libraries of iCOREs on account of their unique fragmentation signature, which results in a specific and characteristic fragmentation pattern.

MS/MS assays typically comprise two or more MS steps with some form of fragmentation taking place between the steps. A tandem mass spectrometer typically comprises more than one analyzer, for example, two analyzers. In some embodiments, the analyzers are separated by a collision cell into which an inert gas (e.g. argon, xenon) is admitted to collide with the selected sample ions and bring about their fragmentation. However, some MS/MS assays can also be performed on certain single analyzer mass spectrometers such as ion trap and time-of-flight instruments, for example, by using a post-source decay experiment to effect the fragmentation of sample ions.

In some embodiments, because both the masses of the parent peptide as well as the reporter ions of individual iCOREs are known, the detection and quantification of the iCOREs in a complex sample can be achieved by selected reaction monitoring (SRM), also referred to as multiple reaction monitoring (MRM) (see, e.g., Lange, V., Picotti, P., Domon, B., Aebersold, R., *Selected reaction monitoring for quantitative proteomics: a tutorial*, Molecular Systems Biology 4:222, 2008, the entire contents of which are incorporated herein by reference). A typical SRM experiment is enabled by the unique capability of a triple quadrupole (QQQ) MS for quantitative analysis in which the first and third quadrupoles act as filters to specifically select predefined m/z values corresponding to the peptide ion and a specific fragment ion of the peptide.

For example, in some embodiments, for iCOREs based on 10-plex glu-fib iCORE library (G10), the first quadrupole serves to collect the parent Glu-fib peptide (e.g. 789.85 m/z doubly charged), the second quadrupole fragments, while the third quadrupole acts to filter an individual reporter ion (e.g. 683.3 m/z) (FIG. 14). In some embodiments, such precursor/fragment ion 'transitions' (e.g. 789.85 to 683.3 m/z) are monitored over time, which results in high selectivity and sensitivity, as co-eluting background ions are filtered out effectively with this approach.

In some QQQ embodiments, unlike other MS techniques (e.g. Q-TOF), no full mass spectra are recorded and the non-scanning nature of QQQ analysis translates into 1-2 orders of magnitude increase in sensitivity over full scan techniques. Because isotopic amino acids can be selectively incorporated by the user to generate unique fragment ions with iCORE encoding, multiple unique precursor/fragment ion transitions can be designed into a family of iCOREs. For example, in FIGS. 2 and 3, the transitions are defined from the precursor peptide to the y7 family of fragment ions, while in FIG. 13c,d,e and FIG. 14, the transitions are defined form the precursor peptide to the y6 family of fragment ions.

In some embodiments, the first analyzer is used to select user-specified sample ions arising from a particular iCORE. These chosen iCORE ions, for example, the ions of the glu-fib iCOREs described herein, pass into the collision cell, are bombarded by the gas molecules which cause fragment ions to be formed, and these fragment ions are then separated according to their mass to charge ratios, by the second analyzer. The fragment ions arise directly from the parent iCORE ions, and thus produce a fingerprint pattern specific to the compound under investigation. (see FIG. 3 I. for data obtained in the first round of MS from a library of glu-fib iCOREs; and FIG. 3 II. for data obtained in the second round (after fragmentation) from the same library).

In some embodiments, the first analyzer allows the transmission of all iCORE ions, whilst the second analyzer is set to monitor specific iCORE fragment ions, for example, the glu-fib iCORE $y_7$ ions, as described in FIGS. 2 and 3, which are generated by bombardment of the sample ions with the collision gas in the collision cell. This strategy is particularly useful in embodiments, where a set of isobaric iCOREs is used, which fragment to produce distinct, but similar fragment ions. Using this strategy allows for monitoring only the part of the spectrum spanning the particular masses of the iCORE ions, e.g. the spectrum from about 812 to about 822 Da in the example using iCOREs G1-G10 as described in FIG. 3. This, in turn allows for a drastic reduction in scanning time, because the rest of the spectrum can be ignored.

In some embodiments, both analyzers are static and only specific parent ions are transmitted through the first analyzer and only specific fragments arising from these parent ions are measured by the second analyzer. The parent ion properties of any iCORE provided herein can be calculated according to methods well known to those of skill in the art. Additionally, any iCORE can be tested for its specific ionization and fragmentation signature in an MS/MS test run. Since the structure and MS/MS behavior of each iCORE is either known or can readily be calculated or established, this type of MS/MS assay can be employed to determine the presence or absence of a specific iCORE ion in a matrix or fragment ions, for example, a matrix of fragment ions originating from a complex isobaric iCORE library in a multiplex iCORE assay as provided by aspects of this invention.

In some embodiments, peptide iCOREs, sets or libraries of peptide iCOREs, and methods for the use of peptide iCOREs are provided. It is known to those of skill in the art that peptides fragment in a reasonably well-documented manner in MS/MS assays (see, e.g., P. Roepstorrf, J. Fohlmann, Biomed. Mass Spectrom., 1984, 11, 601; and R. S. Johnson, K. Biemann, Biomed. Environ. Mass Spectrom., 1989, 18, 945; the entire contents of which are incorporated herein by reference). In some embodiments, the peptides fragment along the peptide backbone (see, e.g., A. E. Ashcroft, P. J. Derrick in "Mass Spectrometry of Peptides" ed. D. M. Desiderio, CRC Press, Fla., 1990; the entire contents of which are incorporated herein by reference).

There are three different types of bonds that can fragment along the amino acid backbone: the NH—CH, CH—CO, and CO—NH bonds. Each bond breakage gives rise to two species, one neutral and the other one charged, and only the charged species is monitored by the mass spectrometer. The charge can stay on either of the two fragments depending on the chemistry and relative proton affinity of the two species. Hence there are six possible fragment ions for each amino acid residue and these are labeled as a, b, and c ions, and x, y, and z ions, with the a, b, and c ions having the charge retained on the N-terminal fragment, and the x, y, and z ions having the charge retained on the C-terminal fragment. The most common fragmentation occurs at the CO—NH bonds of the peptide backbone, which give rise to the b and/or the y ions. FIG. 2 shows an exemplary nomenclature of 13 y-ions originating from a parental glu-fib iCORE sequence. Since the mass difference of adjacent fragment ions correlates to the mass of the respective amino acid residue missing in the shorter ion, e.g., the difference in the mass of the $y_9$ and $y_{10}$ ions is the mass of the D residue present in the $y_{10}$ but not the $y_9$ ion, the peaks representing each y ion can be identified. In the exemplary MS/MS experiment shown in FIG. 2, y ions $y_3$-$y_{11}$ could unambiguously be identified.

An example of an MS/MS spectrum obtained from a set of 10 isobaric iCOREs is illustrated in FIG. 3. The first round of MS generated one single peak, consistent with the isobaric character of the iCOREs (FIG. 3 I.). The iCORE ions were fragmented and the size of the fragments analyzed by the second analyzer to produce the MS/MS spectrum depicted in FIG. 3. II.). The iCOREs fragmented predominantly at the CO—NH bonds ions y ions $y_3$-$y_{11}$ could unambiguously be identified. A close-up of the region spanning the mass of the possible $y_7$ ions shows that all ten iCOREs were detected with highly similar signal strength, indicating that all fragment ions were present at about the same concentration. This indicates that there is no fragmentation bias in iCOREs of different fragmentation signature, which allows iCORE technology to be used in sensitive analyte quantification MS/MS assays.

In some embodiments, the iCOREs are polynucleotides or polysaccharides. MS/MS-based assays oligonucleotide and oligosaccharide fragment identification are well known to those of skill in the art and are similar to those used in peptide MS/MS assays. For a general overview of MS/MS assays useful for the detection and/or quantification of iCOREs provided herein, for example, of peptide, oligonucleotide, and/or oligosaccharide iCOREs, see, e.g., S. Pomerantz, J. A. Kowalak, J. A. McClosky, J. Amer. Soc. Mass Spectrom., 1993, 4, 204; "An Introduction to Biological Mass Spectrometry", C. Dass, Wiley, USA, 2002; "The Expanding Role of Mass Spectrometry in Biotechnology", G. Siuzdak, MCC Press, San Diego, 2004; "Ionization Methods in Organic Mass Spectrometry", A. E. Ashcroft, Analytical Monograph, Royal Society of Chemistry, U K, 1997; www.astbury.leeds.ac.uk (A. E. Ashcroft's MS web pages and tutorial); Chapter 9, pages 415-452 of "Mass Spectrometry: A Textbook" by Jurgen H. Gross, Springer; 2nd ed. edition (Mar. 1, 2011), ISBN-10: 9783642107092; U.S. Pat. Nos. 5,885,775; 7,412,332; 6,597,996; and "Mass Spectrometry: Clinical and Biomedical Applications Volume 1 (Modern Analytical Chemistry)" by Dominic M. Desiderio, Springer; 1 edition (Jan. 31, 1993), ISBN-13: 978-3642107092; the entire contents of all of which are incorporated herein by reference).

Some aspects of this invention provides kits of reagents useful for carrying out iCORE-based MS assays. Typically, a kit comprises a container housing an iCORE reagent, or a set or library of such reagents, as described herein. In some embodiments, a kit also includes instructions or labels describing the use of the iCORE reagents.

In some embodiments, iCORE reagents described herein, for example, iCOREs conjugated to a reactive chemical moiety, or iCOREs conjugated to a binding agent specifically binding a target ligand, or sets or libraries of such iCORE reagents, are assembled into kits for clinical and/or research applications. A kit may be designed to facilitate use of the methods described herein by clinicians and/or researches and can take many forms. Each of the iCORE reagents comprised in the kit, where applicable, may be provided in liquid form (e.g., in solution), or in solid form, (e.g., a dry powder). A kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. In some embodiments, a kit comprising iCORE reagents as provided herein further comprises additional components that are useful in performing the iCORE-based assays provided herein. Such additional components may include, but are not limited to deconvolution reagents (e.g., binding agents specifically binding the set of analytes targeted by the iCORE reagents comprised in the kit, for example, immobilized to a solid support, such as beads (e.g., magnetic beads), a membrane, glass slide, resin, or plastic vessel surface), buffers (e.g., wash buffers, binding buffers), and enzymes (e.g., proteases cutting a cleavable linker connecting iCOREs to binding reagents).

EXAMPLES

Example 1: Materials and Methods

Peptide and Ab Peptide Synthesis.

All peptides were synthesized by Fmoc chemistry in house by the biopolymers facility at the Swanson Biotechnology Center (MIT). Isotope-labeled amino acids were purchased from Cambridge Isotopes. The photosensitive linker (3-Nα-Fmoc-Amino-3-(2-nitrophenyl)propionic acid) was purchased from Advanced Chemtech. Detection antibodies against human IFN-gamma and TNF-alpha (eBioscience, clones 4S.B3 and Mab11) were first reacted with SIA (Pierce) at a 50:1 mole ratio. Following removal of excess SIA, peptides were incubated with Abs at a 20:1 mole ratio. Excess peptides were removed by size filtration spin filters (30 k mwco, Amicon).

Ab-Bead Synthesis.

Tosyl-activated magnetic beads (Myone, Invitrogen) were reacted with anti-human IFN-gamma and anti-human TNF-alpha (eBioscience, clones NIB42 and Mab1 respectively) according to manufacturer's instructions. Briefly, 1 mg of either antibody was buffered exchange into borate buffer (0.1M Sodium borate, pH 9.0) prior to incubation with the beads in conjugation buffer (0.1M Borate, 1M ammonium sulphate, pH 9.0). After overnight incubation at 37° C., remaining tosyl groups were saturated by incubating the beads in 1M tris. The Ab-labeled beads were stored in PBS prior to experiments.

Serum Assays.

Recombinant human IFN-gamma (eBioscience) was spiked into 10% bovine serum in PBS. This solution was then incubated with anti-IFN-gamma-beads for 1 hour at 37° C. The beads were then washed twice with PBS before incubation with an equimolar solution of iCORE-labeled IFN-g and TNF-a for another hour at 37° C. After excess antibodies were removed by washing with 0.1% BSA PBS, the bound antigens and antibodies were eluted in 5% acetic acid. The solution was then exposed to UV light (365 nm) for 30 min. (CL-1000, UVP) to liberate the photocaged iCORE codes into solution. The sample was then analyzed by LC MS/MS.

Nanomaterial Synthesis.

Nanoworms were synthesized according to previously published protocols.[25] Peptides were synthesized at MIT (Swanson Biotechnology Center); isotopically labeled Fmoc amino acids were purchased from Cambridge Isotopes and 3-Na-Fmoc-Amino-3-(2-nitrophenyl)propionic acid from Advanced Chemtech. Amine-terminated NWs were first reacted with Vivotag 680 (Perkin Elmer) to enable in vivo imaging, before reacted with SIA (Pierce) to introduce sulfhydryl-reactive handles. Cysteine-peptides and PEG-SH were then mixed with NWs overnight at room temperature (95:20:1 molar ratio respectively) and excess peptides were removed by size filtration. Peptide-NW stock solutions were stored in PBS at 4° C.

In Vitro Protease Assays.

For substrate screening, Fl-peptide-NWs (2.5 μM by peptide) were mixed with recombinant MMP-2/8/9 (R&D Systems), MMP-7/14 (AnaSpec, Inc.), Thrombin, Tissue Factor, Factor Xa, or Cathepsin B (Haematologic Technologies, Inc.) in a 96-well plate at 37° C. in activity buffers according to manufacturer's instructions and monitored with a microplate reader (SpectroMax Gemini EM). For MS analysis, equimolar iCORE-encoded NWs (Table) were incubated with proteases for 2.5 hrs at 37° C. Cleavage fragments were purified from NWs by size filtration before UV treatment (365 nm, CL-1000 UV crosslinker, UVP). Reporters were then dried by speed vacuum centrifuge and stored at 4° C.

In vivo imaging. All animal work was approved by the committee on animal care (MIT, protocol #0408-038-11). FVB/NJ mice (Jackson Labs) were fed with 0.1% w/w DDC (Sigma) rodent chow for three weeks (Research Diets). Fibrotic and age control animals were i.v. infused with VivoTag-680 labeled reagents and visualized by IVIS imaging (Xenogen). For tumor xenografts, LS 174T cancer cells lines were maintained in 10% FBS EMEM and inoculated s.c. (5×10⁶/flank) in NU/NU mice (Charles River) prior to imaging.

Characterization of Models.

For in situ zymography, fibrotic sections were covered with 90 µl solution of 0.5% w/v low melt agarose (Sigma) in MMP activation buffer (50 mM Tris, 150 NaCl, 5 mM CaCl2, 0.025% Brij 35, pH 7.5) with 10 µl of DQ-gelation (1 mg/ml, Invitrogen) and Hoechst dye at 37° C. Slides were solidified at 4° C. and then incubated at room temperature overnight to promote gelation proteolysis by tissue proteases. To quantify hepatic collagen, tissue from the right and left lobes (250-300 mg) were hydrolyzed in 5 ml of 6 N HCl at 110° C. for 16 hours followed by hydroxyproline quantification as previously described.[43] To quantify CEA, blood was collected from tumor animals into Capiject microtubes (Terumo) to isolate serum before ELISA analysis (Calbiotech). For immunofluorescence analysis, equimolar NW cocktails (5 µM/peptide) were administered in Fibrotic FVB/NJ or tumor bearing Nude mice. After perfusion, livers or tumors were fixed in 4% PFA, froze for sectioning, and stained for F4/80 (AbD Serotec), MMP-9 (R&D Biosystems), CD31 (Santa Cruz Biotechnologies) and/or FITC (Genetex) before analyzed by fluorescence microscopy (Nikon Eclipse Ti).

Collection of Urinary Peptides.

Mice were intravenously infused with 200 µl of PBS containing equimolar NW cocktails (5 µM per peptide) with EDTA-free protease inhibitor tablets (Roche) to isolate MMP activity. Mice were placed over 96-well plates surrounded by cylindrical sleeves for urine collection. To prevent further reporter degradation, voided samples were spiked with EDTA+ complete protease inhibitors (Roche) immediately after collection. To quantify urinary fluorescence, 2 µL of each sample was incubated with magnetic beads (Dynal) coated with α-FITC antibodies (Genetex) in 50 µl binding buffer (100 nM NH₄OAc, 0.01% CHAPS) for 1 hr at 37° C., washed twice with 100 mM NH₄OAc, and eluted twice with 15 µl of 5% acetic acid. Samples were neutralized with 2 M Tris and quantified by microplate fluorimetry. For iCORE analysis, samples were irradiated with UV for 30 min. before TCA precipitation (20% final volume) to remove proteins. Soluble fractions were applied to C18 reverse phase columns (Nest Group) and eluted via step gradients of 20% ACN increments in 0.1% formic acid. 60% ACN fractions containing Glu-fib peptides were collected and dried by vacuum centrifuge.

Lc Ms/Ms Analyses.

Peptide samples were reconstituted in 5% ACN, 0.1% formic acid and analyzed at MIT or the Taplin MS facility (Harvard Medical School). At MIT, peptides were captured and eluted from a C18 nanoflow HPLC column (75 µm internal diameter Magic C18 AQ, Michrom BioResources, Inc.) at a flow rate of 300 nL/min using water-acetonitrile solvent system with 0.1% formic acid. ESI mass spectrometry was carried out on a QSTAR Elite QTOF mass spectrometer (AB Sciex). At Harvard, samples are reconstituted in 2.5% ACN, 0.1% formic acid. Samples are injected using a Famos autosampler (LC Packings) into an Agilent 1100 HPLC prior to mass analysis on a LTQ-Orbitrap (Thermo Electron). To account for discrepancies in urine volumes and concentration, peak intensities of individual reporters were scaled relative to its respective total iCORE ion current before normalization against control samples to account for technical and age-related variations.

Statistical Analyses.

Pearson's correlation coefficients between different protease profiles were calculated with MatLAB. ANOVA analyses were calculated with GraphPad 5.0 (Prism). For ROC analysis, risk score functions were first estimated by logistic regression on individual biomarkers followed by ROC curve analyses of single or biomarker combinations (SigmaPlot).

Example 2: Detection of TNF-Alpha and IFN-Gamma in a Liquid Sample

A liquid sample comprising of recombinant human IFN-gamma spiked into 10% bovine serum to simulate a complex biological sample was made. As shown in FIG. 1a, the sample was first deconvoluted by contacting the sample with antibodies conjugated to the surface of beads. Specific binding to anti-human-TNF-alpha and anti-human-IFN-gamma antibodies bound to the surface of the beads resulted in immobilization of the target analyte IFN-gamma on the bead surface. The beads were then separated from the liquid sample by a magnet to remove the liquid phase and any unbound materials comprised in any sample residue remaining on the beads were washed away from the beads by washing the beads with a wash buffer. The immobilized analytes bound to the binding agents on the bead surface were then contacted with another set of antibodies against TNF-a and IFN-g that were conjugated to a set of iCOREs via a photocleavable linker ($dE^{+3}G^{+6}$V-dN-dD-dN-dE-dE-G-F-F-dS-A-dR-(ANP)-K(FAM)-G-G-C (SEQ ID NO: 37), $dE^{+2}G^{+6}$V-dN-dD-dN-dE-dE-G-F-F-dS-$^{+1}$A-dR-(ANP)-K(FAM)-G-G-C (SEQ ID NO: 37), respectively).

Figure 1B:
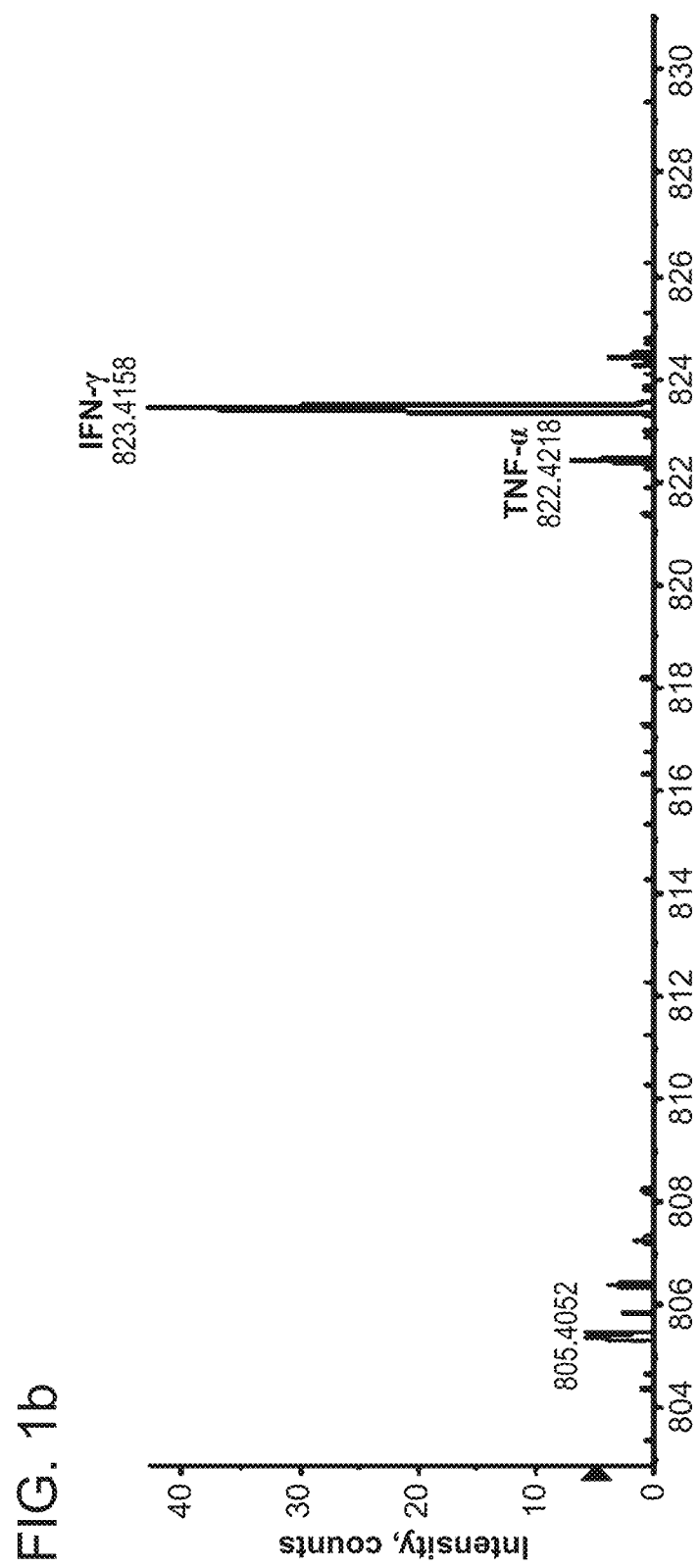

In this experiment, the set comprised two antibodies, one specifically binding IFN-gamma and the other specifically binding TNF-alpha. Both antibodies were conjugated to isobaric iCOREs, with the iCOREs bound to the antibodies binding IFN-gamma having a different fragmentation signature than the iCOREs bound to the antibodies binding TNF-alpha. Any unbound antibodies were then removed from the beads by washing the beads with wash buffer. The beads were then incubated in a stripping solution to elute the bound material, and the resulting solution collected following removal of beads by a magnet. The photocleavable linkers were then cleaved by exposure to UV light. The iCOREs rescued in this manner were then subjected to an LC MS/MS assay. FIG. 1b shows the resulting peaks of the second round MS (after fragmentation). The target analyte IFN-gamma was detected in the sample while endogenous levels of TNF-alpha, or non-specific binding contributed to the first peak. Because the iCOREs were isobaric, the signal intensity of each iCORE can directly be translated into a relative abundance of the target analyte. Accordingly, IFN-gamma was far more abundant than TNF-alpha in the sample analyzed, representing a robust signal to noise of approximately 10.

Example 3: Utilization of a Canonical Peak from Glu-Fib MS/MS Spectra as a Reporter Glu-fib was evaluated for its usefulness as a base sequence for the generation of an isobaric iCORE library. Glu-fib is a 13 amino acid peptide of the sequence EGVND-NEEGFFSAR (SEQ ID NO: 1). The fragmentation spectrum resulting from collision induced disassociation results in the generation of y-type ions. FIG. 2 is a typical spectrum to illustrate the resulting y-type ions (y1-y13) and their relative intensities.

The propensity of glu-fib to fragment along certain peptide bonds was exploited to construct 10 mass codes centered on the $y_7$ 'reporter' ion (EGFFSAR (SEQ ID NO: 6)) by enriching the truncated sequence with heavy amino acids to produce variants differentiated by 1 Da each. This introduced mass shift is then compensated by isotope enrichment within the 'balance' fragment (EGVNDNE (SEQ ID NO: 7)). As a result, each peptide is characterized by an identical nominal mass and a distinct $y_7$ fragment ion. Thus this iCORE set is isobaric, with a shared parent mass of 1579.68 Da. The mass of the $b_7$ fragment (balance) was calculated for each balance as $M_{b7(i)}=(M_{b7}+n)-i$ and the mass of each $y_7$-fragment as $M_{y7(i)}=(M_{y7}+0$, with $M_{b7}=767.3$ and $M_{y7}=812.38$. The calculated masses of four iCOREs of the set are given in the table on the lower right of FIG. 2. The set of isobaric iCOREs was then subjected to an MS/MS assay. The data obtained is shown in the MS/MS graph in FIG. 3.

Example 4: MS/MS Data from Isobaric iCORE Libraries

A 10-plex library of glu-fib iCOREs was subjected to an MS/MS assay. The results are depicted in FIG. 3. The upper panel of the figure provides the sequences and fragmentation signatures of the iCOREs in the set (iCOREs G1, G2, G3, G4, G5, G6, G7, G8, G9, and G10). The upper panel also shows the extracted ion chromatograph obtained from the 10-plex iCORE library (G1-G10) after the first round of MS. Only one peak was observed (m/z=789.7-790.0). Accordingly, each iCORE is mass indistinguishable from the multiplexed set as well as undifferentiable by chromatography, which, in some embodiments, is beneficial for quantification, which is consistent with the calculations in Example 3. The middle panel of FIG. 3 shows MS/MS results following fragmentation of the peak observed in the upper panel. The results demonstrate that, also consistent with the observations of Example 3, y-ions $y_3$-$y_{11}$ could be identified. Importantly, magnification of the m/z window around the predicted m/z values of the $y_7$ fragmentation ions generated revealed individual, distinguishable peaks corresponding to individual iCORE fragmentation signatures (lower panel). Relative quantification of the signals obtained for G1-G10 revealed that the relative representation of the iCOREs in the original sample (equal amounts of each iCORE) was closely mirrored in the peak pattern obtained, indicating that the method is not only fit for qualitative detection (absence/presence of an analyte), but also for quantitative and comparative quantitative studies.

Example 5: Quantitative iCORE MS/MS Assays

Figure 4:
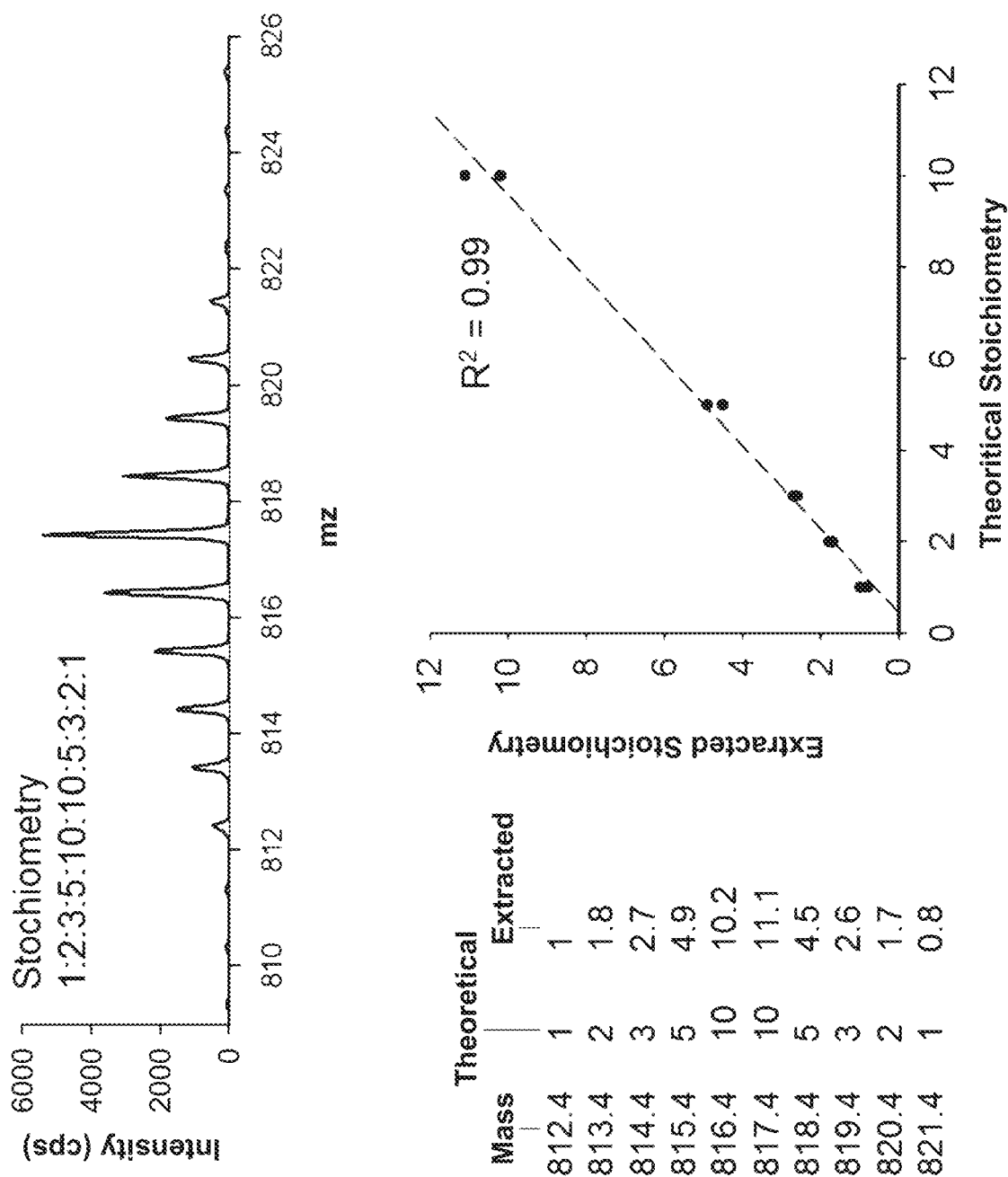
FIG. 4. Multiplex, quantitative detection of iCOREs in library.

In order to investigate whether relative quantities of iCORE abundances in a sample are accurately reflected in MS/MS assays such libraries are subjected to, a sample comprising a 10-plex iCORE library (G1-G10), as described in Example 4, was created, in which the different iCOREs were comprised at different relative abundances in defined ratios. The original sample comprised the following iCORE stoichiometry: G1:G2:G3:G4:G5:G6:G7:G8:G9:G10 were at a ratio of 1:2:3:4:5:10:10:5:3:2:1. The sample was subjected to an MS/MS analysis and the results are shown in FIG. 4. The bar graph shows a good correlation of the original stoichiometry and the measured abundances of the iCOREs. Further analysis of expected (theoretical) and observed (extracted) abundances of each iCORE demonstrate that the MS/MS results closely resemble the actual abundances in the sample. The correlation coefficient of the observed and the expected data set was calculated to be $R^2=0.99$. These results indicate that multiplex iCORE assays are suitable for quantitative analysis and that iCORE abundance is maintained and accurately reflected after multiplex MS/MS assays.

Example 6: Linear Dynamic Range of iCORE MS/MS Assays

Figure 5:
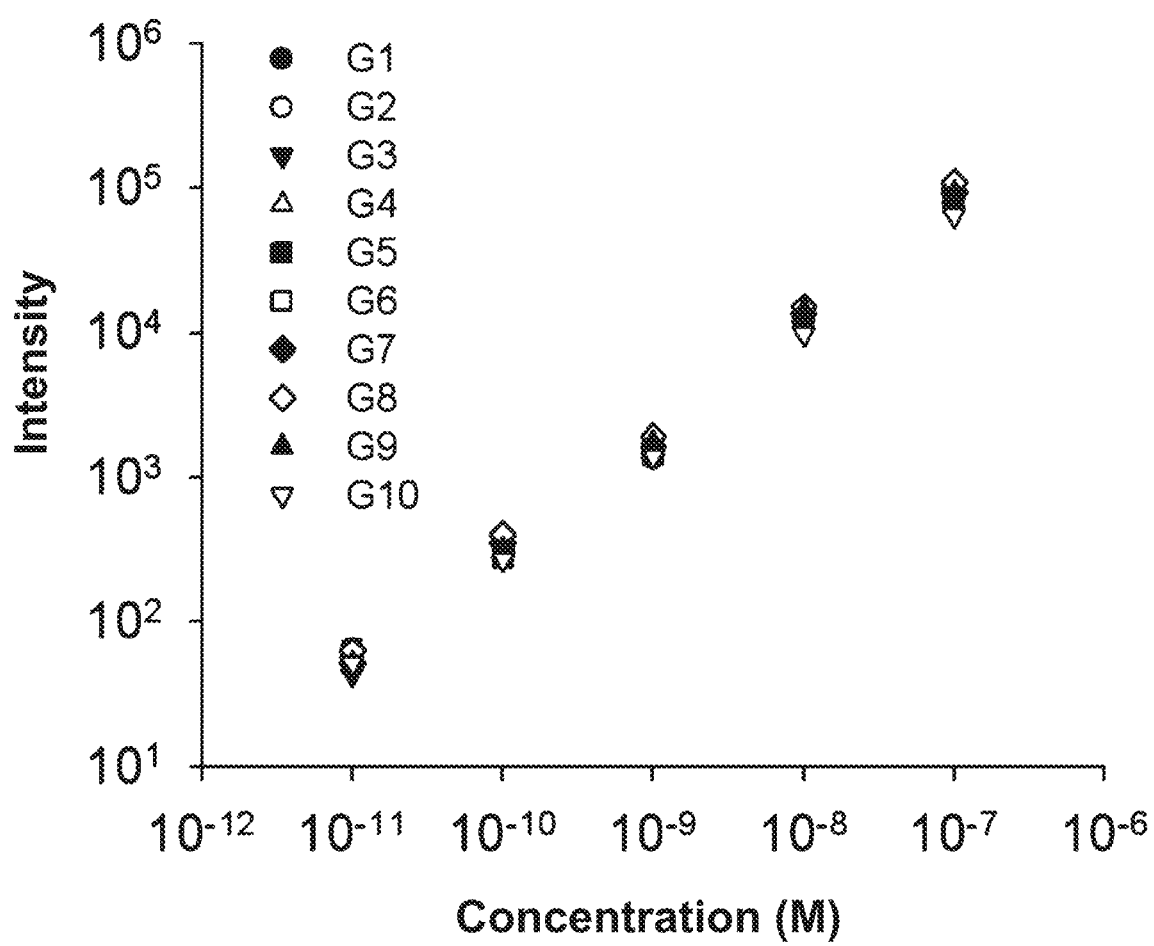
FIG. 5. Evaluation of the dynamic range of multiplexed iCORE assays.

In order to investigate the dynamic range in which iCOREs could be reliably detected and quantified, a dilution series of a 10-plex iCORE library, as described in Example 4, was generated. The library comprise each iCORE (G1-G10) at the same abundance. Five diluted samples, with a concentration of $10^{-7}$M (100 nM), $10^{-8}$M (10 nM), $10^{-9}$M (1 nM), $10^{-10}$M (100 pM), and $10^{-11}$M (10 pM), respectively, were then subjected to an MS/MS assay. The observed intensities for each iCORE at each concentration were plotted in relation to the concentration of the iCOREs in the dilution sample. FIG. 5 shows that all iCOREs were accurately detected at all concentrations, indicating that sensitivity of iCORE MS/MS assays and the linear dynamic range, in which actual iCORE abundances in the sample are accurately reflected in the observed signal intensity, extends to at least from the picomolar range to the nanomolar range, spanning at least five orders of magnitude. These results indicate that accurate detection of iCOREs in a multiplex MS/MS assay is possible at high sensitivity, with even picomolar levels of iCOREs being detectable at an accuracy allowing for quantitative analysis.

Example 7: Efficiency of iCORE Release from Covalently Bound Substrate Via Photocleavage In order to evaluate the efficiency of release of iCOREs covalently bound to a substrate, for example, a binding agent specifically binding a target analyte, a glu-fib-based iCORE was generated and conjugated to a substrate via a covalent bond. The iCORE was connected to the substrate, another peptide via a photocleavable linker, thus generating a photo-caged, or photo-cleavable, iCORE-substrate tandem peptide. The photo-caged tandem peptide was exposed to UV light of ~350 nm wave length for a time (30 min) sufficient for photocleavage of the linker, which resulted in a release of the iCORE from the tandem peptide as shown in the upper panel of FIG. 6. The process of photocleavage was monitored by LC MC (lower panel). The data obtained demonstrate that the photo-caged tandem peptide (I, m/z=881.7) was quantitatively cleaved and close to 100% of the theoretically recoverable amount of the released iCORE (II, m/z=785.4) was rescued. These results indicate that photocleavage of iCOREs covalently bound to other molecules, e.g., other peptides, such as binding agents, or hydrogel-forming molecules, via a photocleavable linker, can be efficiently released by exposure to UV, and can be quantitatively rescued and accurately quantified in LC MS assays.

Example 8: Labeling of Molecules with iCOREs by Conjugation to Reactive Moieties In order to investigate whether iCOREs could be used to covalently label other molecules, glu-fib iCOREs are conjugated to a reactive chemical group able to form a covalent bond to a compatible chemical moiety under certain conditions. For this, a glu-fib iCORE is attached to a reactive chemical moiety able to form a covalent bond to a PEG monomer when exposed to UV light in the presence of PEG monomers. As depicted in FIG. 7, UV exposure results in the formation of a glu-fib iCORE-labeled PEG polymer, in this case a hydrogel, in which the PEG scaffold is covalently bound by iCOREs.

This proof-of principle experiment demonstrates that substrates can be covalently labeled with iCOREs and that iCORE-labeled hydrogels, useful, for example, as scaffolds for tissue engineering, can readily be achieved.

Figure 8A:
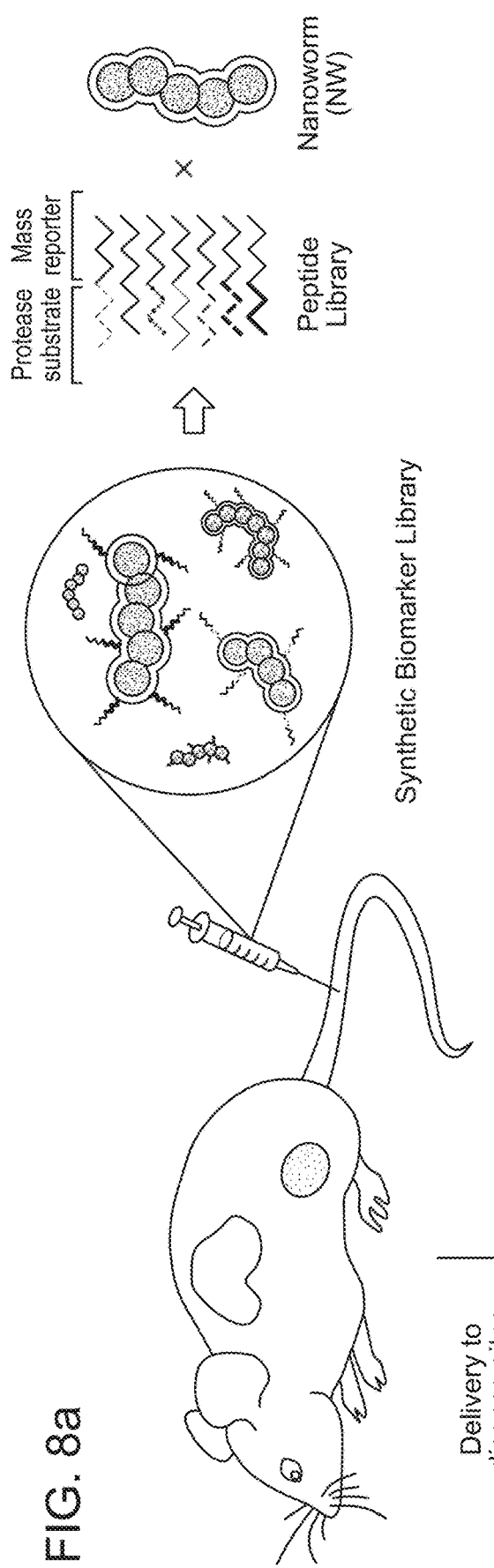
FIGS. 8A-8C. Schematic of iCORE approach for urinary diagnostics.
Figure 8B:
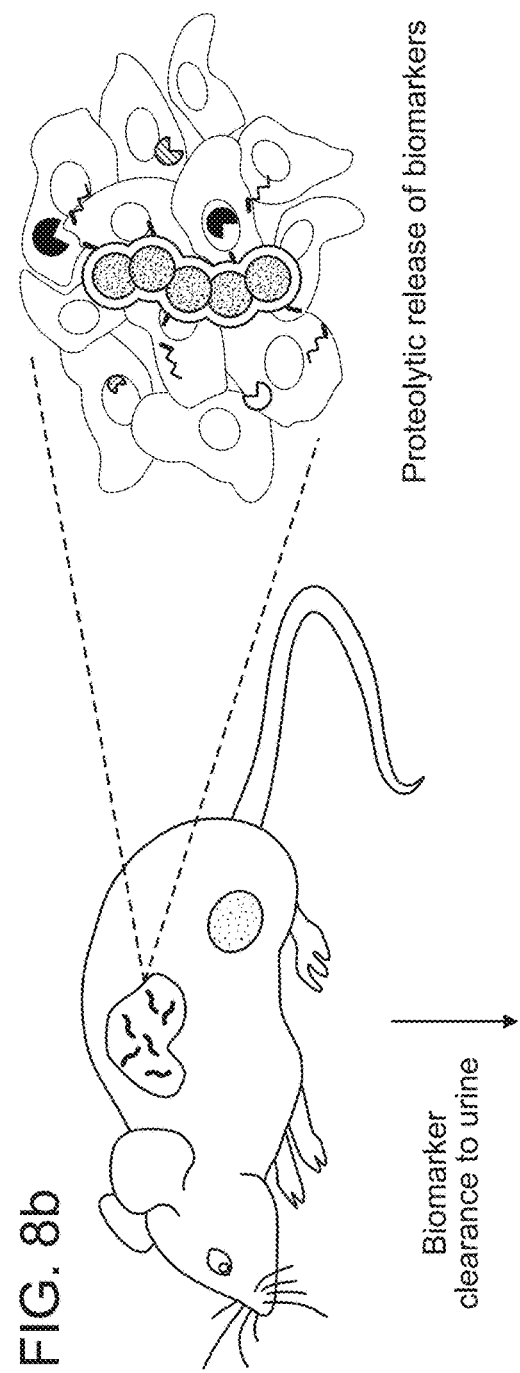
Figure 8C:
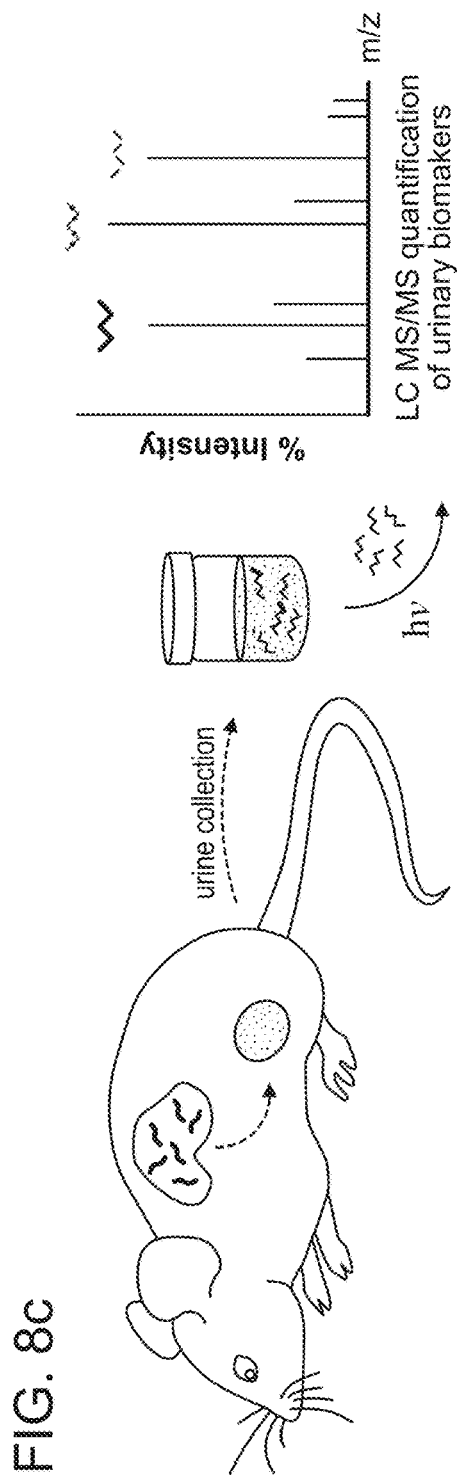

Example 9: Mass-Encoded Synthetic Biomarkers for Multiplexed Urinary Monitoring of Disease A protease sensing platform comprising multiplexed synthetic biomarkers for the detection of disease was developed. FIG. 8 shows a schematic of this approach. FIG. 8a shows a synthetic biomarker library comprised of mass encoded substrate peptide library conjugated onto nanoworm nanoparticles. Administration of NW cocktails in whole animals leads to accumulation in disease tissues (b). Local proteases cleave peptide fragments that subsequently filter into urine. Photo-caged mass reporters are released upon exposure to UV-light and quantified by liquid chromatography tandem mass spectrometry (c).

Figure 9C:
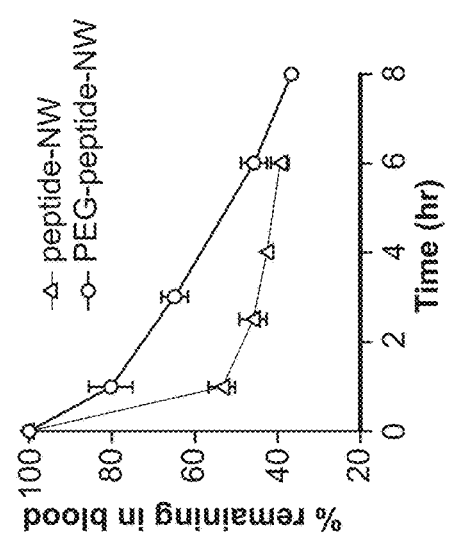
FIGS. 9A-9C. Long-circulating iron oxide nanoworm chaperones.
Figure 9B:
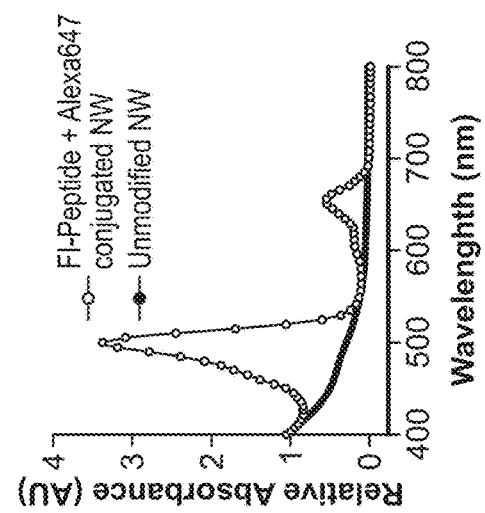
Figure 9A:
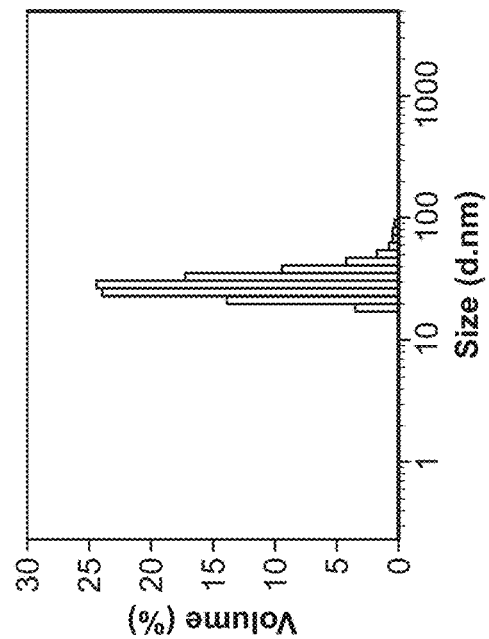

To establish a protease sensing platform, peptide substrates were identified that would be susceptible to cleavage by extracellular proteases associated with liver fibrosis and cancer. Fluorescein-labeled derivatives of ~50 candidate peptide sequences[20-24] were synthesized and conjugated to PEG-coated, long-circulating iron oxide nanoworm[25] (NW) nanoparticles (FIG. 9a,b,c) and incubated with recombinant proteases commonly overexpressed in these diseases (e.g. Matrixmetalloproteases (MMPs), cathepsins) as well as proteases normally present in blood (FXa, Tissue factor (TF), thrombin) to evaluate substrate specificity and accessibility of surface-conjugated peptides to proteases. FIG. 9 shows long-circulating iron oxide nanoworm chaperones. NW size distribution as determined by dynamic light scattering of dextran-coated, iron oxide nanoworms is shown in (a). Absorbance spectra of free NWs (red) and NWs conjugated with Fluorescein-labeled peptides (~500 nm) and Alexa 647 (blue) are shown in (b). In vivo clearance kinetics of PEG-coated (blue) and PEG-free (red) NWs conjugated with substrate peptides are shown in (c). Pegylated NWs extended circulation half-life by ~4 hours.

Figure 10A:
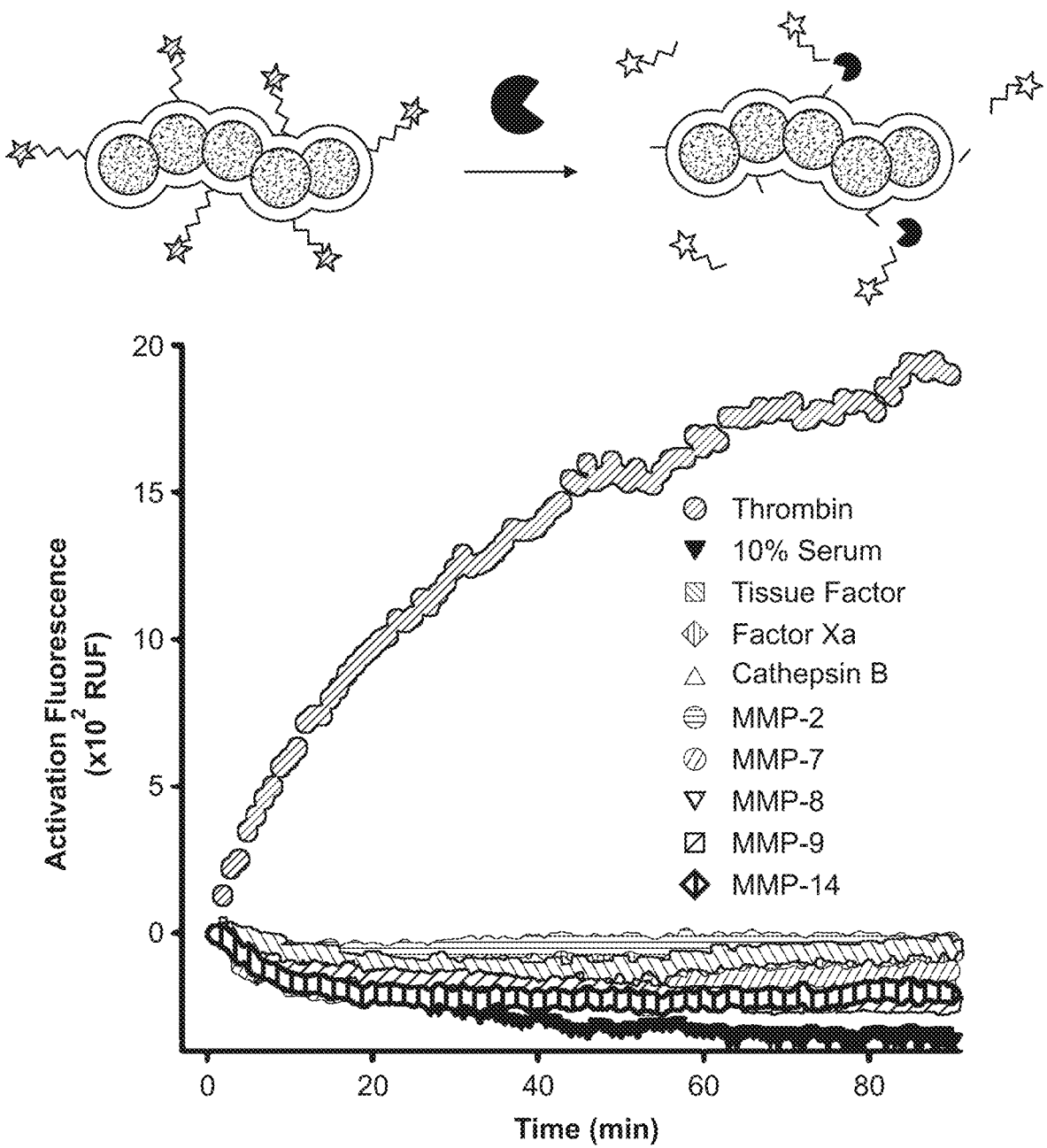
Figure 10B:
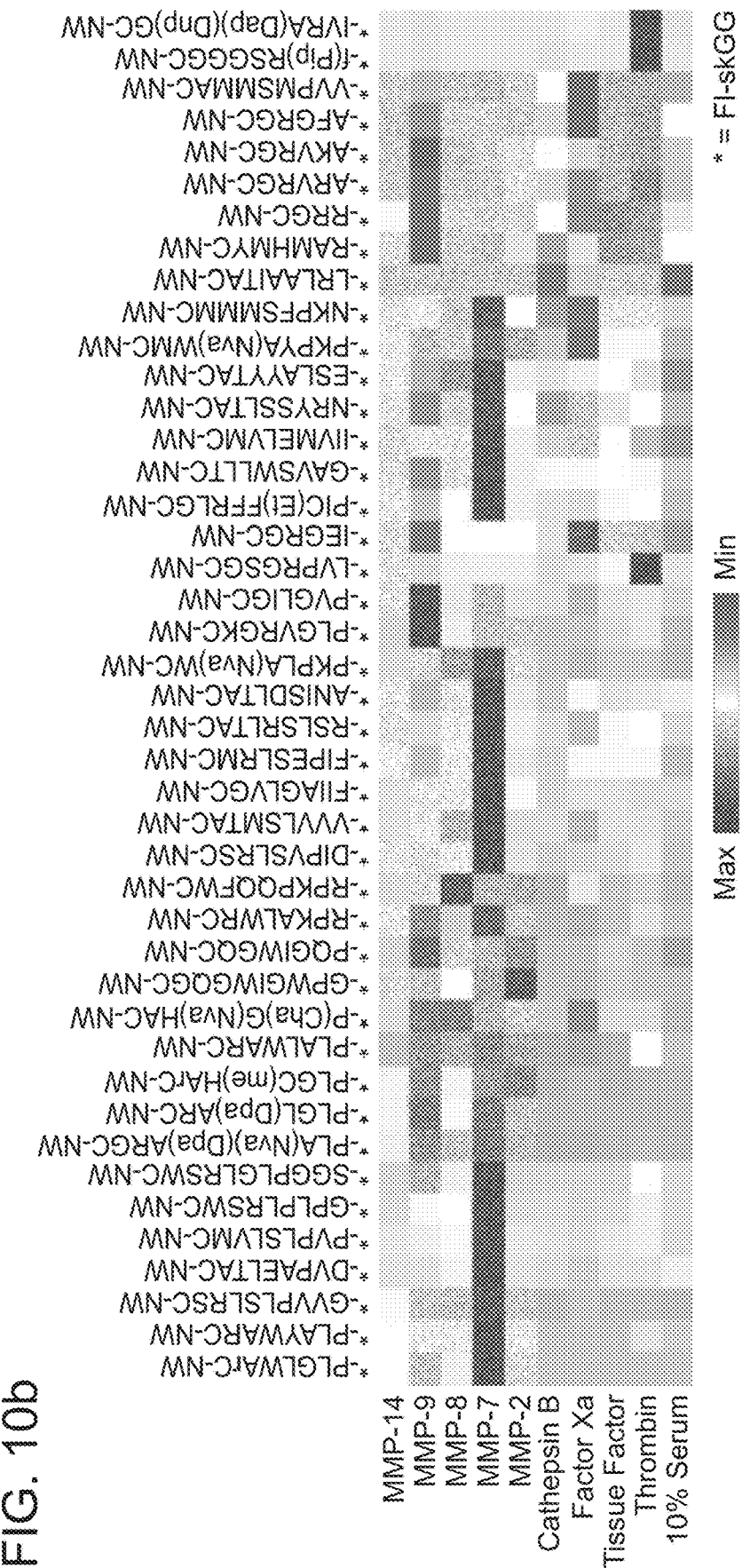

Using this assay, increases in sample fluorescence were observed upon proteolytic cleavage of the tethered fluorescent peptides resulting from abrogation of homoquenching between adjacent fluorophores. Initial reaction velocities were extracted for each protease-substrate combination and compiled for comparative analysis (FIG. 10a,b). FIG. 10 illustrates selecting protease-sensitive substrates for NW-chaperoned urinary trafficking. Kinetics of peptide-NW cleavage monitored by fluorimetry are shown in (a). Specific protease-substrate combinations led to rapid activation. FIG. 10b shows a heat map comparison of initial cleavage velocities for different substrate-protease combinations grouped according to activity and specificity. IVIS in vivo imaging of DDC treated and control animals following intravenous injection of VivoTag-680 labeled Glu-fib peptides, (d) peptide-free NWs, or (e) peptide-conjugated NWs.

From this set, 10 peptides with robust protease susceptibility were selected to serve as a peptide-NW library (Table 1).

TABLE 1 iCORE-encoded peptide biomarker library. Individual probe substrates encoded with photo-caged isobaric mass codes for quantifiation by LC MS/MS.

| | Synthetic Biomarker Library[a, b] | Substrate | Isobaric mass code[c, d] | $y_6$ reporter | $[y_6 + H^+]$ |
|---|---|---|---|---|---|
| G1 | e$^{+3}$G$^{+6}$VndneeGFfsAr-X-K(FAM)GGPQGIWGQC-NW | PQGIWGQ | e$^{+3}$G$^{+6}$VndneeGFfsAr | GFfsAr | 683.4 |
| G2 | e$^{+2}$G$^{+6}$Vndnee$^{+1}$GFfsAr-X-K(FAM)GGLVPRGSGC-NW | LVPRGSG | e$^{+2}$G$^{+5}$Vndnee$^{+1}$GFfsAr | $^{+1}$GFfsAr | 684.4 |
| G3 | e$^{+1}$G$^{+6}$Vndnee$^{+2}$GFfsAr-X-K(FAM)GGPVGLIGC-NW | PVGLIG | e$^{+1}$G$^{+6}$Vndnee$^{+2}$GFfsAr | $^{+2}$GFfsAr | 685.4 |
| G4 | eG$^{+6}$Vndnee$^{+2}$GFfs$^{+1}$Ar-X-K(FAM)GGPWGIWGQGC-NW | PWGIWGQG | eG$^{+6}$Vndnee$^{+2}$GFfs$^{+1}$Ar | $^{+2}$GFfs$^{+1}$Ar | 686.4 |
| G5 | eG$^{+5}$VndneeGFfs$^{+4}$Ar-X-K(FAM)GGPVPLSLVMC-NW | PVPLSLVM | eG$^{+5}$VndneeGFfs$^{+4}$Ar | GFfs$^{+4}$Ar | 687.4 |
| G6 | e$^{+3}$G$^{+1}$Vndnee$^{+1}$GFfs$^{+4}$Ar-X-K(FAM)GGPLGLRSWC-NW | PLGLRSW | e$^{+3}$G$^{+1}$Vndnee$^{+1}$GFfs$^{+4}$Ar$^{+1}$GFfs$^{+4}$Ar | | 688.4 |
| G7 | e$^{+3}$GVndneeG$^{+6}$FfsAr-X-K(FAM)GGPLGVRGKC-NW | PLGVRGK | e$^{+3}$GVndneeG$^{+6}$FfsAr | G$^{+5}$FfsAr | 689.4 |
| G8 | e$^{+2}$GVndneeG$^{+6}$Ffs$^{+1}$Ar-X-K(FAM)GGf(Pip)RSGGGC-NW | f(Pip)RSGGG | e$^{+2}$GVndneeG$^{+6}$Ffs$^{+1}$Ar | G$^{+6}$Ffs$^{+1}$Ar | 690.4 |
| G9 | e$^{+1}$GVndnee$^{+2}$G$^{+6}$FfsAr-X-K(FAM)GGfPRSGGGC-NW | fPRSGGG | e$^{+1}$GVndnee$^{+2}$G$^{+6}$FfsAr | $^{+2}$G$^{+6}$FfsAr | 691.4 |
| G10 | eGVndnee$^{+3}$G$^{+6}$FfsAr-X-K(FAM)GGf(Pip)KSGGGC-NW | f(Pip)KSGGG | eGVndnee$^{+3}$G$^{+6}$FfsAr | $^{+3}$G$^{+6}$FfsAr | 692.4 |

[a]X(3-amino-3-(2-nitrophenyl)propionic acid), FAM (carboxyfluorescein), Pip (pipecolic acid), NW (nanoworm)
[b]lower case = d-amino acid
[c]photocleaved C-terminus = CONH$_2$
[d]mass = 1589.8 Da Sequences of G1-G10 correspond, from top to bottom, to SEQ ID NO: 8-SEQ ID NO: 17, respectively. Substrate sequences correspond, from top to bottom, to SEQ ID NO: 18-SEQ ID NO: 27, respectively. The isobaric mass codes correspond to SEQ ID NO: 28, and the y6 reporters correspond to SEQ ID NO: 29.

Figure 11A:
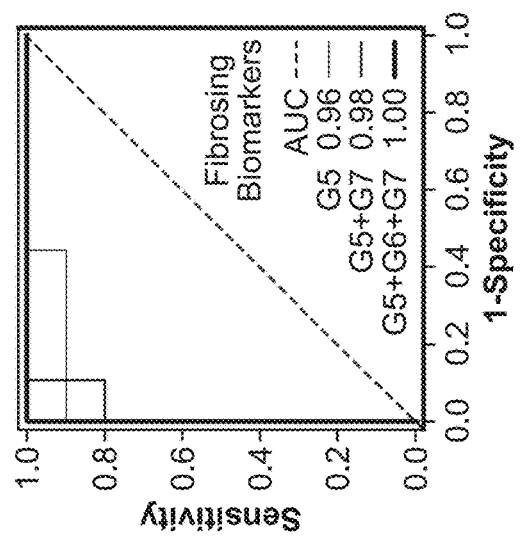
FIGS. 11A-11H. Urinary biomarkers of hepatic fibrosis and resolution in DDC-treated mice.
Figure 12A:
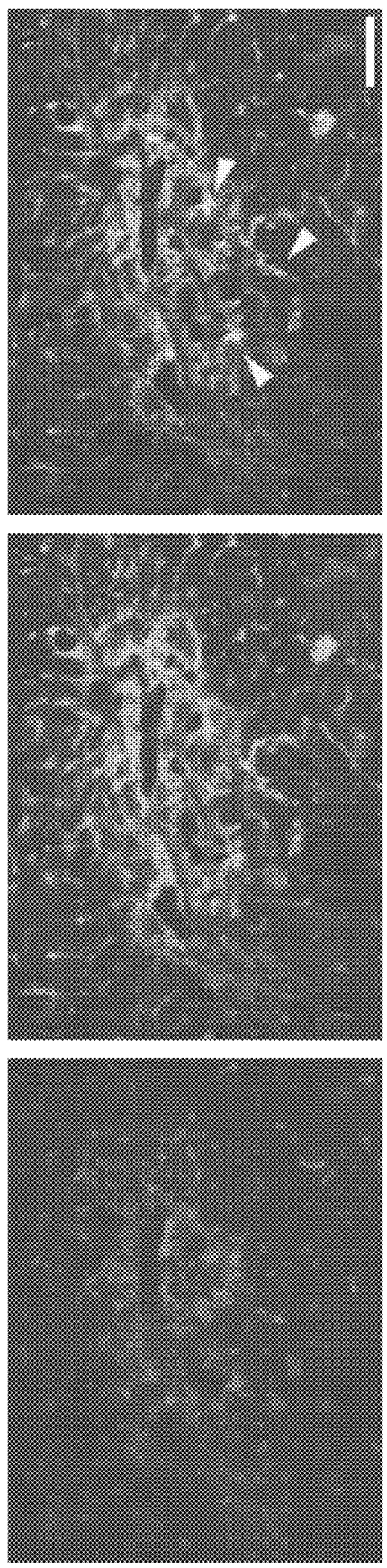
FIGS. 12A-12D. Immunofluorescence of liver sections.
Figure 12B:
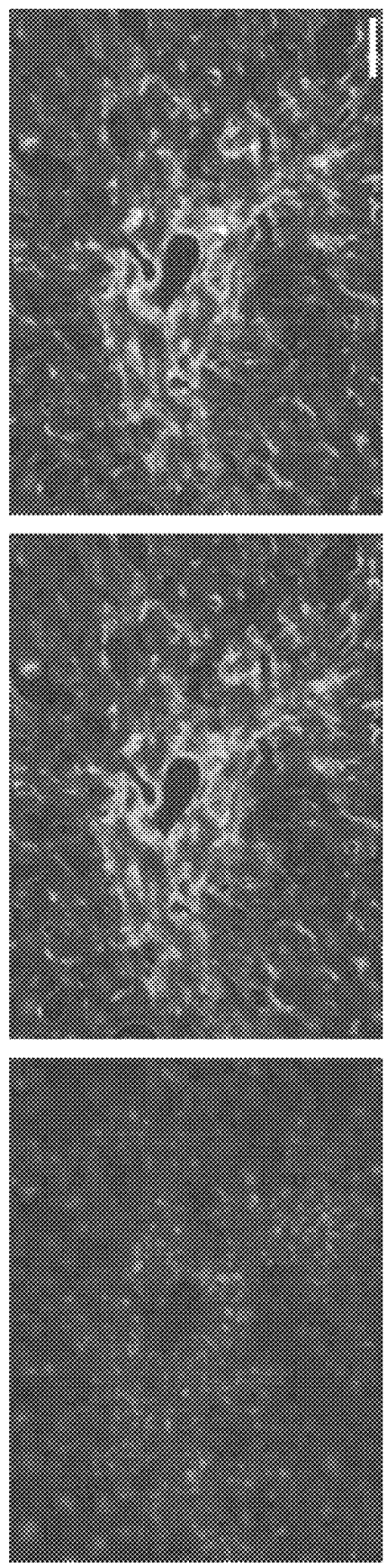
Figure 12C:
Figure 12D:
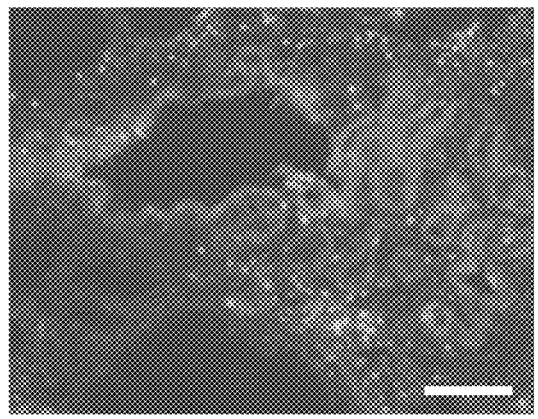

In order to design a system that would probe diseased microenvironments, the biodistribution of each system component (i.e. peptide and nanoparticle) was investigated in disease models in vivo. Here, a mouse model of liver fibrosis was selected in which FVB/NJ mice fed with 3,5-diethoxy-carbonyl-1,4-dihydrocollidine (DDC) develop progressive liver disease as a result of chronic bile duct injury[26] (FIG. 11a,b,c), leading to fibrotic and proteolytically active livers (FIG. 12b,c,d).

FIG. 11 illustrates urinary biomarkers of hepatic fibrosis and resolution in DDC-treated mice. FIG. 11a shows the induction of liver fibrosis and NW administration timeline. FIG. 11b shows quantification of total liver collagen by hydroxyproline analysis. DDC treatment led to ~3 fold increase in liver collagen by week 3 (***P<0.001) and a ~30% drop between week 7 and 11 (*P<0.05) that remained above pre-treatment values (*P<0.05) (One-way ANOVA, Tukey post test, n=3, s.e.m.). Sirius red histochemistry of liver sections (scale bar=50 μm) indicated the presence of fibrotic extensions emanating from portal triads at week 3, persisting to week 7, and resolving by 11 weeks (c). IVIS in vivo imaging showed urinary accumulation of ensemble reporter library in DDC-treated animals (d). Kinetics of urinary accumulation quantified by a-FITC immunoprecipitation (3 wk timepoint, *P<0.05, Two-way ANOVA, Tukey post test; error bars=s.e.m.) are shown in (e). FIG. 11f shows box and whisker plots of individual iCORE peak intensities plotted as DDC over control at 0, 3, 7, and 11 weeks (*P<0.05, **P<0.01; repeated measures ANOVA, Tukey post test; n=10). FIG. 11g shows ROC curves of single, double and triple combinations of fibrosing biomarkers with associated area under curves (AUC). (h) ROC curves of single, double and triple combinations of resolving biomarkers with associated area under curves (AUC).

FIG. 12 illustrates immunofluorescence of liver sections. FIG. 12a shows periportal images of macrophage (red) and NW (green) infiltrate into fibrosing zones. Arrows highlight areas of colocalization. FIG. 12b shows periportal images of MMP9 (red) and NW (green). MMP9 expression was not found in healthy livers (c). FIG. 12d shows Fluorescence image of periportal zone after gelatin in situ zymography. Scale bars=100 μm.

To evaluate peptide trafficking, the peptide glutamatefibrinopeptide B (Glu-fib, EGVNDNEEGFFSAR, SEQ ID NO: 1) was selected as a prototypic urinary marker because its endogenous derivative (fibrinopeptide B) is biologically inert and normally filters freely into urine when released during coagulation.[27] Fluorophore-labeled Glu-fib administered intravenously (i.v.) efficiently filtered into urine in both fibrosing and healthy animals with undetectable liver homing (FIG. 10c). In contrast, larger peptide-free NWs (~40 nm hydrodynamic radius, FIG. 9a) homed to the liver (FIG. 10d), consistent with the size-dependent trafficking of nanomaterials and a renal clearance threshold of ~5 nm for inorganic nanoparticles.[28] Importantly, in animals treated with fluorophore-labeled peptides conjugated to NWs, significant NW-mediated peptide homing was observed to both fibrosing and healthy livers leading to a strong increase in urinary fluorescence in diseased animals resulting from renal filtration of cleaved peptide fragments (FIG. 10e).

Profiling Protease Activities by Mass Spectrometry

Figure 13A:
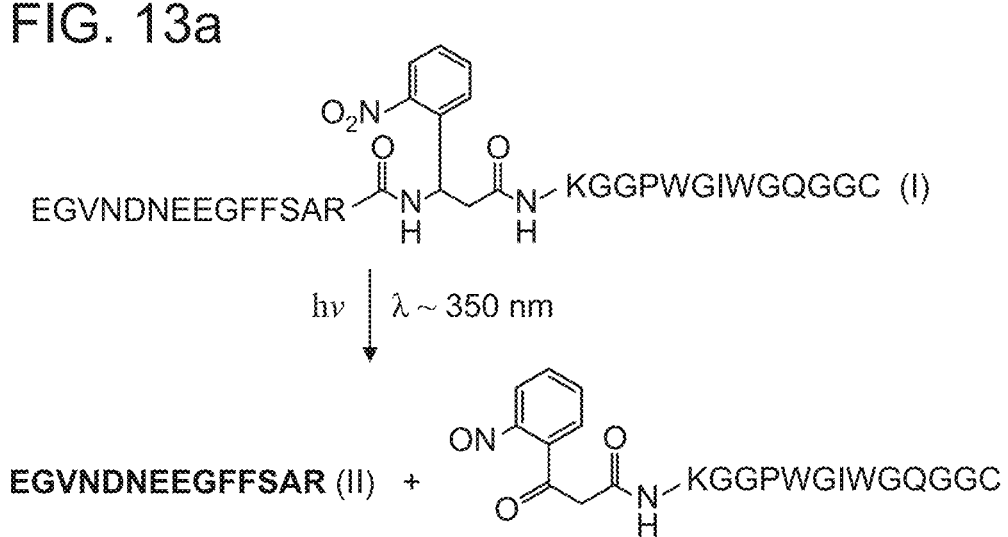

Despite the multiplexing advantages of mass-encoding, one challenge of detecting protease activity by MS is that peptide substrates in complex proteolytic environments can be cleaved at multiple sites by promiscuous proteases and truncated by exoproteases[4,29] to produce diverse pools of poorly defined fragments that confound mass analysis. Here, well-defined mass reporters to encode a substrate library were designed. In light of the favorable renal clearance properties of Glu-fib, d-isomer rich derivatives of Glu-fib were appended to the N-termini of each protease substrate to serve as protease resistant mass reporters and to promote renal filtration upon substrate cleavage and release from NWs (Table 1). These tandem peptides were further modified with internal photo-labile residues[30] to enable the recovery of well-defined Glufib peptides by photolysis from complex urinary cleavage fragments following in vivo proteolysis. To test this construct, a model photo-caged tandem peptide was synthesized (compound I, FIG. 13a). Consistent with previously published reports on nitrophenyl groups, exposure of compound I (triply charged, 881.7 m/z; FIG. 13b, top panel) to UV light triggered peptide cleavage, resulting in the appearance of doubly charged, acetamide-terminated Glu-fib (785.4 m/z; FIG. 13b, bottom panel).

Figure 13D:
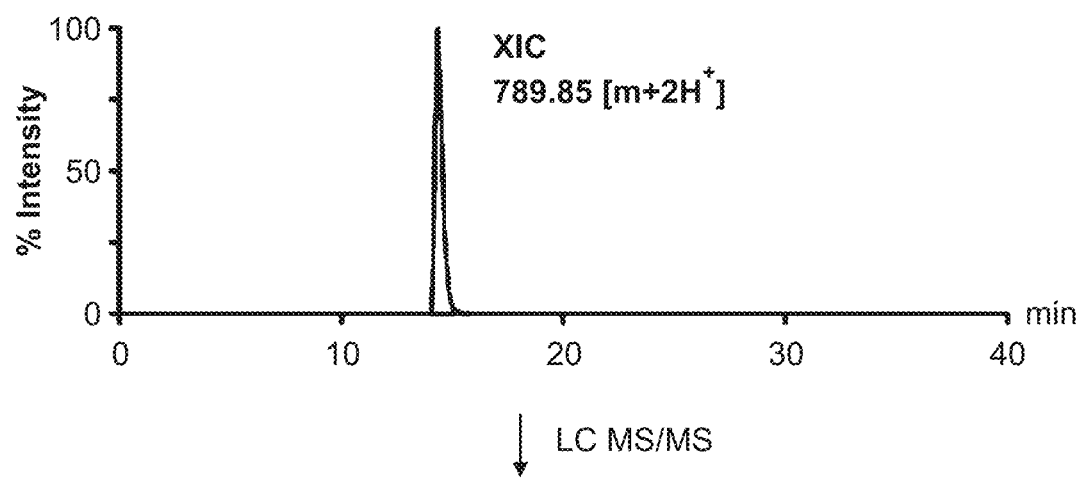
Figure 13E:
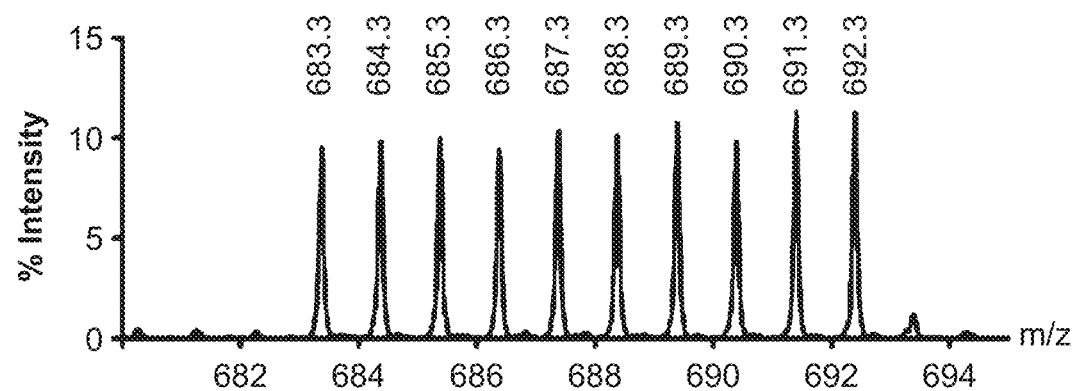

FIG. 13 shows photo-caged iCORE libraries for multiplexed profiling of protease activities by LC MS/MS. FIG. 13a illustrates the structure of tandem peptide (compound I) containing an internal UV-sensitive linker. Shown here is the structure of free Glu-fib (compound II) generated after photolysis (~350 nm). FIG. 13b shows LC MS spectra of compound I before (top, triply-charged m/z: 881.7) and after (bottom, doubly-charged m/z: 785.4) exposure to UV light. FIG. 13c shows a 10-plex isobaric peptide library derived from Glu-fib. FIG. 13d shows an extracted ion chromatogram of an equimolar 10-plex iCORE mixture (789.80-789.90 m/z). The entire multiplexed set was chromatographically indistinguishable. FIG. 13e shows an iCORE MS/MS spectrum following collision induced disassociation. Individual reporters were identified via unique y6 reporter ions (683.3-692.3 m/z) each differentiable by a single mass unit. FIG. 13f shows an iCORE MS/MS spectrum following incubation of a 10-plex, iCORE-encoded peptide-NW cocktail with recombinant MMP9.

Figure 14A:
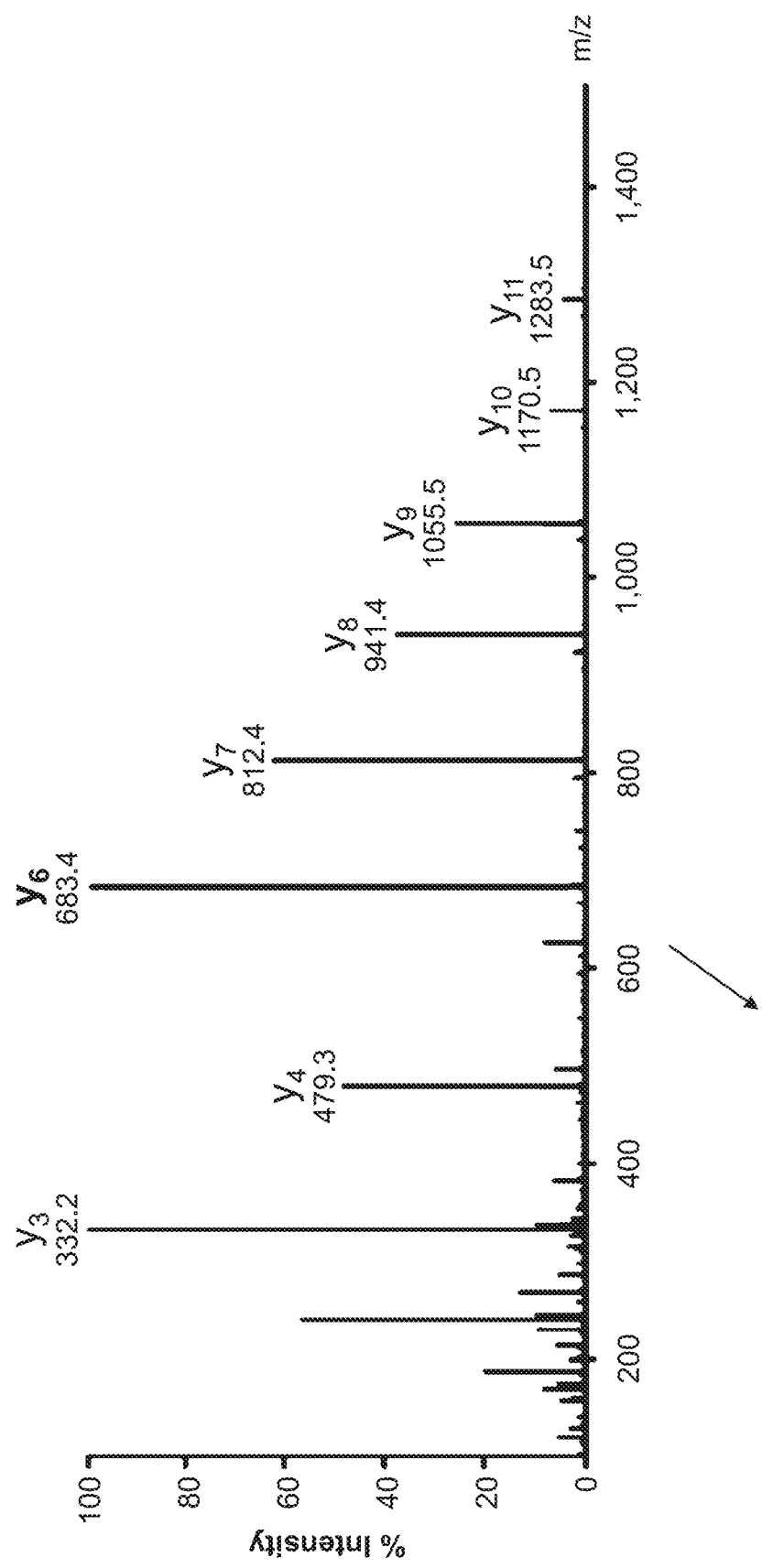

FIG. 14 illustrates Isobaric COded REporter (iCORE) mass encoding. FIG. 14a shows an MS/MS spectrum following collision induced disassociation of Glu-fib. Peaks correspond to c-terminal, y-type peptide fragments. FIG. 14b lists 10 isotopic analogs and corresponding masses produced via isobaric encoding. Each sequence was constructed by selectively enriching the balance or reporter regions with 'heavy' amino acids to produce unique y6 reporter ions while maintaining a uniform total mass.

Figure 15:
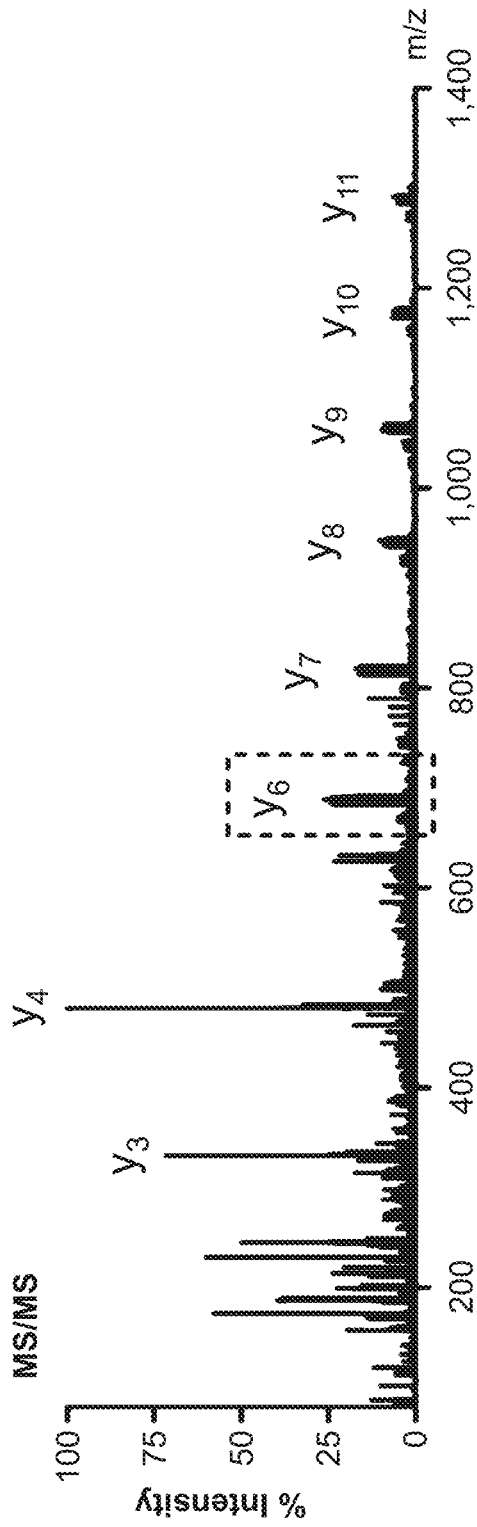
FIG. 15. MS/MS spectrum of 10-plex iCORE library. iCORE peak clusters centered on y-type ions. The y6 region outlined by a box is presented as FIG. 13e.
Figure 16B:
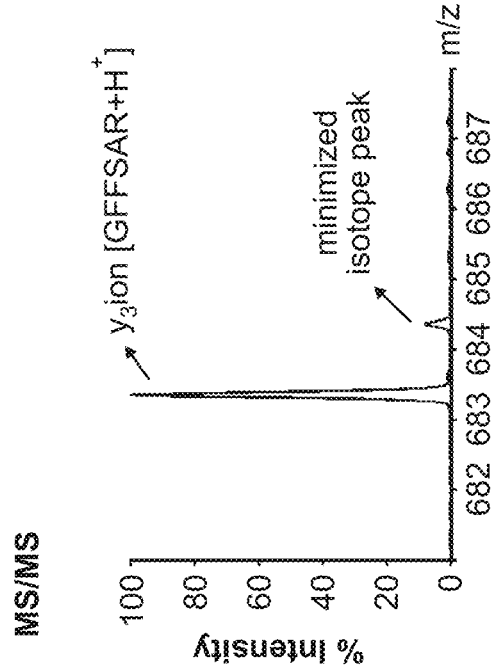
FIGS. 16A-16B. Unit collection window for peptide fragmentation minimizes peak overlap arising from naturally occurring isotopes. (a) A typical MS spectrum of an isotope-coded Glu-fib peptide. The parent precursor peptide was collected for fragmentation via a unit mass window (gray), excluding the naturally occurring isotope peaks. (b) Resulting MS/MS spectrum. Isotope peak was minimized, comprising ~5% of the original peak intensity. EGVNDNEEGFFSAR corresponds to SEQ ID NO: 1. GFFSAR corresponds to SEQ ID NO: 4.
Figure 16A:
Figure 17A:
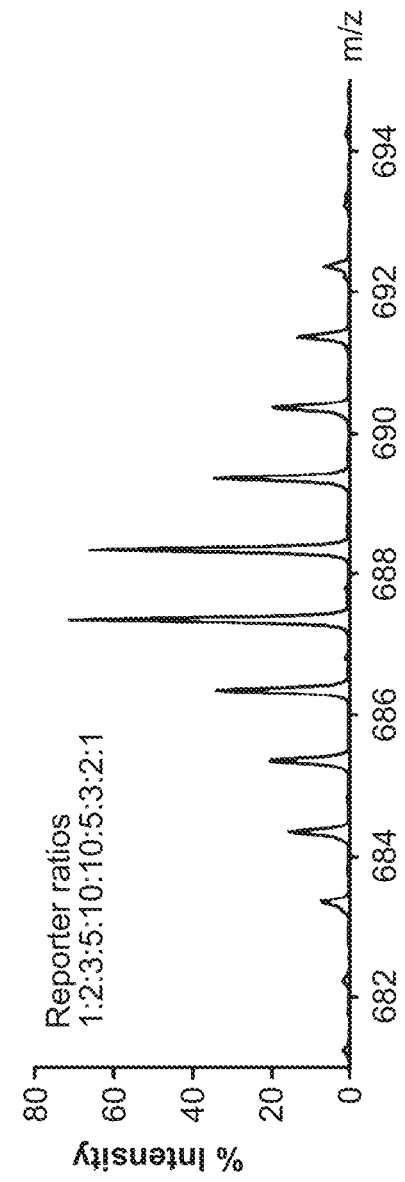
FIGS. 17A-17C. iCORE LC MS/MS analysis is quantitative.
Figure 17C:
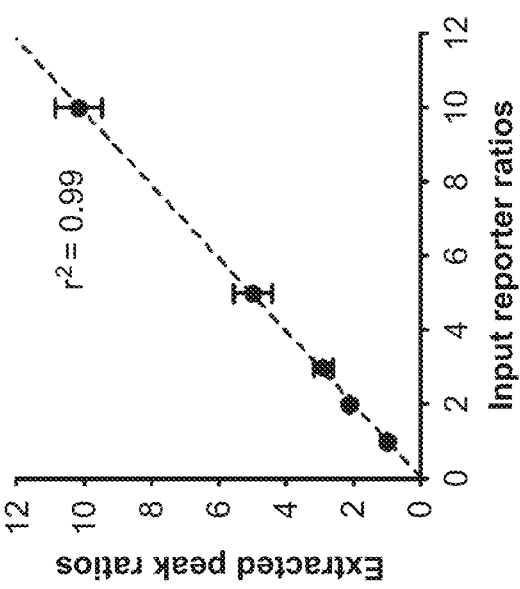
Figure 17B:
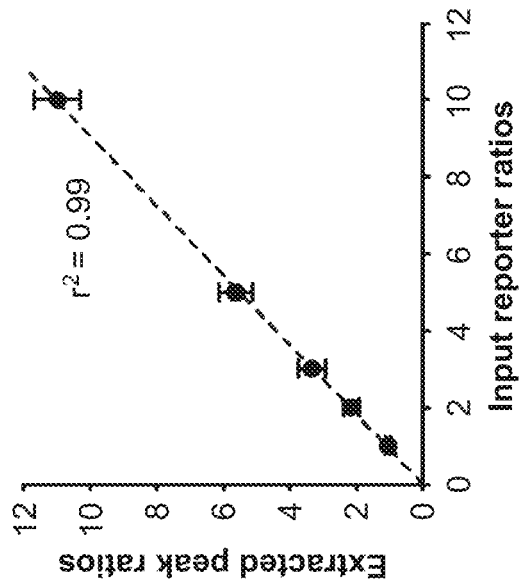

In order to design an extensible encoding strategy for the library of protease substrates, the ability of isobaric mass encoding[31,32] was investigated to be extended to peptide scaffolds such as the urinary reporter Glu-fib to produce a family of mass reporters. The distinguishing feature of an isobaric encoding strategy is that individual members of a family of reporters share a parent mass to facilitate efficient peptide collection by MS, but can be subsequently identified via unique MS/MS ions upon fragmentation. It was first determined that Glu-fib fragments into C-terminal y-type ions (FIGS. 10a) and 10 mass codes were constructed centered on the y6 ion (GFFSAR, SEQ ID NO: 4) by enriching the hexamer with heavy amino acids to produce variants differentiated by 1 Da each (FIG. 10b). This introduced mass shift was then balanced by isotope enrichment within the remainder of the peptide (EGVNDNEE, SEQ ID NO: 5). As a result, each peptide was characterized by an identical nominal mass and a distinct y6 fragment ion. This encoding method was termed "isobar COded REporters" (iCORE). To validate this approach, an equimolar 10-plex iCORE mixture (FIG. 13c) was analyzed by LC MS/MS and the entire peptide library was found to initially appear as a single, unresolved peak (extracted ion chromatogram, 789.95±0.5 m/z, FIG. 13d) but following fragmentation, to resolve into a 10 peak spectrum with no fragmentation bias (683.4-692.4 m/z, FIG. 15, FIG. 13e). To remove confounding peak overlap arising from naturally occurring isotopes (e.g. 13C), iCORE peptides were selectively fragmented via a unit mass window centered on the precursor ion (FIG. 16a) to minimize the signal from naturally occurring isotopes to ~5% of the parent peak (FIG. 16b). Thus, in samples spiked with reporters at defined ratios (1:2:3:5:10:10:5:3:2:1), a linear correlation was observed between peak intensity and stoichiometry in both unmodified and peak-subtracted analysis (n=3, R2=0.99 and R2=0.99 respectively, FIG. 17a,b,c). FIG. 17 demonstrates that iCORE LC MS/MS analysis is quantitative. FIG. 17a shows an MS/MS spectrum of a 10-plex mixture of iCORE reporters combined in a 1:2:3:5:10:10:5:3:2:1 ratio. Extracted peak intensities were highly correlated with the input reporter stoichiometry (r2=0.99; n=3; error bars=s.e.m.) (b). To account for naturally occurring isotopes (FIG. 16), individual reporter intensities were modified by subtracting 5% of the prior reporter intensity (c). Compensated reporter ratios also strongly correlated with reporter ratios (r2=0.99; n=3; error bars=s.e.m.). All subsequent samples were peak-adjusted to reflect contributions from naturally occurring isotopes.

Figure 18B:
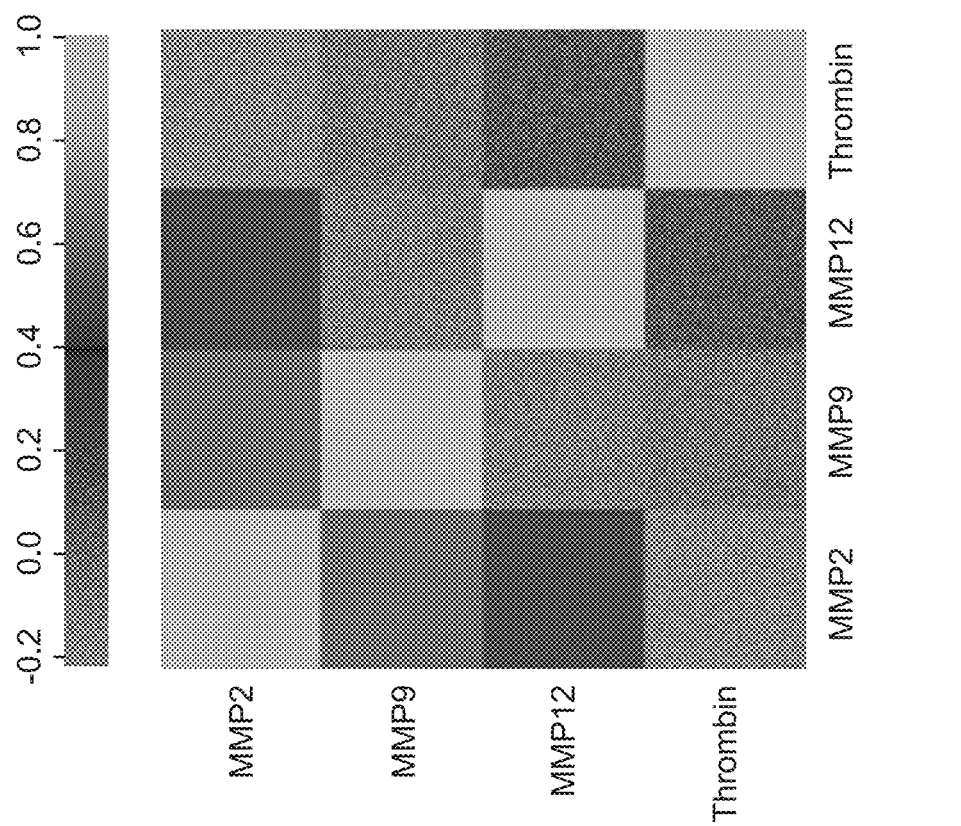
FIGS. 18A-18B. Protease-specific iCORE mass signatures. (a) iCORE MS/MS profiles of recombinant proteases MMP2, MMP12, and thrombin. (b) Graphical representation of Pearson's correlation coefficients between proteases.
Figure 18A:
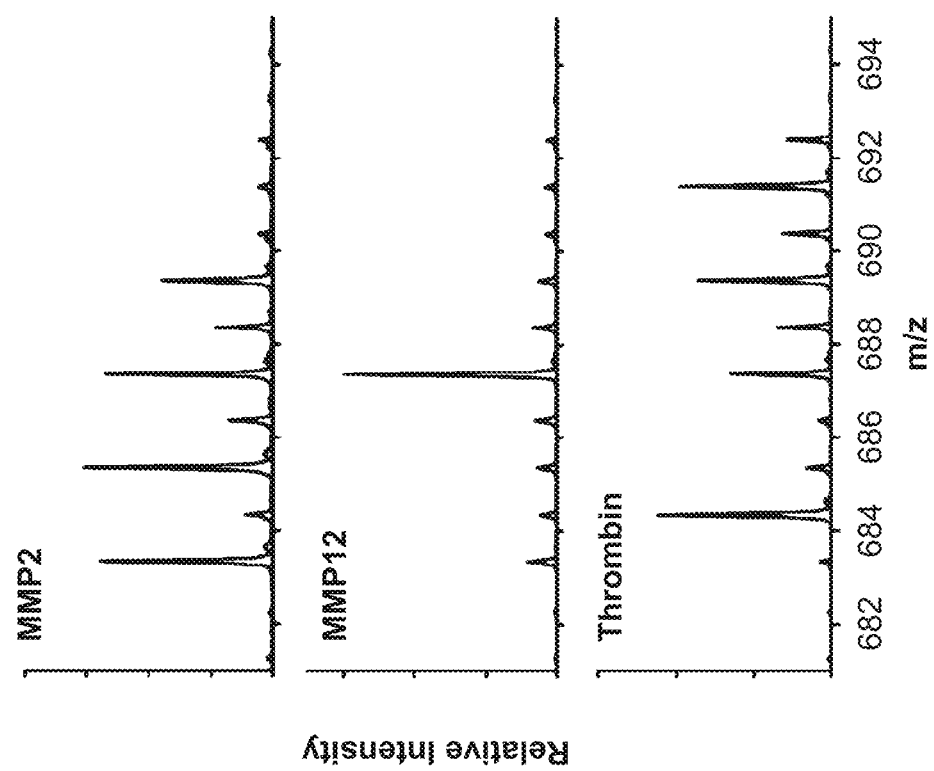

To evaluate the ability of iCORE multiplexing to simultaneously report on the activities of many protease-substrate combinations, a 10-plex, equimolar cocktail of iCORE encoded peptide-NWs was treated with recombinant MMP9 (Table 1). Following incubation, cleavage products were isolated by size filtration and exposed to UV-light prior to MS/MS analysis. Notably, collective substrate activities were translated into distinct iCORE landscapes characterized by markedly different y6 reporter intensities (FIG. 13F). This library was applied to several other recombinant proteases (FIG. 18a) and no strong correlation was found between different iCORE protease profiles (i.e. MMP2, MMP9, MMP12, and thrombin) as determined from Pearson's correlation analysis (FIG. 18b), illustrating the ability of iCORE-encoded NWs to monitor many protease and protease-substrate combinations uniquely.

Example 10: Monitoring Hepatic Fibrogenesis and Resolution

Liver fibrosis is a wound healing response to chronic liver injury and results in the buildup of scar tissue that can lead to cirrhosis, liver failure and cancer.[18] The dynamics of extracellular matrix accumulation such as collagen is largely driven by fibrogenic hepatic stellate cells and myfibroblasts, and matrix remodeling proteases such as MMPs and their inhibitors. The current gold standard for monitoring is a needle biopsy followed by histological analysis; however, this technique is invasive, confounded by high sampling heterogeneity, carries a finite risk of complications and cannot be performed frequently as needed (e.g. monitoring antifibrotic therapies).[33] Noninvasive assays including ultrasound imaging, elastography, and serum biomarkers are limited by their low accuracies and limited prognostic utility.[34] Thus, there remains an urgent need for noninvasive biomarkers to replace biopsy-based monitoring, identify and validate new antifibrotic agents, and to support clinical decision making.[35] Here, it was sought to identify synthetic biomarkers with the capacity to monitor liver fibrosis, and to extend the DDC-induced model to include both fibrosing and resolving disease (FIG. 11a,b,c).

Figure 11B:
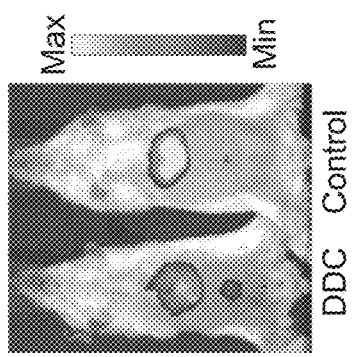
Figure 11C:
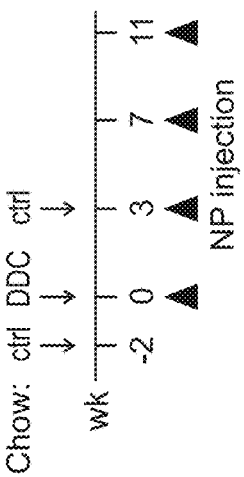
Figure 11D:
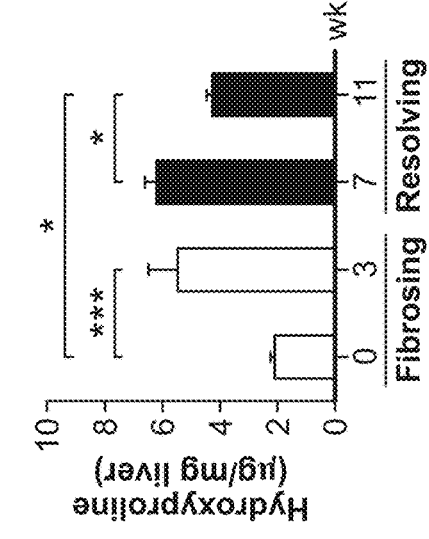
Figure 11E:
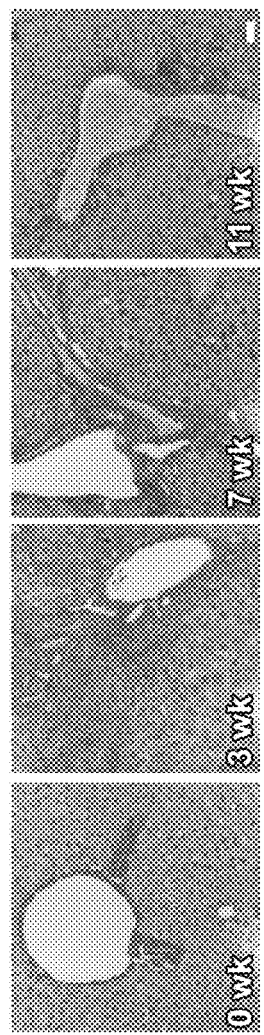

The in vivo trafficking and ability of iCORE-encoded synthetic biomarkers to produce an ensemble urinary signal during fibrotic progression was determined. Intravenous administration of a fluorophore-labeled, 10-plex peptide-NW cocktail resulted in a 2-fold increase in urinary fluorescence in animals treated with DDC for 3 weeks (*P<0.05, Twoway ANOVA; FIG. 11d,e). Immunofluorescence imaging of liver sections revealed that most NWs escaped sequestration by resident macrophages (FIG. 12a, arrow), infiltrating freely into the parenchyma and into actively fibrosing periportal zones characterized by punctate MMP9 expression (FIG. 12b,c). Similar patterns appeared in sections treated with DQ-gelatin substrates (FIG. 12d) which permit in situ visualization of active collagen-degrading proteases.

Collectively, these results indicated that NWs home to fibrosing liver microenvironments containing active proteases. In order to determine the behavior of individual reporters to identify sensitive and specific synthetic biomarkers, the processes of fibrosis and resolution were probed by iCORE mass analysis. Mice treated transiently with DDC for 3 weeks followed by restoration of DDC-free chow develop distinct fibrosing and resolving windows (0-3 and 7-11 weeks respectively, FIG. 11a) as verified macroscopically by Sirius red collagen staining of liver sections (FIG. 11c), and by hydroxyproline analysis which quantifies total tissue collagen (FIG. 11b). With this treatment regime, liver collagen increased ~3-fold compared to pretreatment levels after 3 weeks on DDC, persisted from week 3-7 after initial removal of DDC, and significantly decreased from week 7-11 after sustained DDC withdrawal (*P<0.05, ***P<0.005, n=3).

Figure 11G:
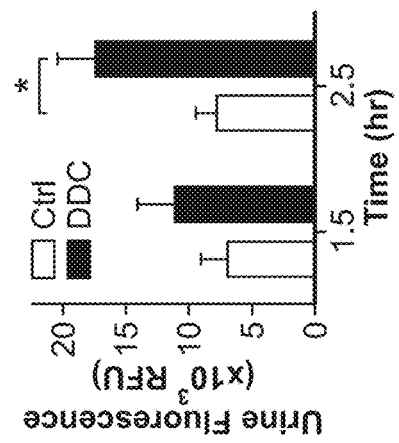
Figure 11H:
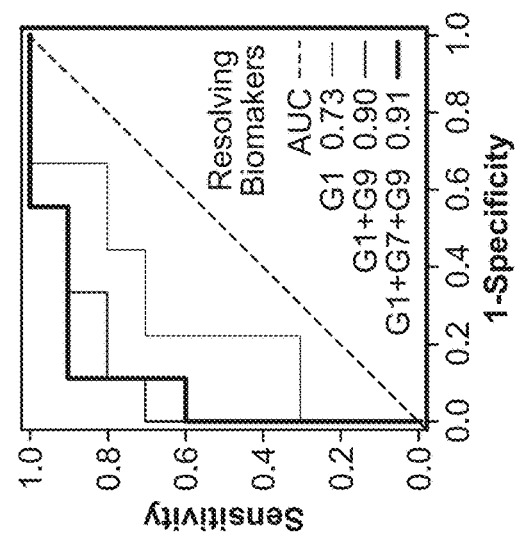
Figure 11F:
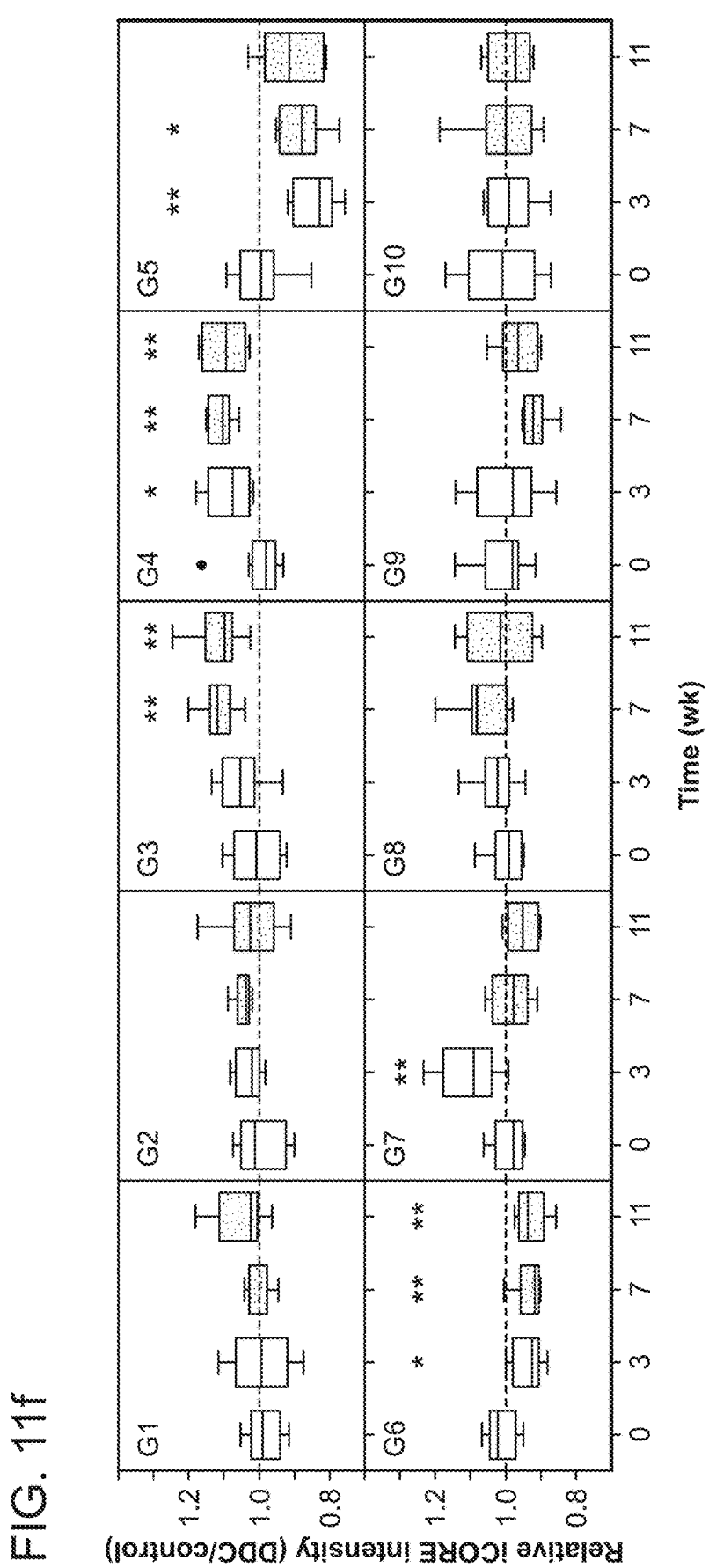
Figure 19:
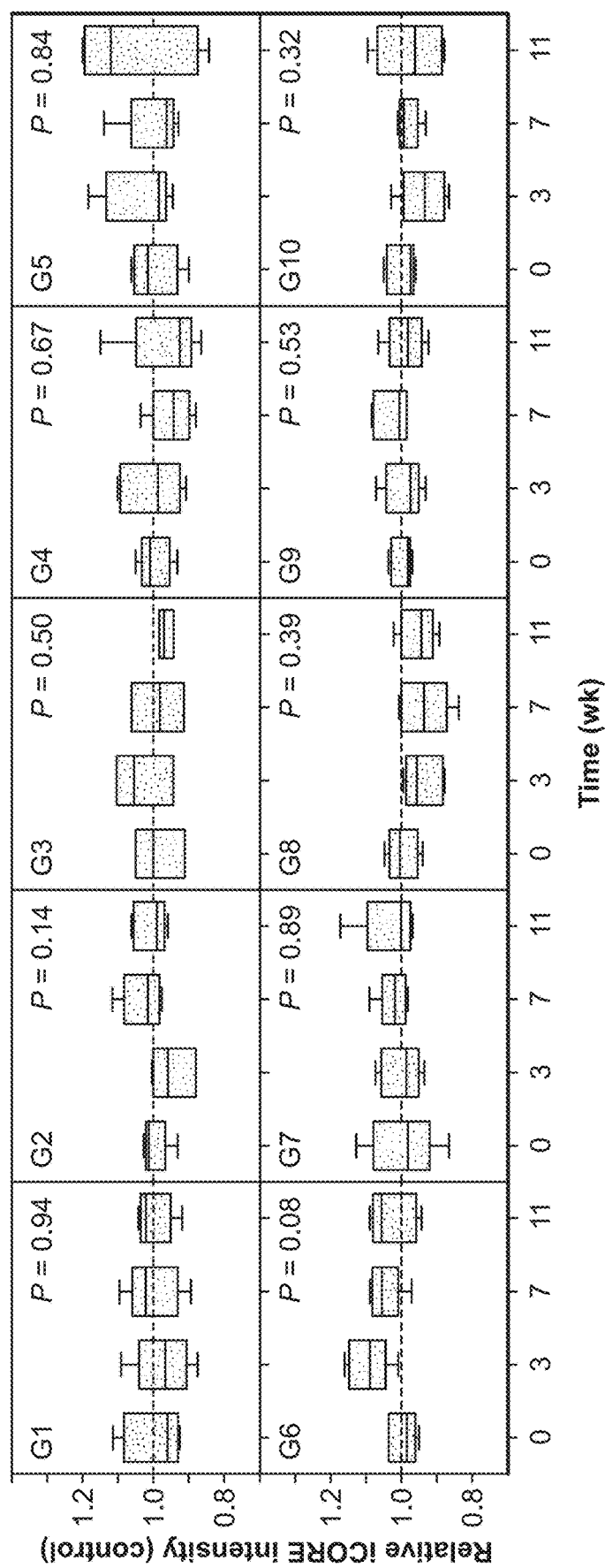
FIG. 19. iCORE profiles of control animals. Box-and-whisker plots of individual iCORE peak intensities (repeated measures ANOVA, n=5)

Thus, to monitor the transitions between fibrosing and resolving disease, NWs were administered at 0, 3, 7, and 11 weeks into DDC-treated and age-matched control animals followed by iCORE MS/MS analysis. The resulting activities of individual biomarkers displayed markedly divergent kinetics (FIG. 11f). Biomarkers G3 and G4 both strongly increased relative to pretreatment baselines, reaching a plateau by week 11 despite staggered onset at week 7 and 3 respectively. G5 and G6 showed opposing kinetics, significantly decreasing at week 3 before either gradually returning to pretreatment intensities (G5) or persisting to week 11 (G6). Interestingly, G7 tracked with the kinetics of DDC treatment, elevating sharply at week 3 followed by a rapid reversal at week 7. All remaining biomarkers (G1, G2, G8, G9 and G10) did not deviate from initial pretreatment activities (G1-G10; *P<0.05, **P<0.01, repeated measures ANOVA, Tukey post test, n=10). Importantly, all biomarkers in control animals also did not significantly depart from baseline (FIG. 19).

Figure 20A:
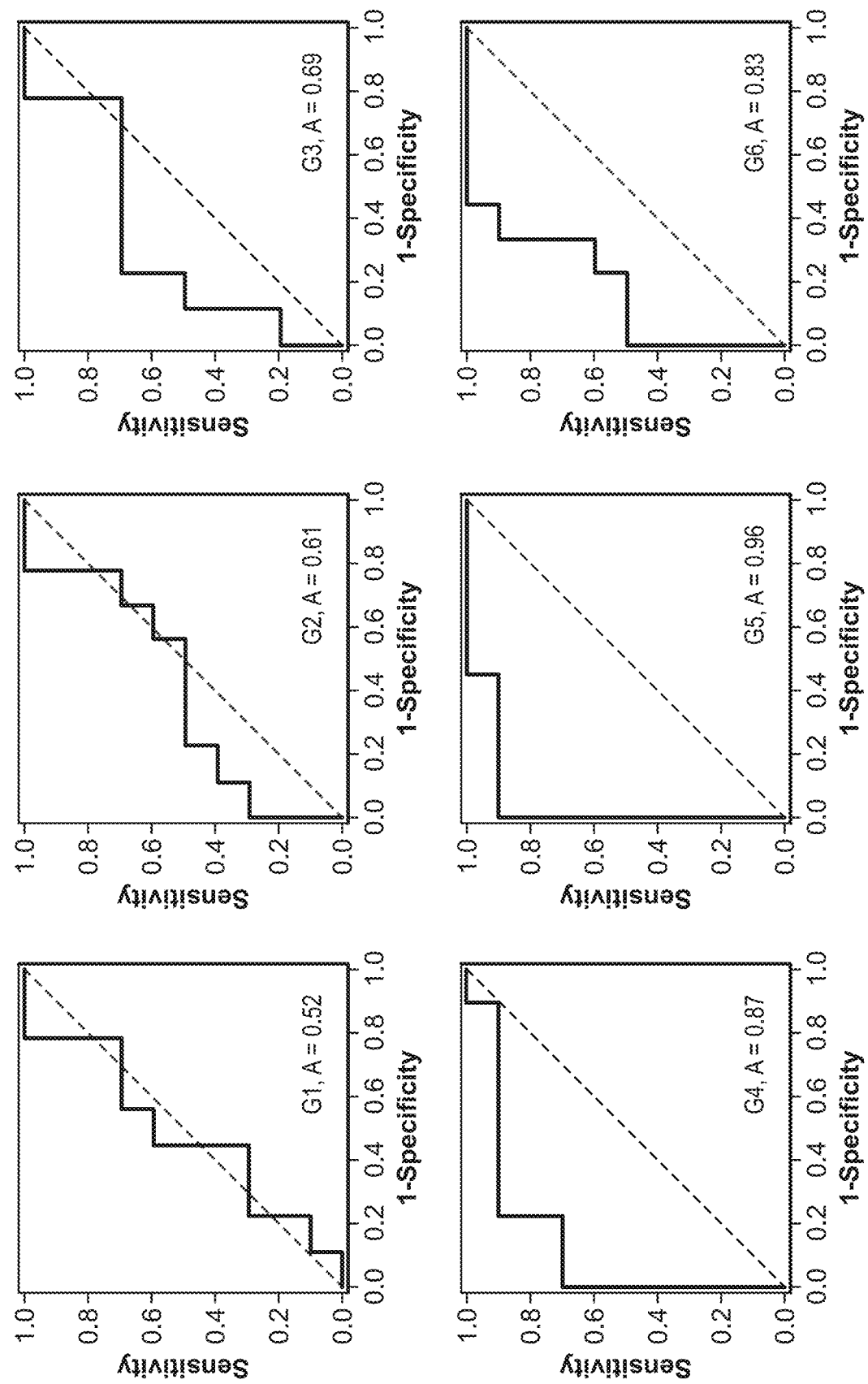

The diagnostic performance of these biomarkers was determined by performing receiver operating characteristic (ROC) analyses for individual as well as biomarker combinations. ROC curves characterize the sensitivity and specificity of a biomarker as a function of the discrimination threshold by returning the area under the curve (AUC) as a performance metric with a baseline AUC of 0.5 representing a random biomarker classifier (dashed line, FIG. 11g,h). Within the fibrosing window of 0-3 weeks, G5 displayed the highest AUC amongst the 10 biomarkers (0.96, FIG. 20), which was further improved by including G7 in a double biomarker combination (0.98), or G6 and G7 in a triple combination (1.00), resulting in a perfect synthetic biomarker classifier for fibrosing disease in this model (FIG. 11g). Within the resolving time frame of 7-11 weeks, G1 led with AUC=0.73 (FIG. 21), which was significantly improved via the dual combination of G1+G9 (AUC=0.9) and finally the triple combination G1+G7+G9 (AUC=0.91) (FIG. 11h).

Collectively, these experiments demonstrate that liver fibrosis and resolution are revealed by distinct collections of synthetic biomarkers, and that multiplexed combinations allow the highest diagnostic performance—illustrating the ability of this platform to noninvasively illuminate otherwise inaccessible aspects of liver disease evolution.

Example 11: Early Detection of Colorectal Tumors

When diagnosed prior to systemic dissemination, many primary tumors can be effectively treated with conventional clinical interventions.[36] However, most clinically-utilized biomarkers lack the diagnostic accuracy and sensitivity to discriminate small tumors, and it remains unclear whether current endogenous blood biomarker strategies targeting shed or processed byproducts of cancerous tissue can be sufficiently improved for early detection.[19] Moreover, it is becoming apparent that individual serum biomarkers (e.g. CA-125 for ovarian, PSA for prostate cancer) do not possess the necessary sensitivity and specificity required for early detection, and that panels of biomarkers are most likely required.[37]

Figure 22:
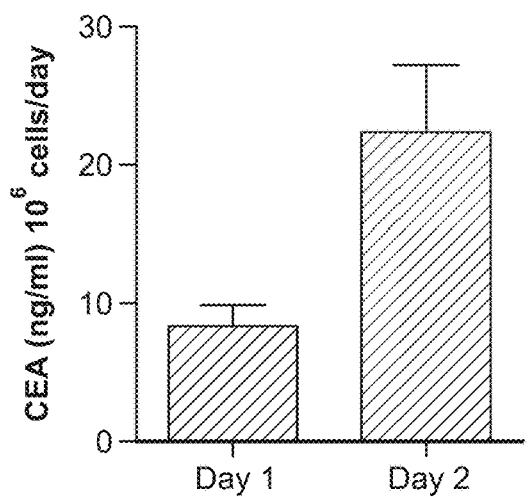
FIG. 22. In vitro CEA secretion by LS 174T human colorectal cancer cells. Quantification of CEA from media at days 1 and 2 by ELISA.
Figure 23A:
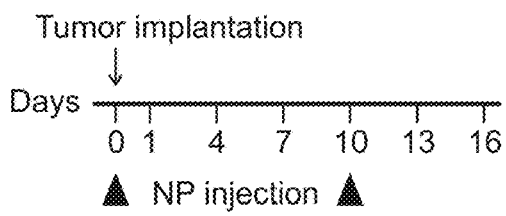
FIGS. 23A-23G. Synthetic biomarkers outperform serum CEA for early cancer detection.
Figure 23B:
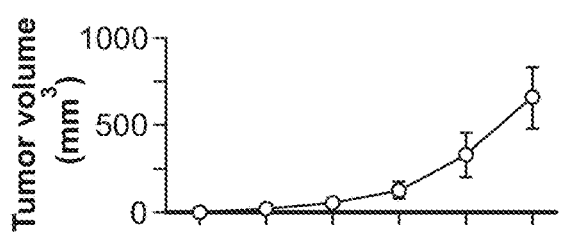
Figure 23C:
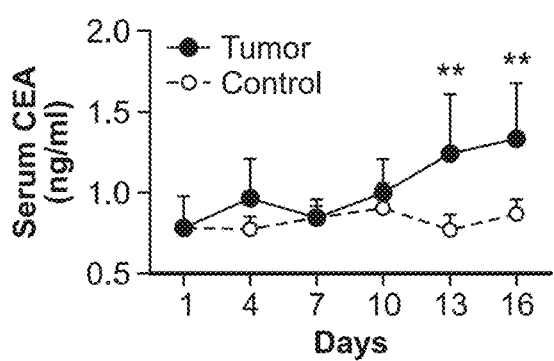
Figure 23D:
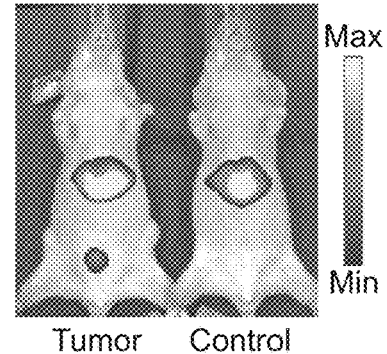
Figure 23E:
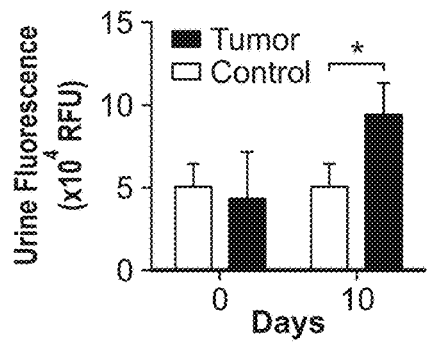
Figure 23F:
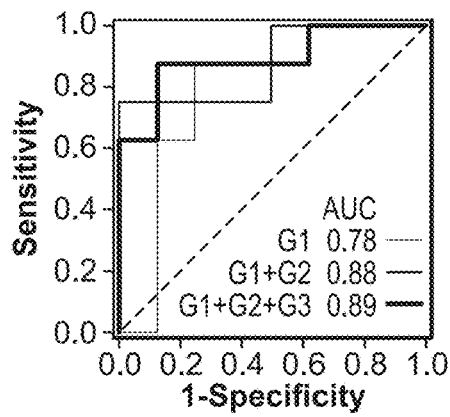
Figure 23G:
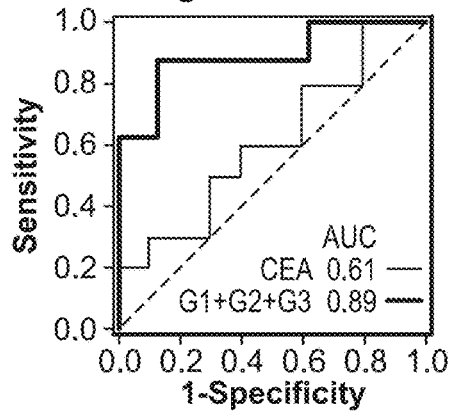
Figure 24A:
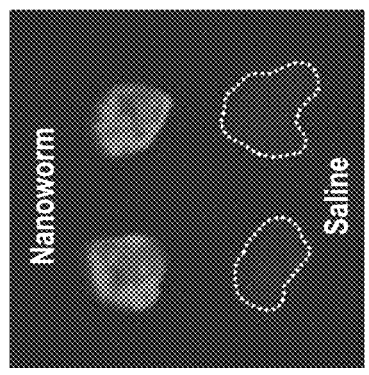
FIGS. 24A-24B. NW accumulation in tumor tissue. (a) VivoTag-680-labeled NWs or saline solutions were injected into LS 174T xenograft animals. Following excision, the tumors were scanned for NW accumulation. (b) Immunofluorescence analysis of tumor sections for blood vessels and NW. Scale bar=50 µm.
Figure 24B:
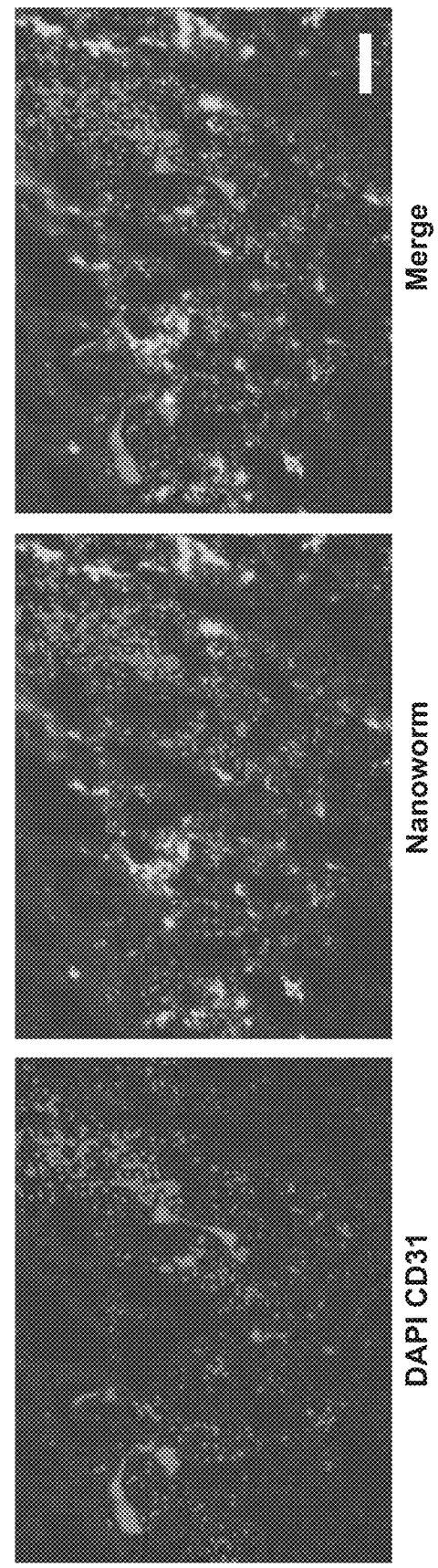
Figure 25A:
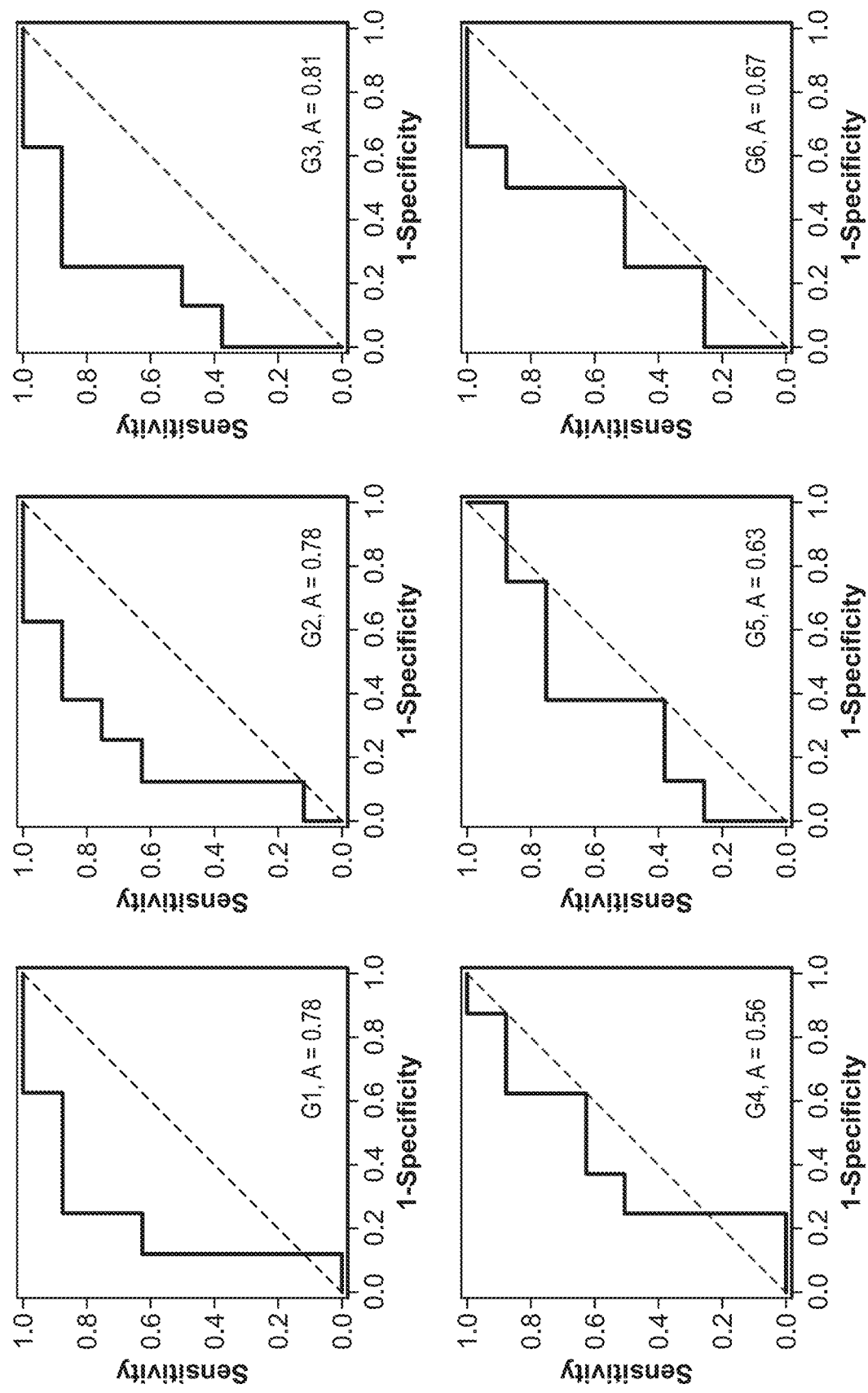
FIGS. 25A-25B. ROC curves of tumor biomarkers.
Figure 25B:
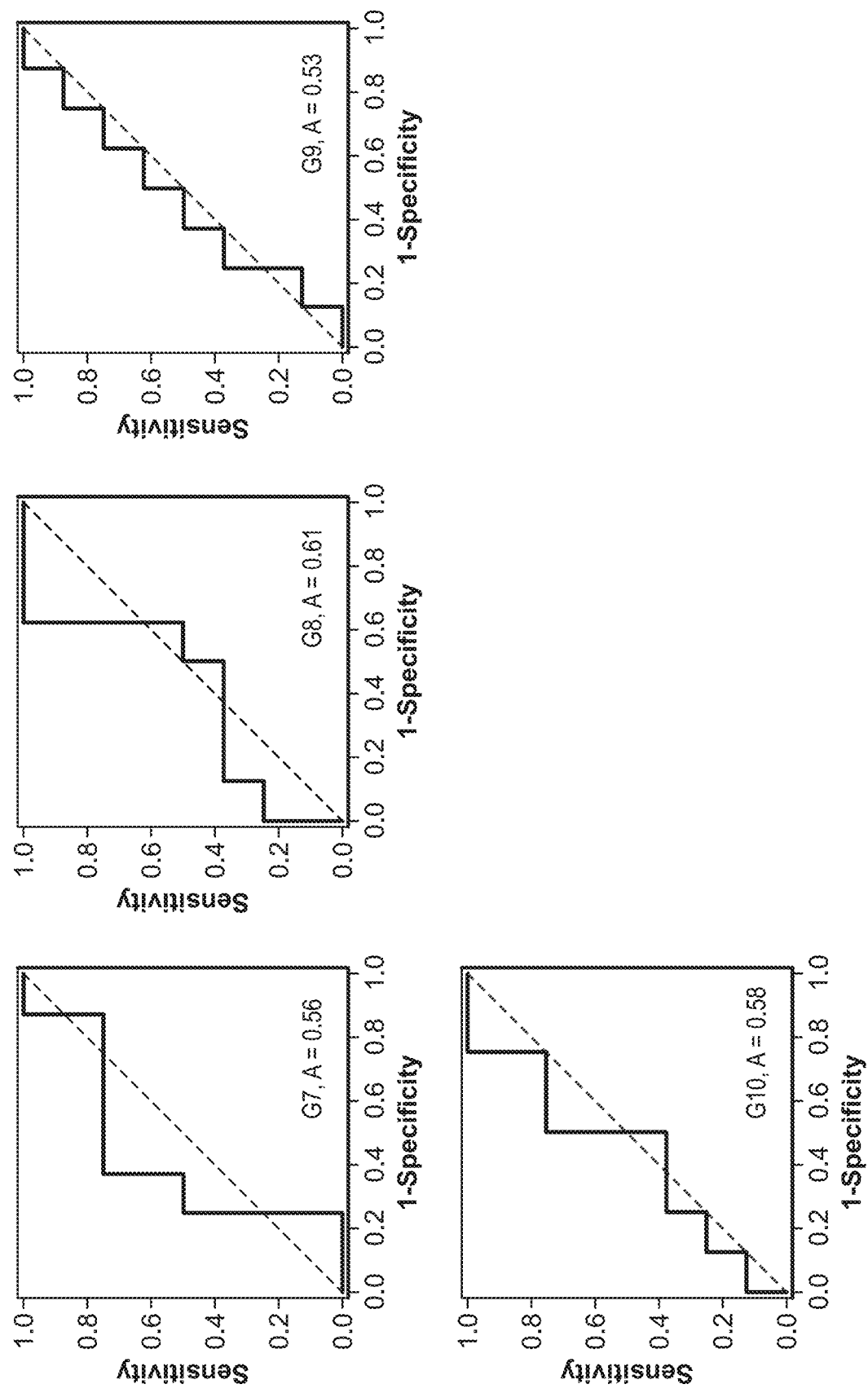

Here, it was investigated whether panels of synthetic urinary biomarkers could be readily adapted to allow earlier and more accurate detection of cancer compared with single clinical blood biomarkers, e.g., because nanoparticles can be passively targeted to tumors to sample proteases through fenestrated angiogenic tumor vessels.[16] In order to explore this concept, athymic nude mice were used bearing LS174T xenograft tumors, a human colorectal cancer (CRC) cell line[38] that secretes the blood biomarker carcinoembryonic antigen (CEA) as a model system (FIG. 22). FIG. 23a shows a timeline of LS 174T colorectal cancer cell inoculation and NW administration in Nude mice. FIG. 23b illustrates macroscopic quantification of tumor growth (n=5, s.d.), and FIG. 23c shows circulating levels of CEA in tumor and control animals analyzed every third day post tumor implantation by ELISA (**$P<0.01$, Two-way ANOVA, Tukey post test). IVIS in vivo imaging showed urinary accumulation of ensemble reporter library in tumor-bearing animals (d). FIG. 23e displays quantification of urinary fluorescence by FITC-immunoprecipitation (*$P<0.05$, Two-way ANOVA, Tukey post test; n=5, s.d.). FIG. 23f shows ROC curves of a single, double and triple biomarker combination with associated AUC (n=16; 8 ctrl, 8 tumor), and FIG. 23g shows ROC comparison between triple biomarker combination (G1+G2+G3) with serum CEA at day 10. Following implantation, tumor engraftment was monitored by sampling serum every 3 days and analyzing for CEA by ELISA (FIG. 23b,c). At day 10, CEA levels were insufficiently elevated to distinguish tumor from control animals, corresponding to an average tumor burden of ~130 mm$^3$ (spherical diameter d ~6.3 mm). Tumors permitted to grow further were readily detected by CEA analysis (day 13 and 16), representing a limit of detection of ~330 mm3 (d ~8.6 mm) (**$P<0.01$, Two way ANOVA, n=5). In order to determine whether synthetic urinary biomarkers could outperform serum CEA, the fluorophore-labeled, 10-plex peptide-NW library described herein was administered at day 0 and 10. Ex vivo imaging of excised tumors and immunofluorescence analysis of corresponding sections indicated that NWs readily homed to the extravascular milieu following i.v. administration (FIG. 24). Despite the inability of CEA to indicate the presence of cancer at day 10, ensemble peptide cleavage resulted in a strong 2-fold elevation in urine fluorescence (FIG. 23d,e), allowing the detection of tumors ~2.5-times smaller than CEA (130 vs. 330 mm$^3$) by urinary fluorescence alone. To determine the full diagnostic potential of multiplexed analysis, individual biomarkers were quantified by iCORE MS/MS. Similar to the liver studies described herein, the classifying power of the highest performing single biomarker (G1, AUC=0.78, FIG. 25) steadily improved in double (G1+G2, AUC=0.88) and triple biomarker combinations (G1+G2+G3, AUC=0.89) (n=16, FIG. 23f). This triple combination significantly outperformed serum CEA, which detected disease poorly with an AUC of 0.61 at day 10 (FIG. 23g).

DISCUSSION

Despite the fact that many new features of disease are rapidly being discovered with global profiling approaches, the development of this knowledge into next-generation biomarkers remains fundamentally limited by many technical and biological challenges intrinsic to endogenous targets. Ideally, a candidate biomarker would be secreted at high levels relative to native background, remain stable or persistent in circulation until detection, be readily accessible from compositionally simple host fluids, and be able to discriminate disease with high sensitivity and specificity. In practice, such parameters are difficult to improve or control, and many promising biomarkers fail during rigorous evaluation for clinical translation.

Here, a system of synthetic biomarkers was devised with the capacity to (i) amplify biomarker levels through substrate turnover by targeting aberrant protease activities, (ii) release stable, d-isomer enriched mass reporters designed to be detected within a narrow mass window free of host molecules, (iii) trigger reporter clearance from blood into urine to reduce matrix complexity and to facilitate facile extraction, and (iv) simultaneously profile libraries of candidate synthetic biomarkers in vivo to identify multiplexed combinations for highly sensitive and specific diagnosis. The work described herein shows that by engineering exogenous agents to interrogate diseased tissues, key biological and transport challenges can be separately addressed prior to integration, resulting in synthetic biomarkers that can be rapidly designed, tested and identified for distinct diseases.

The liver studies described herein demonstrate the potential of this technology for monitoring both liver fibrosis and resolution. Currently, the needle biopsy remains the gold standard despite the fact that biopsy results are often variable because only a small part of the liver is sampled and can lead to inaccurate diagnosis or repeat biopsies. Furthermore, gross architectural changes frequently occur at a longer time scale compared with alterations in protease activities as occurs during resolution, making it challenging to predict patient trajectory based on histological analysis. Notably, this study showed that nanoscale agents penetrate throughout the liver, delineated a panel of fibrosing and resolving biomarkers (0-3 and 7-11 weeks respectively), and even revealed biomarkers between week 3 and 7 (e.g. G3, G7) that could potentially represent an anticipatory signature in advance of resolution since liver sections within this time window were indistinguishable by clinically-utilized histological or matrix quantification assays. Early predictive biomarkers of fibrotic resolution would accelerate the rate in which new anti-fibrotic drugs are identified in preclinical and clinical studies by quickly differentiating potential responders from non-responders with identical histology.

Currently, little clinical data exists correlating the size of tumors to circulating biomarker levels and it remains unclear whether small tumors (<1 cm$^3$) can be reliably detected. Recently, Gambhir and colleagues[19] have estimated via mathematical modeling that solid tumors could potentially remain undetectable for 10-12 years and reach a spherical diameter >2.5 cm before blood biomarkers could indicate disease. In order to be useful for early detection, current approaches dependent on endogenous species will need to be greatly improved. In comparison, this study showed that multiplexed synthetic biomarker panels can detect CRC tumors earlier and more precisely than serum CEA, enabling the detection of tumor burdens ~2.5-fold smaller. It further illustrated that relatively small diseased sites (~130 mm$^3$) outside of the liver are accessible for interrogation, opening the possibility of detecting disease at sites currently challenging to probe with near-infrared imaging (e.g. deep seeded tumors) or with other imaging modalities (e.g. diseased tissues with poor MRI or CT contrast such as liver metastases).[39]

The technology described herein can be readily extended to encompass additional diseases and alternative applications. Given the cumulative wealth of approved and experimental nanoparticle formulations, the work described herein is transferrable to other nanomaterials and scaffolds that can actively target or transport peptide cargo to different organs, types of vasculature, and tissue depths.[40,41] Further, the iCORE mass-encoding scheme disclosed herein can be extended to create hundreds of orthogonal codes by incorporating additional isotope-enriched amino acids and by making use of distinct parent peptides. A larger encoding library would not only enable the simultaneous monitoring of hundreds of synthetic biomarkers, but could additionally allow the identities of dysregulated proteases to be revealed by mathematical deconvolution[42] to overcome the challenges of designing specific substrates for promiscuous proteases. A collection of diverse delivery strategies, broader multiplexing capabilities, and precise mathematical algorithms would provide rich opportunities for systems-level monitoring of disease and clearly elucidate the roles that complex protease networks play in heath and disease.

REFERENCES

[1] Sawyers, C. L. The cancer biomarker problem. Nature 452, 548-552 (2008).
[2] Hanash, S. M., Pitteri, S. J., and Faca, V. M. Mining the plasma proteome for cancer biomarkers. Nature 452, 571-579 (2008).
[3] Sreekumar, A. et al. Metabolomic profiles delineate potential role for sarcosine in prostate cancer progression. Nature 457, 910-914 (2009).
[4] Villanueva, J. et al. Differential exoprotease activities confer tumor-specific serum peptidome patterns. J. Clin. Invest. 116, 271-284 (2006).
[5] Surinova, S. et al. On the development of plasma protein biomarkers. J. Proteome Res. 10, 5-16 (2011).
[6] Schwarzenbach, H., Hoon, D. S. B., and Pantel, K. Cell-free nucleic acids as biomarkers in cancer patients. Nat. Rev. Cancer 11, 426-437 (2011).
[7] Moon, P.-G., You, S., Lee, J.-E., Hwang, D., and Baek, M.-C. Urinary exosomes and proteomics. Mass Spectrom. Rev. 30, 1185-1202 (2011).
[8] Nagrath, S. et al. Isolation of rare circulating tumour cells in cancer patients by microchip technology. Nature 450, 1235-1239 (2007).
[9] Lutz, A. M., Willmann, J. K., Cochran, F. V., Ray, P., and Gambhir, S. S. Cancer screening: a mathematical model relating secreted blood biomarker levels to tumor sizes. PloS Med. 5, e170 (2008).
[10] Anderson, N. L. and Anderson, N. G. The human plasma proteome: history, character, and diagnostic prospects. Mol. Cell. Proteomics 1, 845-867 (2002).
[11] Haun, J. B. et al. Micro-nmr for rapid molecular analysis of human tumor samples. Sci. Transl. Med. 3, 71ra16 (2011).
[12] Fonovic, M. and Bogyo, M. Activity-based probes as a tool for functional proteomic analysis of proteases. Expert Rev. Proteomics 5, 721-730 (2008).
[13] Baruch, A., Jeffery, D. A., and Bogyo, M. Enzyme activity—it's all about image. Trends Cell. Biol. 14, 29-35 (2004).
[14] Hilderbrand, S. A. and Weissleder, R. Near-infrared fluorescence: application to in vivo molecular imaging. Curr. Opin. Chem. Biol. 14, 71-79 (2010).
[15] Braet, F. and Wisse, E. Structural and functional aspects of liver sinusoidal endothelial cell fenestrae: a review. Comp. Hepatol. 1, 1 (2002).
[16] Jain, R. K. and Stylianopoulos, T. Delivering nanomedicine to solid tumors. Nat. Rev. Clin. Oncol. 7, 653-664 (2010).
[17] López-Otín, C. and Bond, J. S. Proteases: multifunctional enzymes in life and disease. J. Biol. Chem. 283, 30433-30437 (2008).
[18] Schuppan, D. and Afdhal, N. H. Liver cirrhosis. Lancet 371, 838-851 (2008). [19] Hori, S. S. and Gambhir, S. S. Mathematical model identifies blood biomarker-based early cancer detection strategies and limitations. Sci. Transl. Med. 3, 109ra116 (2011).
[20] Bremer, C., Tung, C. H., and Weissleder, R. In vivo molecular target assessment of matrix metalloproteinase inhibition. Nat. Med. 7, 743-748 (2001).
[21] Kridel, S. J. et al. A unique substrate binding mode discriminates membrane type-1 matrix metalloproteinase from other matrix metalloproteinases. J. Biol. Chem. 277, 23788-23793 (2002).
[22] Lutolf, M. P. et al. Repair of bone defects using synthetic mimetics of collagenous extracellular matrices. Nat. Biotechnol. 21, 513-518 (2003).
[23] Mahmood, U. and Weissleder, R. Near-infrared optical imaging of proteases in cancer. Mol. Cancer Ther. 2, 489-496 (2003).
[24] Turk, B. E., Huang, L. L., Piro, E. T., and Cantley, L. C. Determination of protease cleavage site motifs using mixture-based oriented peptide libraries. Nat. Biotechnol. 19, 661-667 (2001).
[25] Park, J.-H. et al. Systematic surface engineering of magnetic nanoworms for in vivo tumor targeting. Small 5, 694-700 (2009).
[26] Fickert, P. et al. A new xenobiotic-induced mouse model of sclerosing cholangitis and biliary fibrosis. Am. J. Pathol. 171, 525-536 (2007).
[27] Morris, T. A. et al. Urine and plasma levels of fibrinopeptide b in patients with deep vein thrombosis and pulmonary embolism. Thromb. Res. 110, 159-165 (2003).
[28] Choi, H. S. et al. Renal clearance of quantum dots. Nat. Biotechnol. 25, 1165-1170 (2007).
[29] Villanueva, J., Nazarian, A., Lawlor, K., Yi, S. S., Robbins, R. J., and Tempst, P. A sequence-specific exopeptidase activity test (sseat) for "functional" biomarker discovery. Mol. Cell. Proteomics 7, 509-518 (2008).
[30] Brown, B. B., Wagner, D. S., and Geysen, H. M. A single-bead decode strategy using electrospray ionization mass spectrometry and a new photolabile linker: 3-amino-3-(2-nitrophenyl)propionic acid. Mol. Divers. 1, 4-12 (1995).
[31] Ross, P. L. et al. Multiplexed protein quantitation in Ssaccharomyces cerevisiae using amine-reactive isobaric tagging reagents. Mol. Cell. Proteomics 3, 1154-1169 (2004).

[32] Thompson, A. et al. Tandem mass tags: a novel quantification strategy for comparative analysis of complex protein mixtures by MS/MS. Anal. Chem. 75, 1895-1904 (2003).
[33] Rockey, D. C., Caldwell, S. H., Goodman, Z. D., Nelson, R. C., Smith, A. D., and for the Study of Liver Diseases, A. A. Liver biopsy. Hepatology 49, 1017-1044 (2009).
[34] Popov, Y. and Schuppan, D. Targeting liver fibrosis: strategies for development and validation of antifibrotic therapies. Hepatology 50, 1294-1306 (2009).
[35] Bedossa, P., Dargére, D., and Paradis, V. Sampling variability of liver fibrosis in chronic hepatitis C. Hepatology 38, 1449-1457 (2003).
[36] Etzioni, R. et al. The case for early detection. Nat. Rev. Cancer 3, 243-252 (2003).
[37] Kulasingam, V., Pavlou, M. P., and Diamandis, E. P. Integrating high-throughput technologies in the quest for effective biomarkers for ovarian cancer. Nat. Rev. Cancer 10, 371-378 (2010).
[38] D'Souza, A. L. et al. A strategy for blood biomarker amplification and localization using ultrasound. Proc. Natl. Acad. Sci. 106, 17152-17157 (2009).
[39] Schima, W., Kulinna, C., Langenberger, H., and Ba-Ssalamah, A. Liver metastases of colorectal cancer: US, CT or MR? Cancer Imaging 5 Spec No A, S149-S156 (2005).
[40] Ruoslahti, E., Bhatia, S. N., and Sailor, M. J. Targeting of drugs and nanoparticles to tumors. J. Cell Biol. 188, 759-768 (2010).
[41] Sugahara, K. N. et al. Science 328, 1031-1035 (2010).
[42] Miller, M. A. et al. Proteolytic activity matrix analysis (prama) for simultaneous determination of multiple protease activities. Integr. Biol. 3, 422-438 (2011).
[43] Popov, Y., Patsenker, E., Fickert, P., Trauner, M., and Schuppan, D. Mdr2 (abcb4)−/− mice spontaneously develop severe biliary fibrosis via massive dysregulation of pro- and antifibrogenic genes. J. Hepatol. 43, 1045-1054 (2005).

The entire contents of all references described or listed herein, including references [1]-[43] listed above, any references described in the specification above, and any reference described below, are incorporated herein by reference, as if each and every individual reference was incorporated herein by reference. In case of a conflict between the teachings of any reference incorporated herein and the specification, the specification shall control.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

As used herein and in the appended claims, the singular forms "a", "an", and "the" include the plural reference unless the context clearly indicates otherwise. Thus, for example, a reference to "a cell" includes a plurality of such cells, and a reference to "an antibody" is a reference to one or more antibodies and equivalents thereof known to those skilled in the art, and so forth.

Where ranges are given, endpoints are included. For each range an embodiment in which the described parameter assumes a single value within the range or a sub-range within the range is included.

Not all embodiments have been described and combination of a feature or of multiple features of any embodiment (s) described herein with any feature or multiple features of any other embodiment(s) described herein is contemplated. Similarly, any limitations in any of the appended claims may be combined with any limitation in any of the other claims, or a combination of such limitations. Such combined embodiments have not been explicitly set forth to save space, but are expressly contemplated to be within the scope of the present invention. Similarly, any feature(s) of any embodiment described herein may be excluded from the scope of the appended claims.

All references, patents and patent publications that are recited in this application are incorporated in their entirety herein by reference.

The invention claimed is:

1. A set of isotope coded reporter molecules (iCOREs), comprising:
a plurality of different iCOREs, each comprising a unique isotope signature and each iCORE being linked to a carrier domain by a protease substrate, wherein the set of iCOREs comprises substrates for different proteases, wherein the iCOREs comprise at least one of SEQ ID NO: 8-SEQ ID NO: 17, as follows:

$$e^{+3}G^{+6}VndneeGFfsAr-X-K(FAM)GGPQGIWGQ; \quad \text{(SEQ ID NO: 8)}$$

$$e^{+2}G^{+6}Vndnee^{+1}GFfsAr-X-K(FAM)GGLVPRGSG; \quad \text{(SEQ ID NO: 9)}$$

$$e^{+1}G^{+6}Vndnee^{+2}GFfsAr-X-K(FAM)GGPVGLIG; \quad \text{(SEQ ID NO: 10)}$$

$$eG^{+6}Vndnee^{+2}GFfs^{+1}Ar-X-K(FAM)GGPWGIWGQG; \quad \text{(SEQ ID NO: 11)}$$

$$eG^{+5}VndneeGFfs^{+4}Ar-X-K(FAM)GGPVPLSLVM; \quad \text{(SEQ ID NO: 12)}$$

$$e^{+3}G^{+1}Vndnee^{+1}GFfs^{+4}Ar-X-K(FAM)GGPLGLRSW; \quad \text{(SEQ ID NO: 13)}$$

$$e^{+3}GVndneeG^{+6}FfsAr-X-K(FAM)GGPLGVRGK; \quad \text{(SEQ ID NO: 14)}$$

$$e^{+2}GVndneeG^{+6}Ffs^{+1}Ar-X-K(FAM)GGf(PiP)RSGGG; \quad \text{(SEQ ID NO: 15)}$$

$$e^{+1}GVndnee^{+2}G^{+6}FfsAr-X-K(FAM)GGfPRSGGG; \text{ or} \quad \text{(SEQ ID NO: 16)}$$

$$eGVndnee^{+3}G^{+6}FfsAr-X-K(FAM)GGf(PiP)KSGGG, \quad \text{(SEQ ID NO: 17)}$$

wherein,
X represents 3-amino-3-(2-nitrophenyl)propionic acid,
FAM represents carboxyfluorescein,
PiP represents pipecolic acid, and
lower case represents d-amino acid.

2. A set of isotope coded reporter molecules (iCOREs), wherein the set of iCOREs comprises SEQ ID NO: 8-SEQ ID NO: 17, as follows:

$$e^{+3}G^{+6}VndneeGFfsAr-X-K(FAM)GGPQGIWGQ; \quad \text{(SEQ ID NO: 8)}$$

$$e^{+2}G^{+6}Vndnee^{+1}GFfsAr-X-K(FAM)GGLVPRGSG; \quad \text{(SEQ ID NO: 9)}$$

$$e^{+1}G^{+6}Vndnee^{+2}GFfsAr-X-K(FAM)GGPVGLIG; \quad \text{(SEQ ID NO: 10)}$$

$$eG^{+6}Vndnee^{+2}GFfs^{+1}Ar-X-K(FAM)GGPWGIWGQG; \quad \text{(SEQ ID NO: 11)}$$

$$eG^{+5}VndneeGFfs^{+4}Ar-X-K(FAM)GGPVPLSLVM; \quad \text{(SEQ ID NO: 12)}$$

$$e^{+3}G^{+1}Vndnee^{+1}GFfs^{+4}Ar-X-K(FAM)GGPLGLRSW; \quad \text{(SEQ ID NO: 13)}$$

$$e^{+3}GVndneeG^{+6}FfsAr-X-K(FAM)GGPLGVRGK; \quad \text{(SEQ ID NO: 14)}$$

$$e^{+2}GVndneeG^{+6}Ffs^{+1}Ar-X-K(FAM)GGf(PiP)RSGGG; \quad \text{(SEQ ID NO: 15)}$$

$$e^{+1}GVndnee^{+2}G^{+6}FfsAr-X-K(FAM)GGfPRSGGG; \text{ and} \quad \text{(SEQ ID NO: 16)}$$

$$eGVndnee^{+3}G^{+6}FfsAr-X-K(FAM)GGf(PiP)KSGGG, \quad \text{(SEQ ID NO: 17)}$$

wherein,
X represents 3-amino-3-(2-nitrophenyl)propionic acid,
FAM represents carboxyfluorescein,
PiP represents pipecolic acid, and
lower case represents d-amino acid.

3. A set of isotope coded reporter molecules (iCOREs), comprising:
a plurality of different iCOREs, each comprising a unique isotope signature and each iCORE being linked to a carrier domain by a protease substrate, wherein the set of iCOREs comprises substrates for different proteases, wherein each amino acid sequence susceptible to cleavage comprises the amino acid sequence: PQGIWGQ (SEQ ID NO: 18), LVPRGSG (SEQ ID NO: 19), PVGLIG (SEQ ID NO: 20), PWGIWGQG (SEQ ID NO: 21), PVPLSLVM (SEQ ID NO: 22), PLGLRSW (SEQ ID NO: 23), PLGVRGK (SEQ ID NO: 24), GGPLA(Nva)(Dap)ARGC (SEQ ID NO: 35), dF(PiP)RSGGG (SEQ ID NO: 25), dFPRSGGG (SEQ ID NO: 26), or dF(PiP)KSGGG (SEQ ID NO: 27), and wherein:

Nva represents norvaline,
PiP represents pipecolic acid,
dF represents d-phenylalanine, and
Dap represents N-beta-(2,4-dinitrophenyl)-L-alpha,beta-diaminopropionic acid.

4. A composition comprising a sequence selected from the group consisting of SEQ ID NO: 8-SEQ ID NO: 17, as follows:

```
                                        (SEQ ID NO: 8)
e+3G+6VndneeGFfsAr-X-K(FAM)GGPQGIWGQ;

(SEQ ID NO: 9)
e+2G+6Vndnee+1GFfsAr-X-K(FAM)GGLVPRGSG;

(SEQ ID NO: 10)
e+1G+6Vndnee+2GFfsAr-X-K(FAM)GGPVGLIG;

(SEQ ID NO: 11)
eG+6Vndnee+2GFfs+1Ar-X-K(FAM)GGPWGIWGQG;

(SEQ ID NO: 12)
eG+5VndneeGFfs+4Ar-X-K(FAM)GGPVPLSLVM;

(SEQ ID NO: 13)
e+3G+1Vndnee+1GFfs+4Ar-X-K(FAM)GGPLGLRSW;

(SEQ ID NO: 14)
e+3GVndneeG+6FfsAr-X-K(FAM)GGPLGVRGK;

(SEQ ID NO: 15)
e+2GVndneeG+6Ffs+1Ar-X-K(FAM)GGf(PiP)RSGGG;

(SEQ ID NO: 16)
e+1GVndnee+2G+6FfsAr-X-K(FAM)GGfPRSGGG; and (SEQ ID NO: 17)
eGVndnee+3G+6FfsAr-X-K(FAM)GGf(PiP)KSGGG,
``` wherein,
X represents 3-amino-3-(2-nitrophenyl)propionic acid,
FAM represents carboxyfluorescein,
PiP represents pipecolic acid, and
lower case represents d-amino acid.

5. A reagent, comprising:
a particle; and
a plurality of substrates independently conjugated to the particle, wherein each of the substrates comprises a protease-cleavable linker linked to an iCORE comprising a unique isotope signature.

6. The reagent of claim 5, wherein the substrates are peptides.

7. The reagent of claim 6, wherein each substrate comprises one or more of the amino acid sequences selected from: PQGIWGQ (SEQ ID NO: 18), LVPRGSG (SEQ ID NO: 19), PVGLIG (SEQ ID NO: 20), PWGIWGQG (SEQ ID NO: 21), PVPLSLVM (SEQ ID NO: 22), PLGLRSW (SEQ ID NO: 23), PLGVRGK (SEQ ID NO: 24), GGPLA(Nva)(Dap)ARGC (SEQ ID NO: 35), dF(PiP)RSGGG (SEQ ID NO: 25), dFPRSGGG (SEQ ID NO: 26), or dF(PiP)KSGGG (SEQ ID NO: 27), wherein:

Nva represents norvaline,
PiP represents pipecolic acid,
dF represents d-phenylalanine, and
Dap represents N-beta-(2,4-dinitrophenyl)-L-alpha,beta-diaminopropionic acid.

8. The reagent of claim 5, wherein each iCORE comprises about 5-10, about 5-15, about 10-15, about 5-20, about 10-20, about 15-20, about 10-30, about 15-30, about 20-30, about 20-40, about 5-50, about 10-50, about 20-50, about 30-50, about 40-60, about 50-70, about 50-80, about 50-90, about 10-100, about 20-100, about 30-100, about 40-100, or about 50-100 amino acid residues.

9. The reagent of claim 5, wherein each iCORE comprises an amino acid sequence selected from the group consisting of EGVNDNEEGFFSAR (SEQ ID NO: 1), PPGFSPFR (SEQ ID NO: 30), DRVYIHPFHL (SEQ ID NO: 31), SYSMEHFRWGKPVGKKR (SEQ ID NO: 32), RPVKVYPNGAEDESAEAFPLEF (SEQ ID NO: 33), and FRWGKPVGKKRRPVKVYPNGAEDESAEAFPLE (SEQ ID NO: 34).

10. The reagent of claim 5, wherein each iCORE is a protein comprising one or more D-amino acids.

11. The reagent of claim 5, wherein each substrate has a sequence selected from the group consisting of SEQ ID NO: 8-SEQ ID NO: 17, as follows:

```
                                        (SEQ ID NO: 8)
e+3G+6VndneeGFfsAr-X-K(FAM)GGPQGIWGQ;

(SEQ ID NO: 9)
e+2G+6Vndnee+1GFfsAr-X-K(FAM)GGLVPRGSG;

(SEQ ID NO: 10)
e+1G+6Vndnee+2GFfsAr-X-K(FAM)GGPVGLIG;

(SEQ ID NO: 11)
eG+6Vndnee+2GFfs+1Ar-X-K(FAM)GGPWGIWGQG;

(SEQ ID NO: 12)
eG+5VndneeGFfs+4Ar-X-K(FAM)GGPVPLSLVM;

(SEQ ID NO: 13)
e+3G+1Vndnee+1GFfs+4Ar-X-K(FAM)GGPLGLRSW;

(SEQ ID NO: 14)
e+3GVndneeG+6FfsAr-X-K(FAM)GGPLGVRGK;

(SEQ ID NO: 15)
e+2GVndneeG+6Ffs+1Ar-X-K(FAM)GGf(PiP)RSGGG;

(SEQ ID NO: 16)
e+1GVndnee+2G+6FfsAr-X-K(FAM)GGfPRSGGG; and (SEQ ID NO: 17)
eGVndnee+3G+6FfsAr-X-K(FAM)GGf(PiP)KSGGG,
``` wherein,
X represents 3-amino-3-(2-nitrophenyl)propionic acid,
FAM represents carboxyfluorescein,
PiP represents pipecolic acid, and
lower case represents d-amino acid.

12. The set of iCOREs of claim 1, wherein the protease substrate is a substrate for a disease-associated protease.

13. The set of iCOREs of claim 1, wherein the carrier domain is an inorganic particle.

14. The reagent of claim 5, wherein the protease-cleavable linker is a substrate for a disease-associated protease.

15. The reagent of claim 5, wherein the particle is an inorganic particle.

* * * * *